(12) United States Patent
Fowler et al.

(10) Patent No.: US 9,506,845 B2
(45) Date of Patent: *Nov. 29, 2016

(54) METHODS, SYSTEMS AND DEVICES FOR MULTIPLE SINGLE-CELL CAPTURING AND PROCESSING USING MICROFLUIDICS

(71) Applicant: Fluidigm Corporation, San Francisco, CA (US)

(72) Inventors: Brian Fowler, San Mateo, CA (US); Jake Kimball, Oakland, CA (US); Myo Thu Maung, Brisbane, CA (US); Andrew May, San Francisco, CA (US); Michael C. Norris, Mountain View, CA (US); Dominique G. Toppani, Oakland, CA (US); Marc A. Unger, San Mateo, CA (US); Jing Wang, Daly City, CA (US); Jason A. A. West, Pleasanton, CA (US)

(73) Assignee: Fluidigm Corporation, South San Francisco, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 13/781,318

(22) Filed: Feb. 28, 2013

(65) Prior Publication Data

US 2013/0296196 A1 Nov. 7, 2013

Related U.S. Application Data

(60) Provisional application No. 61/605,016, filed on Feb. 29, 2012.

(51) Int. Cl.
*C12P 19/34* (2006.01)
*G01N 1/28* (2006.01)
(Continued)

(52) U.S. Cl.
CPC .......... *G01N 1/28* (2013.01); *B01L 3/502761* (2013.01); *C12P 19/34* (2013.01);
(Continued)

(58) Field of Classification Search
USPC .............................. 435/6.12, 91.2
See application file for complete search history.

(56) References Cited

U.S. PATENT DOCUMENTS 5,635,358 A 6/1997 Wilding et al.
6,408,878 B2 6/2002 Unger et al.
(Continued)

FOREIGN PATENT DOCUMENTS

WO 98/00231 A1 1/1998
WO 00/60352 A2 10/2000
(Continued)

OTHER PUBLICATIONS

Meyer et al., (Aug. 1, 2007) "Targeted High-Throughput Sequencing of Tagged Nucleic Acid Samples," Nucleic Acids Research 35(12): e97, 5 pages.
(Continued)

*Primary Examiner* — Kenneth Horlick
(74) *Attorney, Agent, or Firm* — Kilpatrick Townsend & Stockton LLP

(57) ABSTRACT

Methods, systems, and devices are described for multiple single-cell capturing and processing utilizing microfluidics. Tools and techniques are provided for capturing, partitioning, and/or manipulating individual cells from a larger population of cells along with generating genetic information and/or reactions related to each individual cell. Different capture configurations may be utilized to capture individual cells and then processing each individual cell in a multichamber reaction configuration. Some embodiments may provide for specific target amplification, whole genome amplification, whole transcriptome amplification, real-time PCR preparation, copy number variation, preamplification, mRNA sequencing, and/or haplotyping of the multiple individual cells that have been partitioned from the larger population of cells. Some embodiments may provide for other applications. Some embodiments may be configured for imaging the individual cells or associated reaction products as part of the processing. Reaction products may be harvested and/or further analyzed in some cases.

27 Claims, 42 Drawing Sheets

(51) Int. Cl.
*C12Q 1/68* (2006.01)
*G01N 1/34* (2006.01)
*G01N 15/14* (2006.01)
*B01L 3/00* (2006.01)
*B01L 7/00* (2006.01)

(52) U.S. Cl.
CPC ........... *C12Q 1/686* (2013.01); *C12Q 1/6813* (2013.01); *C12Q 1/6844* (2013.01); *C12Q 1/6869* (2013.01); *G01N 1/34* (2013.01); *G01N 15/1484* (2013.01); *B01L 7/52* (2013.01); *B01L 2200/0668* (2013.01); *B01L 2300/0864* (2013.01); *B01L 2400/043* (2013.01); *B01L 2400/0409* (2013.01); *B01L 2400/0415* (2013.01); *B01L 2400/0487* (2013.01); *B01L 2400/086* (2013.01); *B01L 2400/088* (2013.01)

(56) References Cited

U.S. PATENT DOCUMENTS

| | | |
|---|---|---|
| 6,506,609 B1 | 1/2003 | Wada et al. |
| 6,540,895 B1 | 4/2003 | Spence et al. |
| 6,645,432 B1 | 11/2003 | Anderson et al. |
| 6,692,952 B1 | 2/2004 | Braff et al. |
| 6,752,922 B2 | 6/2004 | Huang et al. |
| 6,767,706 B2 | 7/2004 | Quake et al. |
| 6,899,137 B2 | 5/2005 | Unger et al. |
| 6,960,437 B2 | 11/2005 | Enzelberger et al. |
| 7,214,298 B2 | 5/2007 | Spence et al. |
| 7,294,503 B2 | 11/2007 | Quake et al. |
| 7,312,085 B2 | 12/2007 | Chou et al. |
| 7,378,280 B2 | 5/2008 | Quake et al. |
| 7,407,799 B2 | 8/2008 | Balagadde et al. |
| 7,452,726 B2 | 11/2008 | Chou et al. |
| 7,678,547 B2 | 3/2010 | Eyal et al. |
| 8,129,176 B2 | 3/2012 | Quake et al. |
| 8,168,139 B2 | 5/2012 | Manger et al. |
| 8,206,975 B2 | 6/2012 | Bao et al. |
| 8,257,666 B2 | 9/2012 | Quake et al. |
| 8,273,574 B2 | 9/2012 | Quake et al. |
| 8,628,923 B2 | 1/2014 | Hamilton et al. |
| 8,658,418 B2 | 2/2014 | Daridon |
| 8,673,645 B2 | 3/2014 | Quake et al. |
| 9,304,065 B2 | 4/2016 | Fowler et al. |
| 2002/0109114 A1 | 8/2002 | Driggs et al. |
| 2002/0127736 A1 | 9/2002 | Chou et al. |
| 2002/0164816 A1 | 11/2002 | Quake |
| 2003/0008308 A1 | 1/2003 | Enzelberger et al. |
| 2003/0075446 A1 | 4/2003 | Culbertson et al. |
| 2003/0124599 A1 | 7/2003 | Chen et al. |
| 2003/0138829 A1 | 7/2003 | Unger et al. |
| 2003/0190608 A1 | 10/2003 | Blackburn |
| 2004/0053290 A1 | 3/2004 | Terbrueggen et al. |
| 2004/0072278 A1* | 4/2004 | Chou ............... B01L 3/502761 435/29 |
| 2004/0115838 A1 | 6/2004 | Quake et al. |
| 2005/0000900 A1 | 1/2005 | Huang et al. |
| 2005/0053952 A1 | 3/2005 | Hong |
| 2005/0072946 A1 | 4/2005 | Studer et al. |
| 2006/0165559 A1 | 7/2006 | Greenstein et al. |
| 2007/0099289 A1 | 5/2007 | Irima et al. |
| 2008/0241843 A1 | 10/2008 | Zare et al. |
| 2008/0261295 A1 | 10/2008 | Butler et al. |
| 2009/0042737 A1 | 2/2009 | Katz et al. |
| 2009/0098541 A1 | 4/2009 | Southern et al. |
| 2009/0201504 A1 | 8/2009 | Ho et al. |
| 2009/0298067 A1* | 12/2009 | Irimia ............... G01N 33/56966 435/5 |
| 2009/0325276 A1 | 12/2009 | Battrell et al. |
| 2010/0003666 A1 | 1/2010 | Lee et al. |
| 2010/0035249 A1 | 2/2010 | Hayashizaki et al. |
| 2010/0120077 A1 | 5/2010 | Daridon |
| 2010/0170797 A1 | 7/2010 | Artlett et al. |
| 2010/0273681 A1 | 10/2010 | Cerrina et al. |
| 2010/0303687 A1 | 12/2010 | Blaga et al. |
| 2011/0269175 A1 | 11/2011 | Durack et al. |
| 2012/0040843 A1 | 2/2012 | Ducree et al. |
| 2012/0091235 A1 | 4/2012 | Li et al. |
| 2012/0156675 A1 | 6/2012 | Luerssen et al. |
| 2012/0196754 A1 | 8/2012 | Quake et al. |
| 2012/0223804 A1 | 9/2012 | Gaitas |
| 2013/0000758 A1 | 1/2013 | Hoen et al. |
| 2013/0078163 A1 | 3/2013 | Chung et al. |
| 2013/0130301 A1 | 5/2013 | Yoon et al. |
| 2013/0190212 A1 | 7/2013 | Handique et al. |
| 2013/0309707 A1 | 11/2013 | Bersano-Begey et al. |
| 2013/0323732 A1 | 12/2013 | Anderson et al. |
| 2015/0018226 A1 | 1/2015 | Hansen et al. |

FOREIGN PATENT DOCUMENTS

| | | |
|---|---|---|
| WO | 0101025 A2 | 1/2001 |
| WO | 01/85341 A1 | 11/2001 |
| WO | 03/085379 A2 | 10/2003 |
| WO | 2004/040001 A2 | 5/2004 |
| WO | 2005030822 A2 | 4/2005 |
| WO | 2005084191 A2 | 9/2005 |
| WO | 2008/130623 A1 | 10/2008 |

OTHER PUBLICATIONS

International Preliminary Report on Patentability for PCT Application No. PCT/US2013/028170 mailed Sep. 12, 2014.
Final Office Action for U.S. Appl. No. 13/781,307 mailed Oct. 22, 2014.
Notice of Allowance for U.S. Appl. No. 13/781,292 mailed on Dec. 2, 2015.
Notice of Allowance for U.S. Appl. No. 13/781,313 mailed on Nov. 30, 2015.
Non-Final Office Action in U.S. Appl. No. 13/781,292 mailed Jul. 30, 2014.
Non-Final Office Action in U.S. Appl. No. 13/781,307 mailed Jul. 18, 2014.
Non-Final Office Action in U.S. Appl. No. 13/781,328 mailed Jul. 29, 2014.
Wheeler et al., "Microfluidic Device for Single-Cell Analysis," Annal. Chem., 75: 3581-3586 (2003).
White et al., "High-Throughput Microfluidic Single-Cell RT-qPCR," PNAS 108(34): 13999-14004 (Aug. 23, 2011).
Non-Final Office Action for U.S. Appl. No. 13/781,313 mailed Feb. 9, 2015.
Final Office Action for U.S. Appl. No. 13/781,292, mailed Jun. 9, 2015.
Non-Final Office Action for U.S. Appl. No. 13/781,307 mailed Jun. 9, 2015.
Final Office Action for U.S. Appl. No. 13/781,328 mailed on Jun. 19, 2015.
Frimat et al., "A Microfluidic Array with Cellular Valving for Single Cell Co-Culture," Lab Chip 11: 231-237 (2011).
Kim et al., "Expanding the Horizons for Single-Cell Applications on Lab-on-a-Chip Devices," Methods in Molecular Biology 853: 199-210 (2012).
Weaver et al., "Advances in High-Throughput Single-Cell Microtechnologies," Current Opinion in Biotechnology 25: 114-123 (2014).
Yilmaz et al., "Single Cell Genome Sequencing," Current Opinion in Biotechnology 23: 437-443 (2012).
Unger et al., "Monolithic Microfabricated Valves and Pumps by Multilayer Soft Lithography," Science, Apr. 7, 2000, p. 113-116, vol. 288 (4 pages).
Quake & Scherer, "From Micro- to Nanofabrication with Soft Materials," Science, Nov. 24, 2000, p. 1536-1540, vol. 290 (6 pp.).

(56) References Cited

OTHER PUBLICATIONS

Thorsen et al., "Microfluidic Large-Scale Integration," Science, Oct. 18, 2002, p. 580-584, vol. 298 (5 pp.).

Chou et al., "A Microfabricated Rotary Pump," Biomedical Microdevices, 2001, p. 323-330, vol. 3, No. 4, (8 pp.).

Liu et al., "Solving the "World-to-Chip" Interface Problem with a Microfluidic Matrix," Analytical Chemistry, 2003, p. 4718-4723, vol. 75 (6 pp.).

Hong et al., "A nanoliter-scale nucleic acid processor with parallel architecture," Nature Biotechnology, Apr. 2004, p. 435-439, vol. 22, No. 4.

PCT International Search Report for International Application No. PCT/US2013/028170, mailed Jun. 25, 2013 (3 pp.).

Notice of Allowance for U.S. Appl. No. 13/781,307 mailed on Jan. 20, 2016.

Non-Final Office Action mailed on Jul. 1, 2016 for U.S. Appl. No. 13/781,313, 6 pages.

\* cited by examiner

↳—210-k-c

↳—210-k-d

↳—210-k-e 210-k-f 210-k-g

↖ 210-k-h

↖ 210-k-i 210-k-j 210-k-k

METHODS, SYSTEMS AND DEVICES FOR MULTIPLE SINGLE-CELL CAPTURING AND PROCESSING USING MICROFLUIDICS

CROSS-RELATED APPLICATIONS

The present application for patent claims priority to Provisional Application No. 61/605,016 entitled "METHODS, SYSTEMS, AND DEVICES FOR MULTIPLE SINGLE-PARTICLE OR SINGLE-CELL PROCESSING USING MICROFLUIDICS" filed Feb. 29, 2012, and assigned to the assignee hereof and hereby expressly incorporated by reference herein for all purposes.

BACKGROUND

The ability to perform molecular and cellular analyses of biological systems has grown explosively over the past several decades. In particular, the advent and refinement of molecular and cellular techniques, such as DNA sequencing, gene cloning, monoclonal antibody production, cell transfection, amplification techniques (such as PCR), and transgenic animal formation, have fueled this explosive growth. These techniques have spawned an overwhelming number of identified genes, encoded proteins, engineered cell types, and assays for studying these genes, proteins, and cell types. As the number of possible combinations of samples, reagents, and processes becomes nearly incalculable, it has become increasingly apparent that novel approaches may be necessary even to begin to make sense of this complexity, especially within reasonable temporal and monetary limitations.

SUMMARY

Methods, systems, and devices are described for multiple single-cell capturing and processing utilizing microfluidics. Embodiments may provide for capturing, partitioning, and/or manipulating individual cells from a larger population of cells along with generating genetic information and/or reaction products related to each individual cell. Some embodiments may provide for specific target amplification (STA), whole genome amplification (WGA), whole transcriptome amplification (WTA), real-time PCR preparation, and/or haplotyping of multiple individual cells that have been partitioned from a larger population of cells. Some embodiments may provide for other applications. Some specific embodiments provide for mRNA sequencing or preamplification of the multiple individual cells. Some embodiments may be configured for imaging the individual cells or associated reaction products as part of the processing. Reaction products may be harvest and/or further analyzed in some cases.

The methods, systems, and devices may include different microfluidic devices and/or controllers for multiple single-cell capturing and processing utilizing microfluidics. Some microfluidic devices are provided that may include multiple capture configurations and multiple multi-chamber reaction configurations. Each capture configuration may be configured to capture an individual cell from multiple cells. Each multi-chamber reaction configuration may then be utilized to process each cell after it has by lysed. Reactions products may be harvest from each multi-chamber reaction configuration. Microfluidic controllers are also provided that may be utilized to operate the microfluidic device to capture and to process individual cells from multiple cells.

Some embodiments include a microfluidic device for multiple single-cell capturing and processing. The microfluidic device may include: a plurality of capture configurations coupled in series, wherein each respective capture configuration is configured to capture a single cell; and a plurality of multi-chamber reaction configurations, wherein each respective multi-chamber reaction configuration is coupled with a respective capture configuration from the plurality of capture configurations and is configured for single-cell processing.

In some embodiments, each respective capture configuration comprises one or more a physical barriers sized to hold only a single cell. In some embodiments, each respective capture configuration includes: one or more bypass channels coupled with an input channel and an output channel; a drain coupled with the input channel and the output channel; and/or a capture nest situated proximal to a junction of the input channel and the one or more bypass channels and coupled with the drain, wherein the capture nest is configured to capture a single cell from a plurality of cells such that a remaining plurality of cells is diverted into at least one of the one or more bypass channels when the single cell is captured in the capture nest. The one or more bypass channels may include a first bypass channel and a second bypass channel. The first bypass channel and the second bypass channel may be symmetrically configured. The symmetrically configured first bypass channel and second bypass channel may include a first wing configuration and a second wing configuration.

In some embodiments, at least the input channel or the output channel is further configured as a focusing channel. The focusing channel may include a narrowing channel in at least a horizontal direction or a vertical direction. The plurality of multi-chamber reaction configurations may be further configured for thermal cycling while one or more valves of a respective multi-chamber reaction configuration may be actuated.

Some embodiments include one or more imaging features, wherein each respective imaging feature allows for imaging of captured single cells at a respective capture nest site. Some embodiments a plurality of harvest wells, wherein each respective harvest well is coupled with a respective multi-chamber reaction configuration and configured to deliver reaction products for further analysis.

Some embodiments further include a genomic analysis configuration coupled with each respective multi-chamber reaction configuration to further analyze the reaction products from each respective multi-chamber reaction configuration.

In some embodiments, each respective capture configuration includes a capture chamber configured to capture a single cell from a limiting dilution. In some embodiments, each capture chamber is configured to capture a single cell utilizing a stochastic capture process.

In some embodiments, each respective capture configuration includes: a capture compartment; and/or a binding partner covering a discrete region of the capture compartment, where the discrete portion is sized so that only a single cell binds to the discrete region. Some embodiments include one or more capture supports, wherein each capture support comprises a binding partner distributed over at least a portion of the capture support. The one or more capture supports may include one or more bead structures. Some embodiments include a capture feature configured to capture the one or more capture supports.

Some embodiments include a method for multiple single-cell capturing and processing using microfluidics. The method may include: loading a plurality of cells into a microfluidic device; flowing the plurality of cells to a first capture configuration of the microfluidic device; capturing a first single cell from the plurality of cells in the first capture configuration; flowing a first remaining plurality of cells from the plurality of cells to a second capture configuration of the microfluidic device; capturing a second single cell from the first remaining plurality of cells in the second capture configuration; and/or performing multistage processing of at least the first captured single cell and the second captured single cell to produce respective harvest products with respect to at least the first captured single cell and the second captured single cell on the microfluidic device.

Capturing at least the first single cell or the second single cell may include capturing at least the first single cell or the second single cell utilizing one or more a physical barriers sized to hold only a single cell. Some embodiments include flowing the first remaining plurality of cells from the plurality of cells through one or more bypass channels of the first capture configuration to a flow channel coupled with a second capture configuration coupled with the first output channel of the first capture configuration. Some embodiment include flowing a second remaining plurality of cells from the first remaining plurality of cells through one or more second bypass channels to an outlet of the second capture configuration to a third capture configuration through the second output channel.

In some embodiments, the first capture configuration includes: one or more bypass channels coupled with a first input channel and a first output channel; a first drain coupled with the first input channel and the first output channel; and/or a first capture nest coupled with the first drain and configured to capture an individual cell from the plurality of cells. The second capture configuration may include: a plurality of bypass channels coupled with a second input channel and a second output channel, wherein the second input channel is coupled with the first output channel of the first capture configuration; a second drain coupled with the second input channel and the second output channel; and/or a second capture nest coupled with a second drain configured to capture an individual cell from the first remaining plurality of cells.

In some embodiments, performing the multistage processing of at least the first captured single cell and the second captured single cell to produce respective harvest products with respect to at least the first captured single cell and the second captured single cell on the microfluidic device includes lysing, on the microfluidic device, each respective individually captured cell to release the one or more constituents of each respective cell. Performing the multistage processing of at least the first captured single cell and the second captured single cell to produce respective harvest products with respect to at least the first captured single cell and the second captured single cell on the microfluidic device may include flowing the one or more constituents of each respective captured cell into a respective multi-chamber reaction configuration of the microfluidic device for further processing. Performing the multistage processing of at least the first captured single cell and the second captured single cell to produce respective harvest products with respect to at least the first captured single cell and the second captured single cell on the microfluidic device may include performing a thermal cycling procedure while flowing the one or more constituents through one or more aspects of a respective multi-chamber reaction configuration of the microfluidic device. Performing the multistage processing of at least the first captured single cell and the second captured single cell to produce respective harvest products with respect to at least the first captured single cell and the second captured single cell on the microfluidic device may include washing, in the microfluidic device, each respective captured cell with one or more reagents. Performing the multistage processing of at least the first captured single cell and the second captured single cell to produce respective harvest products with respect to at least the first captured single cell and the second captured single cell on the microfluidic device may include dosing, in the microfluidic device, each respective captured cell with one or more reagents.

Performing the multistage processing of at least the first captured single cell and the second captured single cell to produce respective harvest products with respect to at least the first captured single cell and the second captured single cell on the microfluidic device may include performing a preamplification process within the microfluidic device. Performing the multistage processing of at least the first captured single cell and the second captured single cell to produce respective harvest products with respect to at least the first captured single cell and the second captured single cell on the microfluidic device may include performing a mRNA sequencing process within the microfluidic device. Performing the multistage processing of at least the first captured single cell and the second captured single cell to produce respective harvest products with respect to at least the first captured single cell and the second captured single cell on the microfluidic device may include performing at least a specific target amplification, a whole genome amplification, a whole transcriptome amplification, a real-time PCR preparation, a copy number variation, or a haplotyping within the microfluidic device. Performing the multistage processing of at least the first captured single cell and the second captured single cell to produce respective harvest products with respect to at least the first captured single cell and the second captured single cell on the microfluidic device may include marking reaction products from the further processing associated with respective captured cells for identification purposes.

Some embodiments include harvesting the harvest products from a plurality of harvest wells of the microfluidic device. Some embodiments include processing the harvest products. Some embodiments include imaging at least the respective captured cells or the harvest products within the microfluidic device.

In some embodiments, capturing at least the first single cell or the second single cell includes capturing at least the first single cell or the second single cell utilizing a capture chamber configured to capture a single cell from a limiting dilution. Capturing at least the first single cell or the second single cell may include capturing at least the first single cell or the second single cell utilizing a stochastic capture process. Capturing at least the first single cell or the second single cell may include: capturing at least the first single cell or the second single cell utilizing: a capture compartment; and/or a binding partner covering a discrete region of the capture compartment, where the discrete portion is sized so that only a single cell binds to the discrete region. Capturing at least the first single cell or the second single cell may include: capturing at least the first single cell or the second single cell utilizing one or more capture supports, wherein each capture support comprises a binding partner distributed over at least a portion of the capture support. The one or more capture supports may include one or more bead structures. Some embodiments further include a capture feature configured to capture the capture support.

Some embodiments include a method of preamplification utilizing a microfluidic device configured to capture and to process individual cells from a plurality of cells. The method may include: priming the microfluidic device utilizing one or more solutions; flowing the plurality of cells through the microfluidic device such that individual cells from the plurality of cells are capture at individual capture sites of the microfluidic device; lysing the plurality of captured individual cells at the individual capture sites of the microfluidic device; performing reverse transcription, within the microfluidic device, on the plurality of individual lysed cells to produce reverse transcription products associated with each respective individual cell; and/or performing preamplification, within the microfluidic device, on the respective reverse transcription products associated with each respectively lysed individual cell to produce preamplification products associated with each individual capture cell.

Some embodiments include delivering the preamplification products associated with each individual capture cell to a respective harvest inlet from a plurality of harvest inlets of the microfluidic device. Some embodiments include loading the one or more solutions into the microfluidic device. In some embodiments, the one or more solutions include at least one or more reagents or one or more buffers.

Some embodiments include loading the plurality of cells into the microfluidic device. Some embodiments include imaging one or more of the captured individual cells on the microfluidic device. Some embodiments include loading at least one or more lysis reagents, one or more reverse transcription reagents, or one or more preamplification reagents into the microfluidic device. Some embodiments include: removing one or more protective layers of one or more harvesting inlets; and/or harvesting the preamplification products from each respective harvest inlet from the plurality of harvest inlets of the microfluidic device.

Some embodiments include staining the one or more individual capture cells on the microfluidic device. Some embodiments include determining whether the one or more individual captured cells are alive or dead based on the staining. Some embodiments include determining whether the one or more individual captured cells are alive or dead based on the imaging.

In some embodiments, the microfluidic device utilized includes a plurality of capture configurations coupled in series, each respective capture configuration that include: a plurality of bypass channels coupled with an input channel and an output channel; a drain coupled with the input channel and the output channel; and/or a capture nest situated proximal to a junction of the input channel and the plurality of bypass channels and coupled with the drain, wherein the capture nest is configured to capture an individual cell from the plurality of cells such that a remaining plurality of cells is diverted into at least one of the plurality of bypass channels when the individual cell is captured in the capture nest, wherein the capture nest comprises one of the individual capture sites. The microfluidic device may also include a plurality of multi-chamber reaction configurations, wherein each respective multi-chamber reaction configuration is coupled with a respective capture configuration from the plurality of capture configurations and configured for single-cell processing.

Some embodiments include a method of preamplification utilizing a microfluidic device configured to capture and to process individual cells from a plurality of cells. The method may include: loading one or more solutions into the microfluidic device; priming the microfluidic device utilizing the one or more solutions; loading the plurality of cells into the microfluidic device; flowing the plurality of cells through the microfluidic device such that individual cells from the plurality of cells are capture at individual capture sites of the microfluidic device; imaging one or more of the captured individual cells on the microfluidic device; loading at least one or more lysis reagents, one or more reverse transcription reagents, or one or more preamplification reagents into the microfluidic device; lysing the plurality of captured individual cells at the individual capture sites of the microfluidic device; performing reverse transcription, within the microfluidic device, on the plurality of individual lysed cells to produce reverse transcription products associated with each respective individual cell; performing preamplification, within the microfluidic device, on the respective reverse transcription products associated with each respectively lysed individual cell to produce preamplification products associated with each individual capture cell; delivering the preamplification products associated with each individual capture cell to a respective harvest inlet from a plurality of harvest inlets of the microfluidic device; removing one or more protective layers of one or more harvesting inlets; and/or harvesting the preamplification products from each respective harvest inlet from the plurality of harvest inlets of the microfluidic device.

Some embodiments include a method of mRNA sequencing utilizing a microfluidic device configured to capture and to process individual cells from a plurality of cells. The method may include: priming the microfluidic device utilizing one or more solutions; flowing the plurality of cells through the microfluidic device such that individual cells from the plurality of cells are capture at individual capture sites of the microfluidic device; lysing the plurality of captured individual cells at the individual capture sites of the microfluidic device; performing reverse transcription, within the microfluidic device, on the plurality of individual lysed cells to produce reverse transcription products associated with each respective individual cell; and/or performing PCR, within the microfluidic device, on the respective reverse transcription products associated with each respectively lysed individual cell to produce PCR products associated with each individual capture cell.

Some embodiments include delivering the PCR products associated with each individual capture cell to a respective harvest inlet from a plurality of harvest inlets of the microfluidic device. Some embodiments include loading the one or more solutions into the microfluidic device. The one or more solutions may include at least one or more reagents or one or more buffers.

Some embodiments include loading the plurality of cells into the microfluidic device. Some embodiments include imaging one or more of the captured individual cells on the microfluidic device. Some embodiments include loading at least one or more lysis reagents, one or more reverse transcription reagents, or one or more PCR reagents into the microfluidic device. Some embodiments include: removing one or more protective layers of one or more harvesting inlets; and/or harvesting the PCR products from each respective harvest inlet from the plurality of harvest inlets of the microfluidic device.

Some embodiments include staining the one or more individual capture cells on the microfluidic device. Some embodiments include determining whether the one or more individual captured cells are alive or dead based on the staining. Some embodiments include determining whether the one or more individual captured cells are alive or dead based on the imaging. In some embodiments, the PCR products include amplified cDNA.

Some embodiments include preparing one or more libraries utilizing the PCR products associated with each individual captured cell. Preparing the one or more libraries may include: determining a cDNA concentration from each respective harvest products associated with each individual cell; and/or diluting each respective cDNA concentration to within a pre-determined concentration range.

Some embodiments include preparing the dilated cDNA concentration for tagmentation to produce tagmentation products. Some embodiments include performing PCR amplification on the tagmentation products to produce PCR products. Some embodiments include generating one or more library pools from the PCR products.

In some embodiments, the microfluidic device utilized includes a plurality of capture configurations coupled in series, each respective capture configuration that include: a plurality of bypass channels coupled with an input channel and an output channel; a drain coupled with the input channel and the output channel; and/or a capture nest situated proximal to a junction of the input channel and the plurality of bypass channels and coupled with the drain, wherein the capture nest is configured to capture an individual cell from the plurality of cells such that a remaining plurality of cells is diverted into at least one of the plurality of bypass channels when the individual cell is captured in the capture nest, wherein the capture nest comprises one of the individual capture sites. The microfluidic device may also include a plurality of multi-chamber reaction configurations, wherein each respective multi-chamber reaction configuration is coupled with a respective capture configuration from the plurality of capture configurations and configured for single-cell processing.

Some embodiments include a method of mRNA sequencing utilizing a microfluidic device configured to capture and to process individual cells from a plurality of cells. The method may include: loading one or more solutions into the microfluidic device; priming the microfluidic device utilizing the one or more solutions; loading the plurality of cells into the microfluidic device; flowing the plurality of cells through the microfluidic device such that individual cells from the plurality of cells are capture at individual capture sites of the microfluidic device; imaging one or more of the captured individual cells on the microfluidic device; loading at least one or more lysis reagents, one or more reverse transcription reagents, or one or more PCR reagents into the microfluidic device; lysing the plurality of captured individual cells at the individual capture sites of the microfluidic device; performing reverse transcription, within the microfluidic device, on the plurality of individual lysed cells to produce reverse transcription products associated with each respective individual cell; performing PCR, within the microfluidic device, on the respective reverse transcription products associated with each respectively lysed individual cell to produce PCR products associated with each individual capture cell; delivering the PCR products associated with each individual capture cell to a respective harvest inlet from a plurality of harvest inlets of the microfluidic device; removing one or more protective layers of one or more harvesting inlets; and/or harvesting the PCR products from each respective harvest inlet from the plurality of harvest inlets of the microfluidic device.

Some embodiments include microfluidic controller configured for multiple single-cell processing using a microfluidic device. The microfluidic controller may include: a housing; a microfluidic device input and output module configured to load and unload the microfluidic device into the housing; a pressure module configured to couple with the microfluidic device to provide controller pressure to the microfluidic device; a sealing module configured to provide one or more pressure seals to the microfluidic device; and/or a thermal cycling module configured to thermal cycle the microfluidic device.

Some embodiments include an imaging module configured to image one or more aspects of the microfluidic device. The imaging module may include at least a microscope or a camera configured to image one or more captured cells in the microfluidic device. The imaging module may include at least a microscope or a camera configured to image one or more reaction products in the microfluidic device. In some embodiments, the thermal cycling module is configured to thermal cycle the microfluidic device while the pressure module activates one or more valves within the microfluidic device.

Some embodiments include an input module configured to receive input from a user of the microfluidic controller. Some embodiments include a display module configured to at least provide information to a user of the microfluidic controller or receive input from the user of the microfluidic controller.

In some embodiments, the pressure module configured to couple with the microfluidic device to provide controller pressure to the microfluidic device is configured to control pressure in the microfluidic device to flow a plurality of cells through the microfluidic device and to capture individual cells at individual capture configurations within the microfluidic device. The pressure module configured to couple with the microfluidic device to provide controller pressure to the microfluidic device may be configured to control pressure in the microfluidic device to perform multistage processing of multiple single cells captured within the microfluidic device.

In some embodiments, the thermal cycling module configured to thermal cycle the microfluidic device is configured to perform the multistage processing of multiple single cells captured within the microfluidic device.

In some embodiments, the multistage processing comprises preamplification processing. The multistage processing may include mRNA sequence processing.

In some embodiments, the pressure module configured to couple with the microfluidic device to provide controller pressure to the microfluidic device is configured to control pressure in the microfluidic device to prime the microfluidic device. The pressure module configured to couple with the microfluidic device to provide controller pressure to the microfluidic device may be configured to control pressure in the microfluidic device to load a plurality of cells into the microfluidic device and to capture multiple individual cells from the plurality of cells in the microfluidic device.

In some embodiments, at least the pressure module or the thermal cycling module is configured to facilitate to perform at least lysis, reverse transcription, PCR, or harvesting on the microfluidic device. In some embodiments, at least the pressure module or the thermal cycling module is configured to facilitate to perform at least lysis, reverse transcription, preamplification, or harvesting on the microfluidic device.

Some embodiments include a microfluidic device configured for multiple single-cell processing. The microfluidic device may include multiple capture configurations coupled in series. Each respective capture configuration may include: multiple bypass channels coupled with an input channel and an output channel; a drain coupled with the input channel and the output channel; and/or a capture nest situated proximal to a junction of the input channel and the multiple bypass channels and coupled with the drain. The capture nest may be configured to capture an individual cell from multiple cells such that the remaining cells is diverted into at least one of the multiple bypass channels when the individual cell is captured in the capture nest. The microfluidic device may include multiple multi-chamber reaction configurations. Each respective multi-chamber reaction configuration may be coupled with a respective capture configuration from the multiple capture configurations and configured for single-cell processing.

In some embodiments, at least the input channel or the output channel is further configured as a focusing channel. The focusing channel may include a narrowing channel in at least a horizontal direction or a vertical direction. In some embodiments, the multiple bypass channels are symmetrically configured. In some embodiments, the multi-chamber reaction configurations are further configured for thermal cycling while one or more valves of a respective multi-chamber reaction configuration are actuated. In some embodiments, the microfluidic device is further configured for imaging.

Some embodiments include method for multiple single-cell processing using microfluidics. The method may include: loading multiple cells into a microfluidic device; and/or flowing the multiple cells into at least a first capture configuration of the microfluidic device. The first capture configuration may include: multiple first bypass channels coupled with a first input channel and a first output channel; a first drain coupled with the first input channel and the first output channel; and/or a first capture nest coupled with the first drain and configured to capture an individual cell from the multiple cells. The method may include: capturing a first individual cell from the multiple cells at the first capture nest; flowing a first remaining set of cells from the multiple cells through at least one of the multiple first bypass channels to at least a second capture configuration coupled with the first output channel of the first capture configuration; and/or flowing the first remaining set of cells into at least the second capture configuration of the microfluidic device. The second capture configuration may include: multiple second bypass channels coupled with a second input channel and a second output channel, where the second input channel is coupled with the first output channel of the first capture configuration; a second drain coupled with the second input channel and the second output channel; and/or a second capture nest coupled with a second drain configured to capture an individual cell from the first remaining set of cells. The method may include: capturing a second particle or cell from the first remaining set cells at the second capture nest; and flowing a second remaining set of cells from the first remaining set of cells through at least one of the multiple second bypass channels to a third capture configuration through the second output channel.

In some embodiments, the method further includes lysing each respective individually captured cell to release the one or more constituents of each respective cell. The method may further include flowing the one or more constituents of each respective captured cell into a respective multi-chamber reaction configuration for further processing. The method may further include performing a thermal cycling procedure while flowing the one or more constituents through one or more aspects of a respective multi-chamber reaction configuration. The method may further include washing respective captured cells with one or more reagents. The method may further include dosing respective captured cells with one or more agents. The method may further include imaging the respective captured cells.

In some embodiments, the further processing of the method may include performing at least specific target amplification, whole genome amplification, whole transcriptome amplification, real-time PCR preparation, or haplotyping. The method may include marking reaction products from the further processing associated with respective captured cells for identification purposes. The reaction products may be exported and analyzed in a downstream system, for example.

Some embodiments may include a microfluidic controller configured for multiple single-cell processing using a microfluidic device. The microfluidic controller may include: a housing; a microfluidic device input and output module configured to load and unload the microfluidic device into the housing; a pressure module configured to couple with the microfluidic device to provide controller pressure to the microfluidic device; a sealing module configured to provide one or more pressure seals to the microfluidic device; and/or a thermal cycling module configured to thermal cycle the microfluidic device.

In some embodiments, the microfluidic controller includes an imaging module configured to image one or more aspects of the microfluidic device. In some embodiments, the thermal cycling module is configured to thermal cycle the microfluidic device while the pressure module activates one or more valves within the microfluidic device. The microfluidic controller may include an input module configured to receive input from a user of the microfluidic controller. The microfluidic controller may include a display module configured to at least provide information to a user of the microfluidic controller or receive input from the user of the microfluidic controller.

Some embodiments include a microfluidic system configured for multiple single-cell processing. The microfluidic system may include a microfluidic device and/or a microfluidic controller coupled with the microfluidic device. The microfluidic device may include multiple capture configurations coupled in series. Each respective capture configuration may include: multiple bypass channels coupled with an input channel and an output channel; a drain coupled with the input channel and the output channel; and/or a capture nest situated proximal to a junction of the input channel and the multiple bypass channels and coupled with the drain. The capture nest may be configured to capture an individual cell from multiple cells such that the remaining cells is diverted into at least one of the multiple bypass channels when the individual cell is captured in the capture nest. The microfluidic device may include multiple multi-chamber reaction configurations. Each respective multi-chamber reaction configuration may be coupled with a respective capture configuration from the multiple capture configurations and configured for single-cell processing. The microfluidic controller may include: a housing; a microfluidic device input and output module configured to load and unload the microfluidic device into the housing; a pressure module configured to couple with the microfluidic device to provide controller pressure to the microfluidic device; a sealing module configured to provide one or more pressure seals to the microfluidic device; and/or a thermal cycling module configured to thermal cycle the microfluidic device.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the disclosure may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
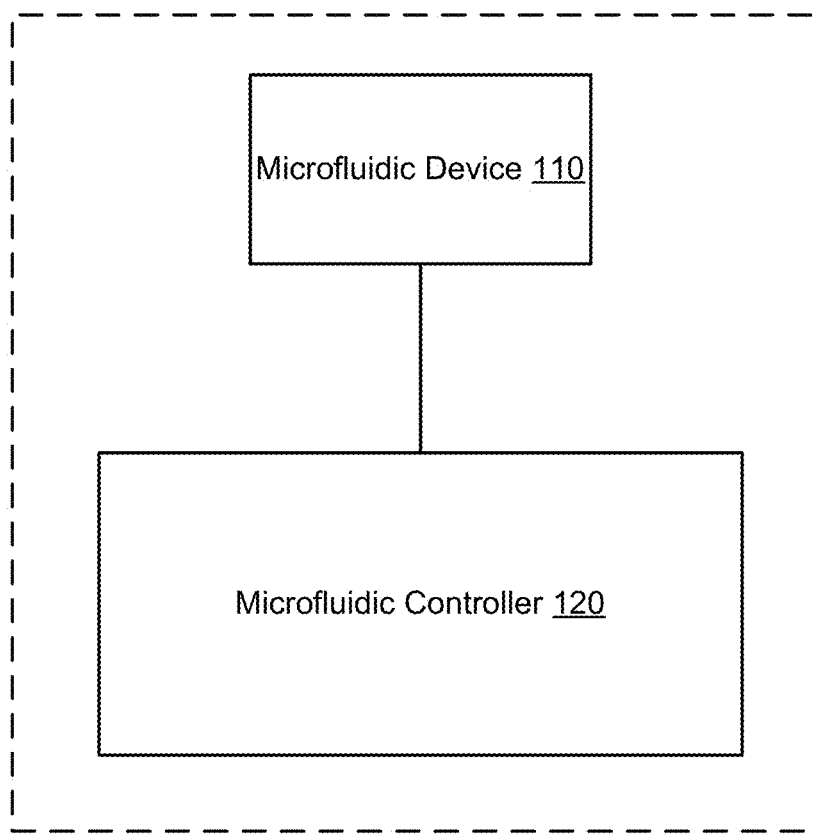
FIG. 1 shows a diagram of a microfluidic system in accordance with various embodiments.

Methods, systems, and devices are described for multiple single-cell capturing and processing utilizing microfluidics. Some embodiments provide for capturing, partitioning, and/or manipulating individual cells from a larger population of cells along with generating genetic information and/or reaction products related to each individual cell. Some embodiments may provide for specific target amplification (STA), whole genome amplification (WGA), whole transcriptome amplification (WTA), real-time PCR preparation, and/or haplotyping of multiple individual cells that have been partitioned from a larger population of cells. Some embodiments provide for other applications. Some specific embodiments provide for mRNA sequencing or preamplification of the multiple individual cells, for example. Some embodiments may be configured for imaging the individual cells or associated reaction products as part of the processing. Reaction products may be harvest and/or further analyzed in some cases.

The methods, systems, and devices may include different microfluidic devices and/or controllers for multiple single-cell capturing and processing utilizing microfluidics. Some microfluidic devices are provided that may include multiple capture configurations and multiple multi-chamber reaction configurations. Each capture configuration may be configured to capture an individual cell from multiple cells. Each multi-chamber reaction configuration may then be utilized to process each cell after it has by lysed. Reactions products may be harvest from each multi-chamber reaction configuration. Microfluidic controllers are also provided that may be utilized to operate the microfluidic device to capture and to process individual cells from multiple cells.

Further aspects of different embodiments may utilize aspects as described in the following sections: (I) microfluidic systems, (II) physical structures of fluid networks, (III) particles, (IV) input mechanisms, (V) positioning mechanisms, (VI) retention mechanisms, (VII) treatment mechanisms, (VIII) measurement mechanisms, (IX) release mechanisms, (X) output mechanisms, (XI) cell culture mechanisms, (XII) particle-based manipulations, and/or (XIII) embodiments.

(I) MICROFLUIDIC SYSTEMS

Particle, such as cell, manipulations and analyses are performed in microfluidic systems. A microfluidic system generally comprises any system in which very small volumes of fluid are stored and manipulated, generally less than about 500 µL, typically less than about 100 µL, and more typically less than about 10 µL. Microfluidic systems carry fluid in predefined paths through one or more microfluidic passages. A microfluidic passage may have a minimum dimension, generally height or width, of less than about 200, 100, or 50 µm. Passages are described in more detail below in Section II.

Microfluidic systems may include one or more sets of passages that interconnect to form a generally closed microfluidic network. Such a microfluidic network may include one, two, or more openings at network termini, or intermediate to the network, that interface with the external world. Such openings may receive, store, and/or dispense fluid. Dispensing fluid may be directly into the microfluidic network or to sites external the microfluidic system. Such openings generally function in input and/or output mechanisms, described in more detail in Sections IV and X below, and may include reservoirs, described in more detail in Section II below.

Microfluidic systems also may include any other suitable features or mechanisms that contribute to fluid, reagent, and/or particle manipulation or analysis. For example, microfluidic systems may include regulatory or control mechanisms that determine aspects of fluid flow rate and/or path. Valves and/or pumps that may participate in such regulatory mechanisms are described in more detail below in Section II. Alternatively, or in addition, microfluidic systems may include mechanisms that determine, regulate, and/or sense fluid temperature, fluid pressure, fluid flow rate, exposure to light, exposure to electric fields, magnetic field strength, and/or the like. Accordingly, microfluidic systems may include heaters, coolers, electrodes, lenses, gratings, light sources, pressure sensors, pressure transducers, microprocessors, microelectronics, and/or so on. Furthermore, each microfluidic system may include one or more features that act as a code to identify a given system. The features may include any detectable shape or symbol, or set of shapes or symbols, such as black-and-white or colored barcode, a word, a number, and/or the like, that has a distinctive position, identity, and/or other property (such as optical property).

Microfluidic systems may be formed of any suitable material or combination of suitable materials. Suitable materials may include elastomers, such as polydimethylsiloxane (PDMS); plastics, such as polystyrene, polypropylene, polycarbonate, etc.; glass; ceramics; sol-gels; silicon and/or other metalloids; metals or metal oxides; biological polymers, mixtures, and/or particles, such as proteins (gelatin, polylysine, serum albumin, collagen, etc.), nucleic acids, microorganisms, etc.; and/or the like.

Exemplary materials for microfluidic systems are described in more detail in the patent applications listed above under Cross-References, which are incorporated herein by reference.

Microfluidic systems, also referred to as chips, may have any suitable structure. Such systems may be fabricated as a unitary structure from a single component, or as a multi-component structure of two or more components. The two or more components may have any suitable relative spatial relationship and may be attached to one another by any suitable bonding mechanism.

In some embodiments, two or more of the components may be fabricated as relatively thin layers, which may be disposed face-to-face. The relatively thin layers may have distinct thickness, based on function. For example, the thickness of some layers may be about 10 to 250 µm, 20 to 200 µm, or about 50 to 150 µm, among others. Other layers may be substantially thicker, in some cases providing mechanical strength to the system. The thicknesses of such other layers may be about 0.25 to 2 cm, 0.4 to 1.5 cm, or 0.5 to 1 cm, among others. One or more additional layers may be a substantially planar layer that functions as a substrate layer, in some cases contributing a floor portion to some or all microfluidic passages.

Components of a microfluidic system may be fabricated by any suitable mechanism, based on the desired application for the system and on materials used in fabrication. For example, one or more components may be molded, stamped, and/or embossed using a suitable mold. Such a mold may be formed of any suitable material by micromachining, etching, soft lithography, material deposition, cutting, and/or punching, among others. Alternatively, or in addition, components of a microfluidic system may be fabricated without a mold by etching, micromachining, cutting, punching, and/or material deposition.

Microfluidic components may be fabricated separately, joined, and further modified as appropriate. For example, when fabricated as distinct layers, microfluidic components may be bonded, generally face-to-face. These separate components may be surface-treated, for example, with reactive chemicals to modify surface chemistry, with particle binding agents, with reagents to facilitate analysis, and/or so on. Such surface-treatment may be localized to discrete portions of the surface or may be relatively nonlocalized. In some embodiments, separate layers may be fabricated and then punched and/or cut to produce additional structure. Such punching and/or cutting may be performed before and/or after distinct components have been joined.

Exemplary methods for fabricating microfluidic systems are described in more detail in the patent applications identified above under Cross-References, which are incorporated herein by reference.

(II) PHYSICAL STRUCTURES OF FLUID NETWORKS

Microfluidic systems may include any suitable structure (s) for the integrated manipulation of small volumes of fluid, including moving and/or storing fluid, and particles associated therewith, for use in particle assays. The structures may include passages, reservoirs, and/or regulators, among others.

Passages generally comprise any suitable path, channel, or duct through, over, or along which materials (e.g., fluid, particles, and/or reagents) may pass in a microfluidic system. Collectively, a set of fluidically communicating passages, generally in the form of channels, may be referred to as a microfluidic network. In some cases, passages may be described as having surfaces that form a floor, a roof, and walls. Passages may have any suitable dimensions and geometry, including width, height, length, and/or cross-sectional profile, among others, and may follow any suitable path, including linear, circular, and/or curvilinear, among others. Passages also may have any suitable surface contours, including recesses, protrusions, and/or apertures, and may have any suitable surface chemistry or permeability at any appropriate position within a channel. Suitable surface chemistry may include surface modification, by addition and/or treatment with a chemical and/or reagent, before, during, and/or after passage formation.

In some cases, passages, and particularly channels, may be described according to function. For example, passages may be described according to direction of material flow in a particular application, relationship to a particular reference structure, and/or type of material carried. Accordingly, passages may be inlet passages (or channels), which generally carry materials to a site, and outlet passages (or channels), which generally carry materials from a site. In addition, passages may be referred to as particle passages (or channels), reagent passages (or channels), focusing passages (or channels), perfusion passages (or channels), waste passages (or channels), and/or the like.

Passages may branch, join, and/or dead-end to form any suitable microfluidic network. Accordingly, passages may function in particle positioning, sorting, retention, treatment, detection, propagation, storage, mixing, and/or release, among others.

Reservoirs generally comprise any suitable receptacle or chamber for storing materials (e.g., fluid, particles and/or reagents), before, during, between, and/or after processing operations (e.g., measurement and/or treatment). Reservoirs, also referred to as wells, may include input, intermediate, and/or output reservoirs. Input reservoirs may store materials (e.g., fluid, particles, and/or reagents) prior to inputting the materials to a microfluidic network(s) portion of a chip. By contrast, intermediate reservoirs may store materials during and/or between processing operations. Finally, output reservoirs may store materials prior to outputting from the chip, for example, to an external processor or waste, or prior to disposal of the chip.

Further aspects of reservoirs are included in the patent applications identified above under Cross-References, which are incorporated herein by reference.

Regulators generally comprise any suitable mechanism for generating and/or regulating movement of materials (e.g., fluid, particles, and/or reagents). Suitable regulators may include valves, pumps, and/or electrodes, among others. Regulators may operate by actively promoting flow and/or by restricting active or passive flow. Suitable functions mediated by regulators may include mixing, sorting, connection (or isolation) of fluidic networks, and/or the like.

(III) PARTICLES

Microfluidic systems may be used to manipulate and/or analyze particles. A particle generally comprises any object that is small enough to be inputted and manipulated within a microfluidic network in association with fluid, but that is large enough to be distinguishable from the fluid. Particles, as used here, typically are microscopic or near-microscopic, and may have diameters of about 0.005 to 100 µm, 0.1 to 50 µm, or about 0.5 to 30 µm. Alternatively, or in addition, particles may have masses of about $10^{-20}$ to $10^{-5}$ grams, $10^{-16}$ to $10^{-7}$ grams, or $10^{-14}$ to $10^{-8}$ grams. Exemplary particles may include cells, viruses, organelles, beads, and/or vesicles, and aggregates thereof, such as dimers, trimers, etc.

One example of particles is cells. Cells, as used here, generally comprise any self-replicating, membrane-bounded biological entity, or any nonreplicating, membrane-bounded descendant thereof. Nonreplicating descendants may be senescent cells, terminally differentiated cells, cell chimeras, serum-starved cells, infected cells, nonreplicating mutants, anucleate cells, etc.

Cells used as particles in microfluidic systems may have any suitable origin, genetic background, state of health, state of fixation, membrane permeability, pretreatment, and/or population purity, among others. Origin of cells may be eukaryotic, prokaryotic, archae, etc., and may be from animals, plants, fungi, protists, bacteria, and/or the like. Cells may be wild-type; natural, chemical, or viral mutants; engineered mutants (such as transgenics); and/or the like. In addition, cells may be growing, quiescent, senescent, transformed, and/or immortalized, among others, and cells may be fixed and/or unfixed. Living or dead, fixed or unfixed cells may have intact membranes, and/or permeabilized/disrupted membranes to allow uptake of ions, labels, dyes, ligands, etc., or to allow release of cell contents. Cells may have been pretreated before introduction into a microfluidic system by any suitable processing steps. Such processing steps may include modulator treatment, transfection (including infection, injection, particle bombardment, lipofection, coprecipitate transfection, etc.), processing with assay reagents, such as dyes or labels, and/or so on. Furthermore, cells may be a monoculture, generally derived as a clonal population from a single cell or a small set of very similar cells; may be presorted by any suitable mechanism such as affinity binding, FACS, drug selection, etc.; and/or may be a mixed or heterogeneous population of distinct cell types.

Eukaryotic cells, that is, cells having one or more nuclei, or anucleate derivatives thereof, may be obtained from any suitable source, including primary cells, established cells, and/or patient samples. Such cells may be from any cell type or mixture of cell types, from any developmental stage, and/or from any genetic background. Furthermore, eukaryotic cells may be adherent and/or nonadherent. Such cells may be from any suitable eukaryotic organism including animals, plants, fungi, and/or protists.

Eukaryotic cells may be from animals, that is, vertebrates or invertebrates. Vertebrates may include mammals, that is, primates (such as humans, apes, monkeys, etc.) or nonprimates (such as cows, horses, sheep, pigs, dogs, cats, marsupials, rodents, and/or the like). Nonmammalian vertebrates may include birds, reptiles, fish, (such as trout, salmon, goldfish, zebrafish, etc.), and/or amphibians (such as frogs of the species *Xenopus, Rana*, etc.). Invertebrates may include arthropods (such as arachnids, insects (e.g., *Drosophila*), etc.), mollusks (such as clams, snails, etc.), annelids (such as earthworms, etc.), echinoderms (such as various starfish, among others), coelenterates (such as jellyfish, coral, etc.), porifera (sponges), platyhelminths (tapeworms), nemathelminths (flatworms), etc.

Eukaryotic cells may be from any suitable plant, such as monocotyledons, dicotyledons, gymnosperms, angiosperms, ferns, mosses, lichens, and/or algae, among others. Exemplary plants may include plant crops (such as rice, corn, wheat, rye, barley, potatoes, etc.), plants used in research (e.g., *Arabadopsis*, loblolly pine, etc.), plants of horticultural values (ornamental palms, roses, etc.), and/or the like.

Eukaryotic cells may be from any suitable fungi, including members of the phyla Chytridiomycota, Zygomycota, Ascomycota, Basidiomycota, Deuteromycetes, and/or yeasts. Exemplary fungi may include *Saccharomyces cerevisiae, Schizosaccharomyces pombe, Pichia pastoralis, Neurospora crassa*, mushrooms, puffballs, imperfect fungi, molds, and/or the like.

Eukaryotic cells may be from any suitable protists (protozoans), including amoebae, ciliates, flagellates, coccidia, microsporidia, and/or the like. Exemplary protists may include *Giardia lamblia, Entamoeba. histolytica, Cryptosporidium*, and/or *N. fowleri*, among others.

Particles may include eukaryotic cells that are primary, that is, taken directly from an organism or nature, without subsequent extended culture in vitro. For example, the cells may be obtained from a patient sample, such as whole blood, packed cells, white blood cells, urine, sputum, feces, mucus, spinal fluid, tumors, diseased tissue, bone marrow, lymph, semen, pleural fluid, a prenatal sample, an aspirate, a biopsy, disaggregated tissue, epidermal cells, keratinocytes, endothelial cells, smooth muscle cells, skeletal muscle cells, neural cells, renal cells, prostate cells, liver cells, stem cells, osteoblasts, and/or the like. Similar samples may be manipulated and analyzed from human volunteers, selected members of the human population, forensic samples, animals, plants, and/or natural sources (water, soil, air, etc.), among others.

Alternatively, or in addition, particles may include established eukaryotic cells. Such cells may be immortalized and/or transformed by any suitable treatment, including viral infection, nucleic acid transfection, chemical treatment, extended passage and selection, radiation exposure, and/or the like. Such established cells may include various lineages such as neuroblasts, neurons, fibroblasts, myoblasts, myotubes, chondroblasts, chondrocytes, osteoblasts, osteocytes, cardiocytes, smooth muscle cells, epithelial cells, keratinocytes, kidney cells, liver cells, lymphocytes, granulocytes, and/or macrophages, among others. Exemplary established cell lines may include Rat-1, NIH 3T3, HEK 293, COS 1, COS7, CV-1, C2C12, MDCK, PC12, SAOS, HeLa, Schneider cells, Junkat cells, SL2, and/or the like.

Particles may be prokaryotic cells, that is, self-replicating, membrane-bounded microorganisms that lack membrane-bound organelles, or nonreplicating descendants thereof. Prokaryotic cells may be from any phyla, including Aquificae, Bacteroids, Chlorobia, Chrysogenetes, Cyanobacteria, Fibrobacter, Firmicutes, Flavobacteria, Fusobacteria, Proteobacteria, Sphingobacteria, Spirochaetes, Thermomicrobia, and/or Xenobacteria, among others. Such bacteria may be gram-negative, gram-positive, harmful, beneficial, and/or pathogenic. Exemplary prokaryotic cells may include *E. coli, S. typhimurium, B subtilis, S. aureus, C. perfringens, V. parahaemolyticus*, and/or *B. anthracis*, among others.

Viruses may be manipulated and/or analyzed as particles in microfluidic systems. Viruses generally comprise any microscopic/submicroscopic parasites of cells (animals, plants, fungi, protists, and/or bacteria) that include a protein and/or membrane coat and that are unable to replicate without a host cell. Viruses may include DNA viruses, RNA viruses, retroviruses, virions, viroids, prions, etc. Exemplary viruses may include HIV, RSV, rabies, hepatitis virus, Epstein-Barr virus, rhinoviruses, bacteriophages, prions that cause various diseases (CJD (Creutzfeld-Jacob disease, kuru, GSS (Gerstmann-Straussler-Scheinker syndrome), FFI (Fatal Familial Insomnia), Alpers syndrome, etc.), and/or the like.

Organelles may be manipulated and/or analyzed in microfluidic systems. Organelles generally comprise any particulate component of a cell. For example, organelles may include nuclei, Golgi apparatus, lysosomes, endosomes, mitochondria, peroxisomes, endoplasmic reticulum, phagosomes, vacuoles, chloroplasts, etc.

Particle assays may be performed with beads. Beads generally comprise any suitable manufactured particles. Beads may be manufactured from inorganic materials, or materials that are synthesized chemically, enzymatically and/or biologically. Furthermore, beads may have any suitable porosity and may be formed as a solid or as a gel. Suitable bead compositions may include plastics (e.g., polystyrene), dextrans, glass, ceramics, sol-gels, elastomers, silicon, metals, and/or biopolymers (proteins, nucleic acids, etc.). Beads may have any suitable particle diameter or range of diameters. Accordingly, beads may be a substantially uniform population with a narrow range of diameters, or beads may be a heterogeneous population with a broad range of diameters, or two or more distinct diameters.

Beads may be associated with any suitable materials. The materials may include compounds, polymers, complexes, mixtures, phages, viruses, and/or cells, among others. For example, the beads may be associated with a member of a specific binding pair (see Section VI), such as a receptor, a ligand, a nucleic acid, a member of a compound library, and/or so on. Beads may be a mixture of distinct beads, in some cases carrying distinct materials. The distinct beads may differ in any suitable aspect(s), such as size, shape, an associated code, and/or material carried by the beads. In some embodiments, the aspect may identify the associated material. Codes are described further in Section XII below.

Particles may be vesicles. Vesicles generally comprise any noncellularly derived particle that is defined by a lipid envelope. Vesicles may include any suitable components in their envelope or interior portions. Suitable components may include compounds, polymers, complexes, mixtures, aggregates, and/or particles, among others. Exemplary components may include proteins, peptides, small compounds, drug candidates, receptors, nucleic acids, ligands, and/or the like.

(IV) INPUT MECHANISMS

Microfluidic systems may include one or more input mechanisms that interface with the microfluidic network(s). An input mechanism generally comprises any suitable mechanism for inputting material(s) (e.g., particles, fluid, and/or reagents) to a microfluidic network of a microfluidic chip, including selective (that is, component-by-component) and/or bulk mechanisms.

The input mechanism may receive material from internal sources, that is, reservoirs that are included in a microfluidic chip, and/or external sources, that is, reservoirs that are separate from, or external to, the chip.

Input mechanisms that input materials from internal sources may use any suitable receptacle to store and dispense the materials. Suitable receptacles may include a void formed in the chip. Such voids may be directly accessible from outside the chip, for example, through a hole extending from fluidic communication with a fluid network to an external surface of the chip, such as the top surface. The receptacles may have a fluid capacity that is relatively large compared to the fluid capacity of the fluid network, so that they are not quickly exhausted. For example, the fluid capacity may be at least about 1, 5, 10, 25, 50, or 100 µL. Accordingly, materials may be dispensed into the receptacles using standard laboratory equipment, if desired, such as micropipettes, syringes, and the like.

Input mechanisms that input materials from external sources also may use any suitable receptacle and mechanism to store and dispense the materials. However, if the external sources input materials directly into the fluid network, the external sources may need to interface effectively with the fluid network, for example, using contact and/or noncontact dispensing mechanisms. Accordingly, input mechanisms from external sources may use capillaries or needles to direct fluid precisely into the fluid network. Alternatively, or in addition, input mechanisms from external sources may use a noncontact dispensing mechanism, such as "spitting," which may be comparable to the action of an inkjet printer. Furthermore, input mechanisms from external sources may use ballistic propulsion of particles, for example, as mediated by a gene gun.

The inputting of materials into the microfluidics system may be facilitated and/or regulated using any suitable facilitating mechanism. Such facilitating mechanisms may include gravity flow, for example, when an input reservoir has greater height of fluid than an output reservoir. Facilitating mechanisms also may include positive pressure to push materials into the fluidic network, such as mechanical or gas pressure, or centrifugal force; negative pressure at an output mechanism to draw fluid toward the output mechanism; and/or a positioning mechanism acting within the fluid network. The positioning mechanism may include a pump and/or an electrokinetic mechanism. Positioning mechanisms are further described below, in Section V. In some embodiments, the facilitating mechanism may include a suspension mechanism to maintain particles such as cells in suspension prior to inputting.

(V) POSITIONING MECHANISMS

Microfluidic systems may include one or more positioning mechanisms. A positioning mechanism generally comprises any mechanism for placing particles at preselected positions on the chip after inputting, for example, for retention, growth, treatment, and/or measurement, among others. Positioning mechanisms may be categorized without limitation in various ways, for example, to reflect their origins and/or operational principles, including direct and/or indirect, fluid-mediated and/or non-fluid-mediated, external and/or internal, and so on. These categories are not mutually exclusive. Thus, a given positioning mechanism may position a particle in two or more ways; for example, electric fields may position a particle directly (e.g., via electrophoresis) and indirectly (e.g., via electroosmosis).

The positioning mechanisms may act to define particle position longitudinally and/or transversely. The term "longitudinal position" denotes position parallel to or along the long axis of a microfluidic channel and/or a fluid flow stream within the channel. In contrast, the term "transverse position" denotes position orthogonal to the long axis of a channel and/or an associated main fluid flow stream. Both longitudinal and transverse positions may be defined locally, by equating "long axis" with "tangent" in curved channels.

The positioning mechanisms may be used alone and/or in combination. If used in combination, the mechanisms may be used serially (i.e., sequentially) and/or in parallel (i.e., simultaneously). For example, an indirect mechanism such as fluid flow may be used for rough positioning, and a direct mechanism such as optical tweezers may be used for final positioning (and/or subsequent retention, as described elsewhere).

The remainder of this section describes without limitation a variety of exemplary positioning mechanisms, sorted roughly as direct and indirect mechanisms.

Direct positioning mechanisms generally comprise any mechanisms in which a force acts directly on a particle(s) to position the particle(s) within a microfluidic network. Direct positioning mechanisms may be based on any suitable mechanism, including optical, electrical, magnetic, and/or gravity-based forces, among others. Optical positioning mechanisms use light to mediate or at least facilitate positioning of particles. Suitable optical positioning mechanisms include "optical tweezers," which use an appropriately focused and movable light source to impart a positioning force on particles. Electrical positioning mechanisms use electricity to position particles. Suitable electrical mechanisms include "electrokinesis," that is, the application of voltage and/or current across some or all of a microfluidic network, which may, as mentioned above, move charged particles directly (e.g., via electrophoresis) and/or indirectly, through movement of ions in fluid (e.g., via electroosmosis). Magnetic positioning mechanisms use magnetism to position particles based on magnetic interactions. Suitable magnetic mechanisms involve applying a magnetic field in or around a fluid network, to position particles via their association with ferromagnetic and/or paramagnetic materials in, on, or about the particles. Gravity-based positioning mechanisms use the force of gravity to position particles, for example, to contact adherent cells with a substrate at positions of cell culture.

Indirect positioning mechanisms generally comprise any mechanisms in which a force acts indirectly on a particle(s), for example, via fluid, to move the particle(s) within a microfluidic network, longitudinally and/or transversely.

Longitudinal indirect positioning mechanisms generally may be created and/or regulated by fluid flow along channels and/or other passages. Accordingly, longitudinal positioning mechanisms may be facilitated and/or regulated by valves and/or pumps that regulate flow rate and/or path. In some cases, longitudinal positioning mechanisms may be facilitated and/or regulated by electroosmotic positioning mechanisms. Alternatively, or in addition, longitudinal positioning mechanisms may be input-based, that is, facilitated and/or regulated by input mechanisms, such as pressure or gravity-based mechanisms, including a pressure head created by unequal heights of fluid columns.

Transverse indirect positioning mechanisms generally may be created and/or regulated by fluid flow streams at channel junctions, laterally disposed regions of reduced fluid flow, and/or channel bends. Channel junctions may be unifying sites or dividing sites, based on the number of channels that carry fluid to the sites relative to the number that carry fluid away from the sites. Transverse indirect positioning mechanisms may be based on laminar flow, stochastic partitioning, and/or centrifugal force, among others.

Transverse positioning of particles and/or reagents in a microfluidic system may be mediated at least in part by a laminar flow-based mechanism. Laminar flow-based mechanisms generally comprise any positioning mechanism in which the position of an input flow stream within a channel is determined by the presence, absence, and/or relative position(s) of additional flow streams within the channel. Such laminar flow-based mechanisms may be defined by a channel junction(s) that is a unifying site, at which inlet flow streams from two, three, or more channels, flowing toward the junction, unify to form a smaller number of outlet flow streams, preferably one, flowing away from the junction. Due to the laminar flow properties of flow streams on a microfluidic scale, the unifying site may maintain the relative distribution of inlet flow streams after they unify as laminar outlet flow streams. Accordingly, particles and/or reagents may remain localized to any selected one or more of the laminar flow streams, based on which inlet channels carry particles and/or reagents, thus positioning the particles and/or reagents transversely.

The relative size (or flow rate) and position of each inlet flow stream may determine both transverse position and relative width of flow streams that carry particles and/or reagents. For example, an inlet flow stream for particles/reagents that is relatively small (narrow), flanked by two larger (wider) flow streams, may occupy a narrow central position in a single outlet channel. By contrast, an inlet flow stream for particles/reagents that is relatively large (wide), flanked by a comparably sized flow stream and a smaller (narrower) flow stream, may occupy a wider position that is biased transversely toward the smaller flow stream. In either case, the laminar flow-based mechanism may be called a focusing mechanism, because the particles/reagents are "focused" to a subset of the cross-sectional area of outlet channels. Laminar flow-based mechanisms may be used to individually address particles and/or reagents to plural distinct retention sites.

A laminar flow-based mechanism may be a variable mechanism to vary the transverse position of particles/reagents. As described above, the relative contribution of each inlet flow stream may determine the transverse position of particles/reagents flow streams. Altered flow of any inlet flow stream may vary its contribution to the outlet flow stream(s), shifting particles/reagents flow streams accordingly. In an extreme case, referred to as a perfusion mechanism, a reagent (or particle) flow stream may be moved transversely, either in contact with, or spaced from, retained particles (reagents), based on presence or absence of flow from an adjacent inlet flow stream. Such a mechanism also may be used to effect variable or regulated transverse positioning of particles, for example, to direct particles to retention sites having different transverse positions.

Transverse positioning of particles and/or reagents in a microfluidic system may be mediated at least in part by a stochastic (or portioned flow) positioning mechanism. Stochastic transverse positioning mechanisms generally comprise any positioning mechanism in which an at least partially randomly selected subset of inputted particles or reagent is distributed laterally away from a main flow stream to a region of reduced fluid flow within a channel (or, potentially, to a distinct channel). The region of reduced flow may promote particle retention, treatment, detection, minimize particle damage, and/or promote particle contact with a substrate. Stochastic positioning mechanisms may be determined by dividing flow sites and/or locally widened channels, among others.

Dividing flow sites may effect stochastic positioning by forming regions of reduced fluid flow rate. Dividing flow sites generally include any channel junction at which inlet flow streams from one (preferably) or more inlet channels are divided into a greater number of outlet channels, including two, three, or more, channels. Such dividing sites may deliver a subset of particles, which may be selected stochastically and/or based on a property of the particles (such as mass), to a region of reduced flow rate or quasi-stagnant flow formed at or near the junction. The fraction of particles represented by the subset may be dependent upon the relative flow directions of the outlet channels relative to the inlet channels. These flow directions may be generally orthogonal to an inlet flow stream, being directed in opposite directions, to form a "T-junction." Alternatively, outlet flow directions may form angles of less than and/or greater than 90.degree.

The dividing-flow positioning mechanism, with two or more outlet channels, may be used as a portioned-flow mechanism. Specifically, fluid, particles, and/or reagents carried to the channel junction may be portioned according to fluid flow through the two or more outlet channels. Accordingly, the fractional number or volume of particles or reagent that enters the two or more channels may be regulated by the relative sizes of the channels and/or the flow rate of fluid through the channels, which in turn may be regulated by valves, or other suitable flow regulatory-mechanisms. In a first set of embodiments, outlet channels may be of very unequal sizes, so that only a small fraction of particle and/or reagents are directed to the smaller channel. In a second set of embodiments, valves may be used to forms desired dilutions of reagents. In a third set of embodiments, valves may be used to selectively direct particles to one of two or more fluid paths.

Locally widened channels may promote stochastic positioning by producing regions of decreased flow rate lateral to a main flow stream. The decreased flow rate may deposit a subset of inputted particles at a region of decreased flow rate. Such widened channels may include nonlinear channels that curve or bend at an angle. Alternatively, or in addition, widened regions may be formed by recesses formed in a channel wall(s), chambers that intersect channels, and/or the like, particularly at the outer edge of a curved or bent channel.

Transverse positioning of particles and/or reagents also may be mediated at least in part by a centrifugal positioning mechanism. In centrifugal positioning mechanisms, particles may experience a centrifugal force determined by a change in velocity, for example, by moving through a bend in a fluid path. Size and/or density of particles may determine the rate of velocity change, distributing distinct sizes and/or densities of particle to distinct transverse positions.

(VI) RETENTION MECHANISMS

Microfluidic systems may include one or more retention mechanisms. A retention mechanism generally comprises any suitable mechanism for retaining (or holding, capturing, or trapping) particles at preselected positions or regions of microfluidic networks, including single or plural mechanisms, operating in series and/or in parallel. Retention mechanisms may act to overcome the positioning force exerted by fluid flow. Furthermore, retention mechanisms, also referred to as capture or trapping mechanisms, may retain any suitable number of particles, including single particles or groups/populations of particles. Suitable retention mechanisms may be based on physical barriers coupled with flow, chemical interactions, vacuum forces, fluid flow in a loop, gravity, centrifugal forces, magnetic forces, electrical forces, and/or optically generated forces, among others.

Retention mechanisms may be selective or nonselective. Selective mechanisms may be fractionally selective, that is, retaining less than all (a subset of) inputted particles. Alternatively, or in addition, selective mechanisms may be particle-dependent, that is, retaining particles based on one or more properties of the inputted particle, such as size, surface chemistry, density, magnetic character, electrical charge, optical property (such as refractive index), and/or the like.

Retention mechanisms may be based at least partially on particle contact with any suitable physical barrier(s) disposed in a microfluidic network. Such particle-barrier contact generally restricts longitudinal particle movement along the direction of fluid flow, producing flow-assisted retention. Flow-assisted particle-barrier contact also may restrict side-to-side/orthogonal (transverse) movement. Suitable physical barriers may be formed by protrusions that extend inward from any portion of a channel or other passage (that is, walls, roof, and/or floor). For example, the protrusions may be fixed and/or movable, including columns, posts, blocks, bumps, walls, and/or partially/completely closed valves, among others. Some physical barriers, such as valves, may be movable or regulatable. Alternatively, or in addition, a physical barrier may be defined by a recess(es) formed in a channel or other passage, or by a fluid-permeable membrane. Other physical barriers may be formed based on the cross-sectional dimensions of passages. For example, size-selective channels may retain particles that are too large to enter the channels. (Size-selective channels also may be referred to as filter channels, microchannels, or particle-restrictive or particle-selective channels.)

Further aspects of physical barriers and size-selective channels are described below in Section XIII.

Chemical retention mechanisms may retain particles based on chemical interactions. The chemical interactions may be covalent and/or noncovalent interactions, including ionic, electrostatic, hydrophobic, van der Waals, and/or metal coordination interactions, among others. Chemical interactions may retain particles selectively and/or nonselectively. Selective and nonselective retention may be based on specific and/or nonspecific chemical interactions between particles and passage surfaces.

Chemical interactions may be specific. Specific mechanisms may use specific binding pairs (SBPs), for example, with first and second SBP members disposed on particles and passage surfaces, respectively. Exemplary SBPs may include biotin/avidin, antibody/antigen, lectin/carbohydrate, etc. These and additional exemplary SBPs are listed below in Table 1, with the designations of first and second being arbitrary. SBP members may be disposed locally within microfluidic networks before, during and/or after formation of the networks. For example, surfaces of a substrate and/or a fluid layer component may be locally modified by adhesion/attachment of a SBP member before the substrate and fluid layer component are joined. Alternatively, or in addition, an SBP member may be locally associated with a portion of a microfluidic network after the network has been formed, for example, by local chemical reaction of the SBP member with the network (such as catalyzed by local illumination with light).

Chemical interactions also may be relatively nonspecific. Nonspecific interaction mechanisms may rely on local differences in the surface chemistry of microfluidic networks. Such local references may be created before, during and/or after passage/microfluidic network formation, as described above. The local differences may result from localized chemical reactions, for example, to create hydrophobic or hydrophilic regions, and/or localized binding of materials. The bound materials may include poly-L-lysine, poly-D-lysine, polyethylenimine, albumin, gelatin, collagen, laminin, fibronectin, entactin, vitronectin, fibrillin, elastin, heparin, keratan sulfate, heparan sulfate, chondroitin sulfate, hyaluronic acid, and/or extracellular matrix extracts/mixtures, among others.

Other retention mechanisms may be used alternatively, or in addition to, physical barrier-based and/or chemical interaction-based retention. Some or all of these mechanisms, and/or the mechanisms described above, may rely at least partially on friction between particles and passages to assist retention.

Retention mechanisms may be based on vacuum forces, fluid flow, and/or gravity. Vacuum-based retention mechanisms may exert forces that pull particles into tighter contact with passage surfaces, for example, using a force directed outwardly from a channel. Application of a vacuum, and/or particle retention, may be assisted by an aperture/orifice in the wall of a channel or other passage. By contrast, fluid flow-based retention mechanisms may produce fluid flow paths, such as loops, that retain particles. These fluid flow paths may be formed by a closed channel-circuit having no outlet (e.g., by valve closure and active pumping), and/or by an eddy, such as that produced by generally circular fluid-flow within a recess. Gravity-based retention mechanisms may hold particles against the bottom surfaces of passages, thus combining with friction to restrict particle movement. Gravity-based retention may be facilitated by recesses and/or reduced fluid flow rates.

Retention mechanisms may be based on centrifugal forces, magnetic forces, and/or optically generated forces. Retention mechanisms based on centrifugal force may retain particles by pushing the particle against passage surfaces, typically by exerting a force on the particles that is generally orthogonal to fluid flow. Such forces may be exerted by centrifugation of a microfluidic chip and/or by particle movement within a fluid flow path. Magnetic force-based retention mechanisms may retain particles using magnetic fields, generated external and/or internal to a microfluidic system. The magnetic field may interact with ferromagnetic and/or paramagnetic portions of particles. For example, beads may be formed at least partially of ferromagnetic materials, or cells may include surface-bound or internalized ferromagnetic particles. Electrical force-based retention mechanisms may retain charged particles and/or populations using electrical fields. By contrast, retention mechanisms that operate based on optically generated forces may use light to retain particles. Such mechanisms may operate based on the principal of optical tweezers, among others.

Another form of retention mechanism is a blind-fill channel, where a channel has a inlet, but no outlet, either fixedly or transiently. For example, when the microfluidic device is made from a gas permeable material, such as PDMS, gas present in a dead-end channel can escape, or be forced out of the channel through the gas permeable material when urged out by the inflow of liquid through the inlet. This is a preferred example of blind-filling. Blind-filling can be used with a channel or chamber that has an inlet, and an outlet that is gated or valved by a valve. In this example, blind filling of a gas filled channel or chamber occurs when the outlet valve is closed while filling the channel or chamber through the inlet. If the inlet also has a valve, that valve can then be closed after the blind fill is complete, and the outlet can then be opened to expose the channel or chamber contents to another channel or chamber. If a third inlet is in communication with the channel or chamber, that third inlet can introduce another fluid, gas or liquid, into the channel or chamber to expel the blind-filled liquid to be expelled from the channel or chamber in a measured amount. The result is similar to a sample loop system of an HPLC. Further aspects of Retention Mechanisms are described in Sections V and XIII.

(VII) TREATMENT MECHANISMS

Treatment mechanisms generally comprise any suitable mechanisms for exposing a particle(s) to a reagent(s) and/or a physical condition(s), including fluid-mediated and non-fluid-mediated mechanisms.

Particles may be exposed to reagents. A reagent generally comprises any chemical substance(s), compound(s), ion(s), polymer(s), material(s), complex(es), mixture(s), aggregate(s), and/or biological particle(s), among others, that contacts a particle or particle population in a microfluidic system. Reagents may play a role in particle analysis, including operating as chemical/biological modulators (interaction reagents), detection/assay reagents, solvents, buffers, media, washing solutions, and/or so on.

Chemical modulators or biological modulators may include any reagent that is being tested for interaction with particles. Interaction generally includes specific binding to particles and/or any detectable genotypic and/or phenotypic effect on particles (or modulators). Further aspects of interactions and genotypic/phenotypic effects that may be suitable are described below in Section XII.

Chemical modulators may include ligands that interact with receptors (e.g., antagonists, agonists, hormones, etc.). Ligands may be small compounds, peptides, proteins, carbohydrates, lipids, etc. Further aspects of ligands and receptors, and their use in measuring interaction, or effects on signal transduction pathways, are described below in Section XII.

Alternatively, or in addition, chemical modulators may be nucleic acids. The nucleic acids may be DNA, RNA, peptide nucleic acids, modified nucleic acids, and/or mixtures thereof, and may be single, double, and/or triple-stranded. The nucleic acids may be produced by chemical synthesis, enzymatic synthesis, and/or biosynthesis, and may be plasmids, fragments, sense/antisense expression vectors, reporter genes, vectors for genomic integration/modification (such as targeting nucleic acids/vectors (for knockout-downin)), viral vectors, antisense oligonucleotides, dsRNA, siRNA, nucleozymes, and/or the like. Nucleic acid reagents may also include transfection reagents to promote uptake of the nucleic acids by cells, such as lipid reagents (e.g., lipofectamine), precipitate-forming agents (such as calcium phosphate), DMSO, polyethylene glycol, viral coats that package the nucleic acids, and/or so on.

Modulators may be miscellaneous chemical materials and/or biological entities. Miscellaneous chemical modulators may be ions (such as calcium, sodium, potassium, lithium, hydrogen (pH), chloride, fluoride, iodide, etc.), dissolved gases (NO, $CO_2$, $O_2$, etc.), carbohydrates, lipids, organics, polymers, etc. In some embodiments, biological modulators may be exposed to cells, for example, to infect cells, to measure cell-cell interactions, etc. Biological modulators may include any cells, viruses, or organelles, as described above in Section III.

Reagents may be detection/assay reagents. Detection/assay reagents generally comprise any reagents that are contacted with particles to facilitate processing particles (or particle components) for detection of a preexisting or newly created aspect of the particles (or components). Detection/assay reagents may include dyes, enzymes, substrates, cofactors, and/or SBP members (see Table 1 of Section VI above), among others. Dyes, also referred to as labels, generally include any optically detectable reagent. Suitable dyes may be luminophores, fluorophores, chromogens, chromophores, and/or the like. Such dyes may be conjugated to, or may be, SBP members; may act as enzyme substrates; may inherently label cells or cell structures (e.g., DNA dyes, membrane dyes, trafficking dyes, etc.); may act as indicator dyes (such as calcium indicators, pH indicators, etc.); and/or the like. Enzymes may operate in particle assays by incorporating dyes into products and/or by producing a product that may be detected subsequently with dyes, among others. Suitable enzymes may include polymerases (RNA and/or DNA), heat-stable polymerases (such as Taq, VENT, etc.), peroxidases (such as HRP), phosphatases (such as alkaline phosphatase), kinases, methylases, ligases, proteases, galactosidases (such as beta-galactosidase, glucuronidase, etc.), transferases (such as chloramphenicol acetyltransferase), oxidoreductases (such as luciferase), and/or nucleases (such as DNAses, RNAses, etc.), among others. SBP members, such as antibodies, digoxigenin, nucleic acids, etc., may be directly conjugated to dyes, enzymes, and/or other SBP members; may be noncovalently bound to dyes and/or enzymes (either pre-bound or bound in an additional exposure step); and/or so on. Further aspects of detection/assay reagents, including the types of assays in which these reagents may be used, are described below in Section XII.

Treatment mechanisms may use fluid-mediated mechanisms to expose particles to reagents. The reagents may be brought to the particles, for example, when the particles are retained, or the particles may be brought to the reagents, for example, when the reagents are present (and optionally retained) in specific portions of fluid networks.

Fluid-mediated mechanisms may be flow-based, field-based, and/or passive, among others. Flow-based treatment mechanisms may operate by fluid flow, mediated, for example, by gravity flow or active flow (pumping), to carry reagents to particles, or vice versa. In some embodiments, the flow-based treatment mechanisms may operate by regulated transverse (side-to-side) positioning, as described above/below in Sections V and X, to precisely regulate exposure of reagents (or particles) to particles (or reagents). By contrast, field-based mechanisms may combine particles and reagents by moving reagents (or particles) with electric fields. The electric fields may produce any suitable electrokinetic effects, such as electrophoresis, dielectrophoresis, electroosmosis, etc. Alternatively, or in addition, reagents may be combined with particles by diffusion of the reagents.

Particles in microfluidic systems may be exposed to physical modulators/conditions using non-fluid-mediated mechanisms. However, these "non-fluid-mediated" mechanisms may use properties of fluid to assist in their operation, such as transfer of thermal energy or pressure to particles via fluid. The physical modulators/conditions may be applied to particles from sources that are external and/or internal to the microfluidic systems. Exemplary physical modulators/conditions may include thermal energy (heat), radiation (light), radiation (particle), an electric field, a magnetic field, pressure (including sound), a gravitational field, etc.

Treatment mechanisms may act on any suitable particles, including any of the particles described above in Section III. The particles may be intact, permeabilized, and/or lysed. Accordingly, treatment mechanisms may act on released cell components. Particles may be treated in arrays, either serially, for example, using a shared treatment mechanism, and/or in parallel, for example, using distinct and/or shared treatment mechanisms.

Further aspects of treatment mechanisms are described above in Section V (positioning reagents/fluid/particles) and below in Section XIII.

(VIII) MEASUREMENT MECHANISMS

Particles manipulated by a microfluidic system may be analyzed by one or more measurement mechanisms at one or more measurement sites. The measurement mechanisms generally comprise any suitable apparatus or method for detecting a preselected particle or particle characteristic (provided, for example, by the particle, a particle component, and/or an assay product, among others). The measurement sites generally comprise any suitable particle position or positions at which a measurement is performed, internal and/or external to the system.

The measurement mechanism may employ any suitable detection method to analyze a sample, qualitatively and/or quantitatively. Suitable detection methods may include spectroscopic methods, electrical methods, hydrodynamic methods, imaging methods, and/or biological methods, among others, especially those adapted or adaptable to the analysis of particles. These methods may involve detection of single or multiple values, time-dependent or time-independent (e.g., steady-state or endpoint) values, and/or averaged or (temporally and/or spatially) distributed values, among others. These methods may measure and/or output analog and/or digital values.

Spectroscopic methods generally may include detection of any property of light (or a wavelike particle), particularly properties that are changed via interaction with a sample. Suitable spectroscopic methods may include absorption, luminescence (including photoluminescence, chemiluminescence, and electrochemiluminescence), magnetic resonance (including nuclear and electron spin resonance), scattering (including light scattering, electron scattering, and neutron scattering), diffraction, circular dichroism, and optical rotation, among others. Suitable photoluminescence methods may include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), fluorescence activated cell sorting (FACS), and their phosphorescence and other analogs, among others.

Electrical methods generally may include detection of any electrical parameter. Suitable electrical parameters may include current, voltage, resistance, capacitance, and/or power, among others.

Hydrodynamic methods generally may include detection of interactions between a particle (or a component or derivative thereof) and its neighbors (e.g., other particles), the solvent (including any matrix), and/or the microfluidic system, among others, and may be used to characterize molecular size and/or shape, or to separate a sample into its components. Suitable hydrodynamic methods may include chromatography, sedimentation, viscometry, and electrophoresis, among others.

Imaging methods generally may include detection of spatially distributed signals, typically for visualizing a sample or its components, including optical microscopy and electron microscopy, among others.

Biological methods generally may include detection of some biological activity that is conducted, mediated, and/or influenced by the particle, typically using another method, as described above. Suitable biological methods are described below in detail in Section XII.

The measurement mechanism may be used to detect particles and/or particle characteristics at any suitable detection site, internal and/or external to the microfluidic system.

Suitable internal detection sites may include any site(s) in or on a microfluidic system (a chip). These sites may include channels, chambers, and/or traps, and portions thereof. Particles or particle characteristics may be detected while the particles (or released components/assay products) are stationary or moving. Stationary particles may be encountered following particle retention, for example, cells growing in a cell chamber. Moving particles may be encountered before and/or after particle retention, or upon confinement to a region. In particular, particles may be moved past a detection site by any suitable positioning mechanism, for example, by fluid flow (flow-based detection).

Suitable external detection sites may include any site(s) away from or independent of a microfluidic system. External detection sites may be used to detect a particle or particle characteristic after removal of particles (or particle components) from a microfluidic system. These external sites may be used instead of and/or in addition to internal sites, allowing particles (or particle components) to be further manipulated and/or detected. These further manipulations and/or detection methods may overlap with, but preferably complement, the manipulations and/or methods performed in the microfluidic system, including mass spectrometry, electrophoresis, centrifugation, PCR, introduction into an organism, use in clinical treatment, and/or cell culture, among others.

The measurement method may detect and/or monitor any suitable characteristic of a particle, directly and/or indirectly (e.g., via a reporter molecule). Suitable characteristics may include particle identity, number, concentration, position (absolute or relative), composition, structure, sequence, and/or activity among others. The detected characteristics may include molecular or supramolecular characteristics, such as the presence/absence, concentration, localization, structure/modification, conformation, morphology, activity, number, and/or movement of DNA, RNA, protein, enzyme, lipid, carbohydrate, ions, metabolites, organelles, added reagent (binding), and/or complexes thereof, among others. The detected characteristics also may include cellular characteristics, such as any suitable cellular genotype or phenotype, including morphology, growth, apoptosis, necrosis, lysis, alive/dead, position in the cell cycle, activity of a signaling pathway, differentiation, transcriptional activity, substrate attachment, cell-cell interaction, translational activity, replication activity, transformation, heat shock response, motility, spreading, membrane integrity, and/or neurite outgrowth, among others.

Further aspects of detected characteristics and their use in particle assays are described below in Sections XII and XIII.

(IX) RELEASE MECHANISMS

A microfluidic system may include any suitable number of particle release mechanisms. A release mechanism generally comprises any mechanism(s) for allowing a retained particle to move away from a preselected site/area at which it is retained, including removing, overcoming, and/or rendering ineffective the retention mechanism(s) that retains the particle. Release mechanisms that are suitable may be selected based, at least partially, on the retaining force. After release, particles (or particle components) may have any suitable destination.

A release mechanism may operate by removing the retaining force. Accordingly, particles that are retained by a specific mechanism may be released by terminating that mechanism. For example, particles retained by a chemical interaction/bond may be released by cleaving the bond, such as with a protease(s) (e.g., trypsin), or otherwise disrupting the interaction, such as with altered ionic conditions (e.g., with EDTA) or pH, or with an excess of a SBP member. Similarly, particles retained by a physical barrier, such as a closed valve, may be released by moving/removing the barrier. Furthermore, particles retained by fluid flow, a vacuum, light, an electrical field, a magnetic field, and/or a centrifugal force may be released by removing/redirecting the corresponding flow, force, field, etc.

A release mechanism may operate by overcoming a retaining force with a greater force. Accordingly, particles may be released by any positioning mechanism(s) that applies a force greater than the retaining force. For example, retained particles may be released by a releasing flow. The releasing flow may be an increased flow rate in the direction of bulk fluid flow, for example, when a particle is weakly retained (such as by gravity/friction, or weak chemical interactions). Alternatively, the releasing flow may act counter to a retaining flow, for example orthogonal or opposite to the retaining flow. For example, the releasing flow may reposition particles to be out of contact with a retaining physical barrier. Alternatively, or in addition, retained particles may be released by any other suitable positioning mechanism(s), as described above in Section V, that is capable of generating sufficient force.

A release mechanism may operate by rendering ineffective the retaining force on a particle. Such a release mechanism may operate by releasing components of the particle. For example, retained cells may be lysed to release intracellular components, producing a lysate, or beads may be treated to release associated materials and/or to fragment/disintegrate the beads. Lysis generally includes any partial or complete disruption of the integrity of a cell-surface membrane, and may be produced via temperature, a detergent, a ligand, chemical treatment, a change in ionic strength, an electric field, etc.

Released particles and/or particle components may have any suitable destination(s). Suitable immediate destinations may include a positioning mechanism and/or fluid surrounding the particles. After release, particles may be repositioned with a positioning mechanism, either nonselectively or selectively. Selective positioning may position the particle based on a measured characteristic. Positioning may be to a second retention mechanism (and/or a culture chamber), to a detection mechanism (such as a flow-based mechanism), and/or to an output mechanism. Fluid surrounding the particles may be a suitable destination for particle components (such as cells lysates and/or bead components) to be contacted with detection/assay reagents. Alternatively, cell lysates and/or bead components may be repositioned as with intact particles.

Further aspects of release mechanisms and destinations of released particles/components are described below in Section XIII.

(X) OUTPUT MECHANISMS

Microfluidic systems may include one or more output mechanisms that interface with the microfluidic network(s). An output mechanism generally comprises any suitable mechanism for outputting material(s) (e.g., fluid, particles, and/or reagents) from a microfluidic system, or portions thereof, including selective and/or bulk mechanisms. The output mechanism may direct outputted material to any suitable location, such as an internal and/or external sink. A sink generally comprises any receptacle or other site for receiving outputted materials, for disposal (e.g., a waste site) or for further study or manipulation (e.g., a collection site). The outputting of materials from the microfluidics system may be facilitated and/or regulated using any suitable facilitating mechanism, such as sources of internal pressure and/or external vacuum. The output mechanism may include a selection mechanism, such as a filter, that selects outputted materials based on some criterion, such as whether the material is a particle or a fluid.

(XI) CELL CULTURE MECHANISMS

Cells may be cultured using a cell culture mechanism in microfluidic systems. The cell culture mechanism generally comprises any suitable mechanism for growing cells, including maintenance and/or propagation. Suitable cells are described above in Section III.

A cell culture mechanism of a microfluidic system may include one or more culture chambers in which to culture cells. Culture chambers may have any suitable size, shape, composition, and/or relationship to other aspects of microfluidic systems, based on the number of cells to be cultured, size of cells, assays to performed on the cells, and/or growth characteristics of the cells, among others. The size of a culture chamber may be only large enough to hold one cell, several cells or more (2 to 50), or many cells (50 to 1000 or more) of a given cell size. Accordingly, culture chambers may be defined by a selected portion of a passage, an entire passage, or a set of passages. In some embodiments, culture chambers may be formed by substantially enlarged channels. Culture chambers may have any suitable height that allows cells of interest to enter the chamber. This height may be greater than, less than, and/or equal to other portions of the microfluidic network. Some or all of the surfaces of a culture chamber, such as the walls, roof, and/or substrate, may be treated or modified to facilitate aspects of cell culture, particularly specific or nonspecific cell attachment, cell survival, cell growth, and/or cell differentiation (or lack thereof), among others. Suitable methods of passage treatment and treatment agents are described above in Section VI, relative to chemical retention mechanisms.

The cell culture mechanism may culture cells under any suitable environmental conditions using any appropriate environmental control mechanisms. Suitable environmental conditions may include a desired gas composition, temperature, rate and frequency of media exchange, and/or the like. Environmental control mechanisms may operate internal and/or external to a microfluidic system. Internal mechanisms may include on-board heaters, gas conduits, and/or media reservoirs. External mechanisms may include an atmosphere- and/or temperature-controlled incubator/heat source, and/or a media source external to the system. An atmosphere-controlled incubator may be more suitable when the system is at least partially formed of a gas-permeable material, such as PDMS. Media, including gas-conditioned media, may be introduced from an external source by any suitable input mechanism, including manual pipetting, automated pipetting, noncontact spitting, etc. In some embodiments, the chip may be preincubated with media, which may then be discarded, prior to the introduction of cells and/or other biological materials.

(XII) PARTICLE-BASED MANIPULATIONS

Microfluidic systems are used for particle manipulations. Particle manipulations generally comprise any suitable sequence of unitary operations, for performing a desired function or assay. Unitary operations may be performed by each of the mechanisms described above in Sections IV to X, among others.

The microfluidic systems may be used for any suitable cell assays or methods, including any combinations of cells, cell selection(s) (by selective retention), treatment(s), and/or measurement(s), as described above in Sections III, VI, VII, and VIII, respectively.

The cell assays may characterize cells, either with or without addition of a modulator. Cell assays may measure cell genotypes, phenotypes, and/or interactions with modulators. These assays may characterize individual cells and/or cell populations/groups of any suitable size. Cells may be characterized in the absence of an added modulator to define one or more characteristics of the cells themselves. Alternatively, or in addition, cell may be characterized in the presence of an added modulator to measure interaction(s) between the cells and the modulator. Moreover, cells may be exposed to a selected concentration of a reagent, or a plurality of concentrations of a reagent. In other embodiments, cells are exposed to a gradient of concentrations of reagent to determine whether such cells will be attracted or repelled by increasing amounts of such reagent.

In other embodiments, a quantity of cells may be measured out by first filling a measuring chamber having at least one inlet, the inlet having at least one valve, where the valve is opened, cells are introduced into the chamber, preferably by blind filling a dead-end chamber, or by opening up an outlet valve to an outlet in communication with the chamber, the outlet having a retention mechanism for preventing the cells from exiting the chamber. The measure amount of cells is then displaced to a culturing region for culturing.

In other embodiments, a first type of cell is grown in fluid communication with a second type of cell, wherein the first type of cell is affected by the presence of the second type of cell, preferably as a co-culture or feeder type relationship. The cells of the first type and the cells of the second type are kept separate from each other by a retention mechanism, although fluid, preferably liquid, is permitted to be in joint contact with each type of cell so that sub-cellular or biochemical materials may be exchanged between cell types.

Genotypic assays may be conducted on cells in microfluidic systems to measure the genetic constitution of cells. The genotypic assays may be conducted on any suitable cell or cell populations, for example, patient samples, prenatal samples (such as embryonic, fetal, chorionic villi, etc.), experimentally manipulated cells (such as transgenic cells), and/or so on. Such genotypic aspects may include copy number (such as duplication, deletion, amplification, and/or the like) and/or structure (such as rearrangement, fusion, number of repeats (such as dinucleotide, triplet repeats, telomeric repeats, etc.), mutation, gene/pseudogene, specific allele, presence/absence/identity/frequency of single nucleotide polymorphisms, integration site, chromosomal/episomal, and/or the like) of a nuclear and/or mitochondrial gene(s), genomic region(s), and/or chromosomal region (s) (such as telomeres, centromeres, repetitive sequences, etc.). Methods for genotypic assays may include nucleic acid hybridization in situ (on intact cells/nuclei) or with DNA released from cells, for example, by lysing the cells. Nucleic acid hybridization with nucleic acids may be carried out with a dye-labeled probe, a probe labeled with a specific binding pair (see Section VI), a stem-loop probe carrying an energy transfer pair (such as a "molecular beacon"), and/or with a probe that is labeled enzymatically after hybridization (such as by primer extension with a polymerase, modification with terminal transferase, etc). Alternatively, or in addition, methods for genotypic assays may include polymerase-mediated amplification of nucleic acids, for example, by thermal cycling (PCR) or by isothermal strand-displacement methods. In some embodiments, genotypic assays may use electrophoresis to assist in analysis of nucleic acids. Related gene-based assays may measure other aspects of gene regions, genes, chromosomal regions, whole chromosomes, or genomes, using similar assay methods, and suitable probes or DNA dyes (such as propidium iodide, H echst, etc.). These other aspects may include total DNA content (for example 2N, 4N, 8N, etc., to measure diploid, tetraploid, or polyploid genotypes and/or cell cycle distribution), number or position of specific chromosomes, and/or position of specific genes (such as adjacent the nuclear membrane, another nuclear structure, and so on).

Phenotypic assays may be conducted to characterize cells in microfluidic systems, based on genetic makeup and/or environmental influences, such as presence of modulators. These assays may measure any molecular or cellular aspect of whole cells, cellular organelles, and/or endogenous (native) or exogenous (foreign) cell constituents/components.

Aspects of a whole cell or whole cell population may include number, size, density, shape, differentiation state, spreading, motility, translational activity, transcriptional activity, mitotic activity, replicational activity, transformation, status of one or more signaling pathways, presence/absence of processes, intact/lysed, live/dead, frequency/extent of apoptosis or necrosis, presence/absence/efficiency of attachment to a substrate (or to a passage), growth rate, cell cycle distribution, ability to repair DNA, response to heat shock, nature and/or frequency of cell-cell contacts, etc.

Aspects of cell organelles may include number, size, shape, distribution, activity, etc. of a cell's (or cell population's) nuclei, cell-surface membrane, lysosomes, mitochondria, Golgi apparatus, endoplasmic reticulum, peroxisomes, nuclear membrane, endosomes, secretory granules, cytoskeleton, axons, and/or neurites, among others.

Aspects of cell constituents/components may include presence/absence or level, localization, movement, activity, modification, structure, etc. of any nucleic acid(s), polypeptide(s), carbohydrate(s), lipid(s), ion(s), small molecule, hormone, metabolite, and/or a complex(es) thereof, among others. Presence/absence or level may be measured relative to other cells or cell populations, for example, with and without modulator. Localization may be relative to the whole cell or individual cell organelles or components. For example, localization may be cytoplasmic, nuclear, membrane-associated, cell-surface-associated, extracellular, mitochondrial, endosomal, lysosomal, peroxisomal, and/or so on. Exemplary cytoplasmic/nuclear localization may include transcription factors that translocate between these two locations, such as NF-.kappa.B, NFAT, steroid receptors, nuclear hormone receptors, and/or STATs, among others. Movement may include intracellular trafficking, such as protein targeting to specific organelles, endocytosis, exocytosis, recycling, etc. Exemplary movements may include endocytosis of cell-surface receptors or associated proteins (such as GPCRs, receptor tyrosine kinases, arrestin, and/or the like), either constitutively or in response to ligand binding. Activity may include functional or optical activity, such as enzyme activity, fluorescence, and/or the like, for example, mediated by kinases, phosphatases, methylases, demethylases, proteases, nucleases, lipases, reporter proteins (for example beta-galactosidase, chloramphenicol acetyltransferase, luciferase, glucuronidase, green fluorescent protein (and related derivatives), etc.), and/or so on. Modification may include the presence/absence, position, and/or level of any suitable covalently attached moiety. Such modifications may include phosphorylation, methylation, ubiquitination, carboxylation, and/or farnesylation, among others. Structure may include primary structure, for example after processing (such as cleavage or ligation), secondary structure or tertiary structure (e.g., conformation), and/or quaternary structure (such as association with partners in, on, or about cells). Methods for measuring modifications and/or structure may include specific binding agents (such as antibodies, etc.), in vivo or in vitro incorporation of labeled reagents, energy transfer measurements (such as FRET), surface plasmon resonance, and/or enzyme fragment complementation or two-hydrid assays, among others.

Nucleic acids may include genomic DNA, mitochondrial DNA, viral DNA, bacterial DNA, phage DNA, synthetic DNA, transfected DNA, reporter gene DNA, etc. Alternatively, or in addition, nucleic acids may include total RNAs, hnRNAs, mRNAs, tRNAs, siRNAs, dsRNAs, snRNAs, ribozymes, structural RNAs, viral RNAs, bacterial RNAs, gene-specific RNAs, reporter RNAs (expressed from reporter genes), and/or the like. Methods for assaying nucleic acids may include any of the techniques listed above under genotypic assays. In addition, methods for assaying nucleic acids may include ribonuclease protection assays.

Polypeptides may include any proteins, peptides, glycoproteins, proteolipids, etc. Exemplary polypeptides include receptors, ligands, enzymes, transcription factors, transcription cofactors, ribosomal components, regulatory proteins, cytoskeletal proteins, structural proteins, channels, transporters, reporter proteins (such as those listed above which are expressed from reporter genes), and/or the like. Methods for measuring polypeptides may include enzymatic assays and/or use of specific binding members (such as antibodies, lectins, etc.), among others. Specific binding members are described in Section VI.

Carbohydrates, lipids, ions, small molecules, and/or hormones may include any compounds, polymers, or complexes. For example, carbohydrates may include simple sugars, di- and polysaccharides, glycolipids, glycoproteins, proteoglycans, etc. Lipids may include cholesterol and/or inositol lipids (e.g., phosphoinositides), among others; ions may include calcium, sodium, chloride, potassium, iron, zinc, hydrogen, magnesium, heavy metals, and/or manganese, among other; small molecules and/or hormones may include metabolites, and/or second messengers (such as cAMP or cGMP, among others), and/or the like.

Interaction generally comprises any specific binding of a modulator to a cell or population of cells, or any detectable change in a cell characteristic in response to the modulator. Specific binding is any binding that is predominantly to a given partner(s) that is in, on, or about the cell(s). Specific binding may have a binding coefficient with the given partner of about $10^{-3}$ M and lower, with preferred specific binding coefficients of about $10^{-4}$ M, $10^{-6}$ M, or $10^{-8}$ M and lower. Alternatively, interaction may be any change in a phenotypic or genotypic characteristic, as described above, in response to the modulator.

Interaction assays may be performed using any suitable measurement method. For example, the modulator may be labeled, such as with an optically detectable dye, and may be labeled secondarily after interaction with cells. Binding of the dye to the cell or cells thus may be quantified. Alternatively, or in addition, the cell may be treated or otherwise processed to enable measurement of a phenotypic characteristic produced by modulator contact, as detailed above and in Section VIII.

Cells and/or cell populations may be screened with libraries of modulators to identify interacting modulators and/or modulators with desired interaction capabilities, such as a desired phenotypic effect (such as reporter gene response, change in expression level of a native gene/protein, electrophysiological effect, etc.) and/or coefficient of binding. A library generally comprises a set of two or more members (modulators) that share a common characteristic, such as structure or function. Accordingly, a library may include two or more small molecules, two or more nucleic acids, two or more viruses, two or more phages, two or more different types of cells, two or more peptides, and/or two or more proteins, among others.

Microfluidic assays of cells and/or populations may measure activity of signal transduction pathways. The activity may be measured relative to an arbitrary level of activity, relative to other cells and/or populations (see below), and/or as a measure of modulator interaction with cells (see above).

Signal transduction pathways generally comprise any flow of information in a cell. In many cases, signal transduction pathways transfer extracellular information, in the form of a ligand(s) or other modulator(s), through the membrane, to produce an intracellular signal. The extracellular information may act, at least partially, by triggering events at or near the membrane by binding to a cell-surface receptor, such as a G Protein-Coupled Receptor (GPCR), a channel-coupled receptor, a receptor tyrosine kinase, a receptor serine/threonine kinase, and/or a receptor phosphatase, among others. These events may include changes in channel activity, receptor clustering, receptor endocytosis, receptor enzyme activity (e.g., kinase activity), and/or second messenger production (e.g., cAMP, cGMP, diacylglycerol, phosphatidylinositol, etc.). Such events may lead to a cascade of regulatory events, such as phosphorylation/dephosphorylation, complex formation, degradation, and/or so on, which may result, ultimately, in altered gene expression. In other cases, modulators pass through the membrane and directly bind to intracellular receptors, for example with nuclear receptors (such as steroid receptors (GR, ER, PR, MR, etc.), retinoid receptors, retinoid X receptor (RXRs), thyroid hormone receptors, peroxisome proliferation-activating receptors (PPARs), and/or xenobiotic receptors, among others). Therefore, any suitable aspect of this flow of information may be measured to monitor a particular signal transduction pathway.

The activity measured may be based at least partially, on the type of signal transduction pathway being assayed. Accordingly, signal transduction assays may measure ligand binding; receptor internalization; changes in membrane currents; association of receptor with another factor, such as arrestin, a small G-like protein such as rac, or rho, and/or the like; calcium levels; activity of a kinase, such as protein kinase A, protein kinase C, CaM kinase, myosin light chain kinase, cyclin dependent kinases, PI3-kinase, etc.; cAMP levels; phosholipase C activity, subcellular distribution of proteins, for example, NF-.kappa.B, nuclear receptors, and/ or STATs, among others. Alternatively, or in addition, signal transduction assays may measure expression of native target genes and/or foreign reporter genes that report activity of a signal transduction pathway(s). Expression may be measured as absence/presence or level of RNA, protein, metabolite, or enzyme activity, among others, as described above.

Cell-based assays may be used to compare genotypic, phenotypic, and/or modulator interaction of cells and/or populations of cells. The cells and/or populations may be compared in distinct microfluidic systems or within the same microfluidic system. Comparison in the same microfluidic system may be conducted in parallel using a side-by-side configuration.

Microfluidic systems may be used to perform single-cell assays, which generally comprise any assays that are preferably or necessarily performed on one cell at a time. Examples of single cell assays include patch-clamp analysis, single-cell PCR, single-cell fluorescence in situ hybridization (FISH), subcellular distribution of a protein, and/or differentiation assays (conversion to distinct cell types). In some cases, single-cell assays may be performed on a retained group of two or more cells, by measuring an individual characteristic of one member of the group. In other cases, single-cell assays may require retention of a single cell, for example, when the cell is lysed before the assay.

Microfluidic systems may be used to sort or select single cells and/or cell populations. The sorted/selected cells or populations may be selected by stochastic mechanisms, size, density, magnetic properties, cell-surface properties (that is, ability to adhere to a substrate), growth and/or survival capabilities, and/or based on a measured characteristic of the cells or populations (such as response to a ligand, specific phenotype, and/or the like). Cells and/or populations may be sorted more than once during manipulation and/or analysis in a microfluidic system. In particular, heterogeneous populations of cells, such as blood samples or clinical biopsies, partially transfected or differentiated cell populations, disaggregated tissues, natural samples, forensic samples, etc. may be sorted/selected.

Microfluidic systems may perform storage and/or maintenance functions for cells. Accordingly, cells may be introduced into microfluidic systems and cultured for prolonged periods of time, such as longer than one week, one month, three months, and/or one year. Using microfluidic systems for storage and/or maintenance of cells may consume smaller amounts of media and space, and may maintain cells in a more viable state than other storage/maintenance methods. Additional aspects of storing and maintaining cells in microfluidic systems are included in Section XI above.

Microfluidic systems may be used for any suitable virally based, organelle-based, bead-based, and/or vesicle-based assays and/or methods. These assays may measure binding (or effects) of modulators (compounds, mixtures, polymers, biomolecules, cells, etc.) to one or more materials (compounds, polymers, mixtures, cells, etc.) present in/on, or associated with, any of these other particles. Alternatively, or in addition, these assays may measure changes in activity (e.g., enzyme activity), an optical property (e.g., chemiluminescence, fluorescence, or absorbance, among others), and/or a conformational change induced by interaction.

In some embodiments, beads may include detectable codes. Such codes may be imparted by one or more materials having detectable properties, such as optical properties (e.g., spectrum, intensity, and or degree of fluorescence excitation/emission, absorbance, reflectance, refractive index, etc.). The one or more materials may provide nonspatial information or may have discrete spatial positions that contribute to coding aspects of each code. The codes may allow distinct samples, such as cells, compounds, proteins, and/or the like, to be associated with beads having distinct codes. The distinct samples may then be combined, assayed together, and identified by reading the code on each bead. Suitable assays for cell-associated beads may include any of the cell assays described above.

Suitable protocols for performing some of the assays described in this section are included in Joe Sambrook and David Russell, Molecular Cloning: A Laboratory Manual (3rd ed. 2000), which is incorporated herein by reference.

(XIII) EMBODIMENTS

The following examples describe selected aspects and embodiments, including methods, systems, and devices for multiple single-particle, such as single-cell, processing utilizing microfluidics. These examples are included for illustration and are not intended to limit or define the entire scope of the invention.

Turning to FIG. 1, a microfluidic system 100 is shown that is configured for capturing multiple individual cells and processing them. System 100 includes a microfluidic device 110 that may be coupled with a microfluidic controller 120. System 100 may be configured to handle populations of cells that range in order of magnitude from tens, hundreds, or even thousands of cells. System 100 may capture individual or single cells from the larger population of cells. These individual cells may be imaged and/or stimulated utilizing different reagents in some embodiments. The individual captured cells may be processed to utilize a variety of multi-step chemistries or processes including, but not limited to, specific target amplification (STA), reverse transcription specific target amplification (RT-STA), genomic DNA STA, whole genome amplification (WGA), whole methylome amplification, whole transcriptome amplification (WTA), real-time PCR preparation, preamplification, mRNA sequencing; RNA sequencing, copy number variation (CNV), multimodal applications (DNA/RNA; Protein/RNA), protein applications, sample processor applications, and/or haplotyping. Reaction products may then be exported for additional analysis and/or processing.

Some embodiments may be configured to load hundreds of cells into a microfluidic device. For example, in one embodiment, at least 200 mammalian cells (5-25 um diameter) may be loaded and partitioned such that each of 96 chambers may contain up to one cell. Some embodiments may allow for imaging of the partitioned cells. Other embodiments may include more or less chambers and partition more or less cells, for example. The cells may be confined or captured such that their basal solution/medium may be replaced with another reagent. Multi-step reactions may be performed on each of the 96 partitioned samples. Target applications include, but are not limited to: Specific Target Amplification (STA); Reverse Transcription Specific Target Amplification (RT-STA); genomic DNA STA; Whole Genome Amplification (WGA); Whole Transcriptome Amplification (WTA); Whole Methylome Amplification; Preamplification; mRNA Sequencing; RNA Sequencing; Real-time PCR prep; Copy Number Variation (CNV); Multimodal Applications (DNA/RNA; Protein/RNA); Protein Applications; Sample Processor Applications; or haplotyping. In some embodiments, the microfluidic device may be designed such that the single cells or their components (DNA, RNA, chromosomes, etc.) can be chemically manipulated in multiple steps (for example: cell lysis, RNA reverse transcription, and pre-amp for loading a gene expression microfluidic device). The processed sample may be exported from the microfluidic device.

Some embodiments may be configured to load a population of a minimum of 200 mammalian cells with a defined size range. The size range may be broad enough to include a majority of mammalian cells. Different classes of microfluidic devices or integrated fluidic circuits (IFC) may be utilized in order to cover all major size classed, 5-15 u and 15-25 um, for example. Merely by way of example, at 200 cells, the capture efficiency may be >50% defined as over 48 of the 96 capture sites will contain one cell. At 500 cells, the capture efficiency may be >80%. In some embodiments, the capture protocol at application release may be required to work with suspension cells (e.g. K562) and adherent cells from tissue culture (e.g. HUVECs). Some embodiments may include ADP format, including cells isolated from tissue samples or cells or nuclei isolated from LCM or FFPE samples. The IFC may capture 96 single cells from the population for individual reactions in some embodiments. Some embodiments may be configured to verify the presence of a single cell in each reaction. The requirement may be to distinguish the absence of a cell and the presence of two cells versus one cell. Some embodiments may allow a user to induce with at least a single biological reagent for up to some time period, such as 6 hours, before lysis. In some embodiments, the user may be capable of imaging the cells before lysis. Some embodiments may be configured to perform WTA and/or WGA. These may utilize commercially available reagents. Some embodiments may collect individual material from each cell in quantities sufficient enough for subsequent NGS library preparation.

Some embodiments may be configured for library preparation. Embodiments may automatically prepare multiple, 96 for example, sequencing-ready libraries from gDNA and cDNA using commercially available reagents. Each library may be uniquely indexed using NGS indexes. Total reagent consumption may be equal to or less than a single sample preparation on a macro scale. Embodiments may include: dispensing samples and reagents into the IFC; placing the IFC in the microfluidic controller; post processing collecting the product from the IFC with a standard pipette; and/or performing single purification and quantitation step prior to clonal amplification. Some embodiments support STA workflow.

Some embodiments may be configured for haplotyping. For example, some embodiments may start with 4 gDNA samples. Starting material may include: genomic DNA; chromosome suspensions; fosmid libraries; and/or whole cells. Some embodiments may generate 4 unique sequencer-ready libraries which will allow the researcher to haplotype at least 90% of the human genome. Additional replicates may be required for non-human genomes.

Figure 2:
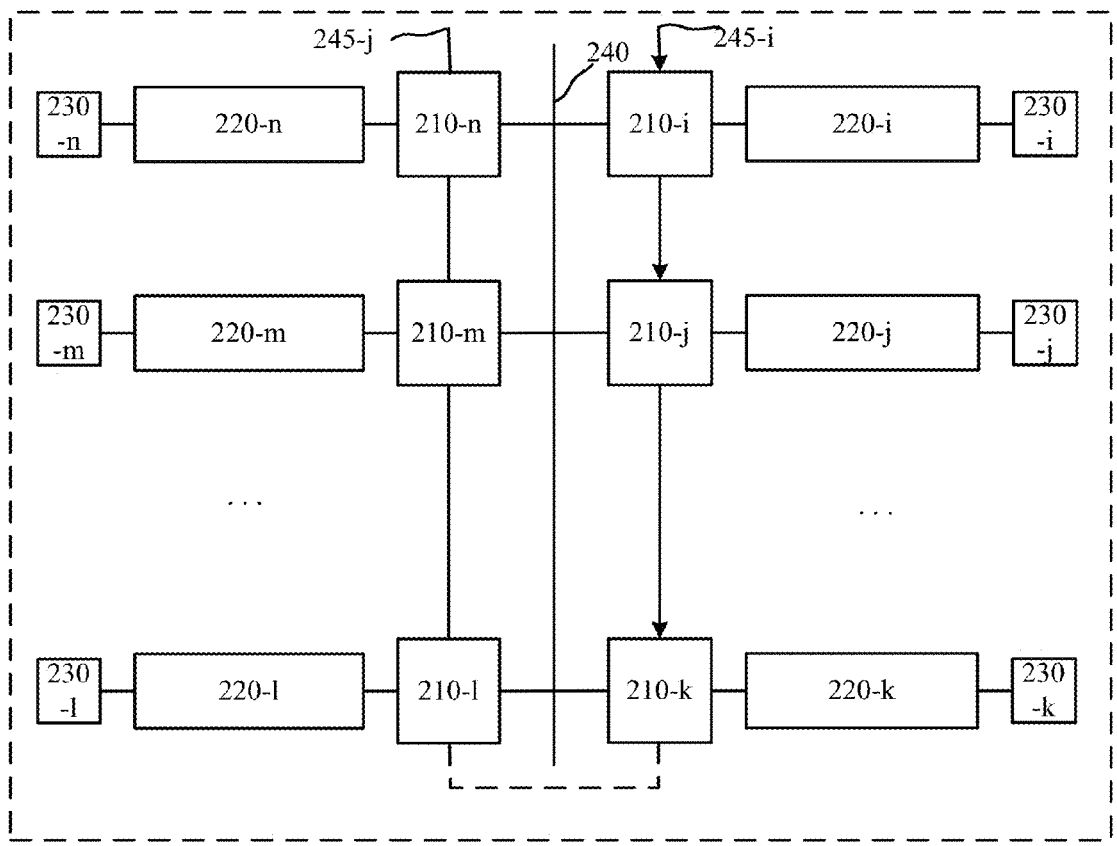
FIG. 2 shows a diagram of a microfluidic device in accordance with various embodiments.

FIG. 2 shows an example of a microfluidic device 110-a in accordance with various embodiments. Microfluidic device 110-a may be an example of microfluidic device 110 of FIG. 1. Microfluidic device 110-a may be referred to as a microfluidic chip in some embodiments. Microfluidic device 110-a may be coupled with a microfluidic carrier (not shown) in some embodiments.

Microfluidic device 110-a may include multiple capture configurations 210, such as specific capture configurations 210-i, 210-j, 210-k, 210-l, 210-m, and/or 210-n. Capture configurations 210 may be referred to as capture modules in some embodiments. Capture configurations 210 may be coupled in series, or daisy chained, with each other. Each capture configuration 210 may be configured to capture an individual cell when a group or population of cells is flowed through the respective capture configuration 210. Cells that are not capture by a specific capture configuration, such as capture configuration 210-i, for example, may then flow to a subsequent capture configuration, such as capture 210-j, for example, where an individual or single particle and/or cell may be captured, and so on down through the series of capture configurations 210.

In some embodiments, the individually captured cells within respective capture configurations 210 may be washed and/or stimulated utilizing different reagents. Some embodiments may be configured such that the captured cells may also be imaged. Microfluidic device 110-a may include one or more flow channels 240 that may be utilized for introducing different reagents into the capture configurations 210. Some embodiments may include multiple flow channels 240.

Each respective capture configuration 210 may be coupled with a multi-chamber reaction configuration 220, and more specifically multi-chamber reaction configurations 220-i, 220-j, 220-k, 220-l, 220-m, and/or 220-n. A capture cell and/or particle in a specific capture configuration such as capture configuration 210-i may be transported into the associated multi-chamber reaction configuration 220-i for processing. The processing that may occur with a multi-chamber reaction configuration 220 may include, but is not limited to, specific target amplification, RT-STA, mRNA-SEQ, preamplification, WMA, multimodal applications, protein applications, sample processor applications, whole genome amplification, whole transcriptome amplification, real-time PCR preparation, copy number variation, or haplotyping. In some embodiments, there may be active mixing between one or more of the chambers of multi-chamber reaction configuration 220. Thermal cycling may also occur as part of the processing, which may occur as active mixing between chambers may be occurring. Resulting reaction products may then be provided to an export configuration 230, and more specifically export configurations 230-i, 230-j, 230-k, 230-l, 230-m, and/or 230-n. Export configuration 230 may be referred to as a harvest configuration, harvest well, and/or harvest inlet in some cases. Flow between different chambers of a respective multi-chamber reaction configuration 220, a respective capture configuration 210, and/or flow channel 240 may be controlled utilizing different valve and/or pump structures (not shown). Flow channel 240 may be utilized to introduce solutions, such as reagents and/or buffers into microfluidic device 110-a. Flow channel 245-i may be utilized to introduce cells into microfluidic device 110-a. In some cases, flow channel 245-i may be coupled to both sides of capture configurations 210. In some cases, an additional flow channel 245-j may be utilized to provide two separate groups of capture configurations 210, multi-chamber reaction chambers 220, and export configurations.

In some embodiments, microfluidic device 110-a may be configured for multiple single-cell capture and processing. In some embodiments, microfluidic device 110-a may include multiple capture configurations 210 capture configurations coupled in series. Each respective capture configuration 210 may be configured to capture a single cell. Microfluidic device 110-a may include multi-chamber reaction configurations 220. Each respective multi-chamber reaction configuration 220 may be coupled with a respective capture configuration 210 from the multiple capture configurations 210 and may be configured for single-cell processing.

In some embodiments, each respective capture configuration 210 includes one or more a physical barriers sized to hold only a single cell. In some embodiments, each respective capture configuration 210 includes: one or more bypass channels coupled with an input channel and an output channel; a drain coupled with the input channel and the output channel; and/or a capture nest situated proximal to a junction of the input channel and the one or more bypass channels and coupled with the drain, wherein the capture nest is configured to capture a single cell from multiple cells such that a remaining collection of cells is diverted into at least one of the one or more bypass channels when the single cell is captured in the capture nest. In some cases, the one or more bypass channels include a first bypass channel and a second bypass channel. The first bypass channel and the second bypass channel may be symmetrically configured. The symmetrically configured first bypass channel and second bypass channel may include a first wing configuration and a second wing configuration. In some embodiments, at least the input channel or the output channel is further configured as a focusing channel. The focusing channel may include a narrowing channel in at least a horizontal direction or a vertical direction.

In some embodiments, multi-chamber reaction configurations 220 are further configured for thermal cycling while one or more valves of a respective multi-chamber reaction configuration 220 is actuated. Microfluidic device 110-a may include one or more imaging features in some cases. Each respective imaging feature may allow for imaging of captured single cells at a respective capture nest site. Some embodiments include multiple harvest wells. For example, each export configuration 230 may include a harvest well. Each respective harvest well may be coupled with a respective multi-chamber reaction configuration 220 and may be configured to deliver reaction products for further analysis.

Some embodiments of microfluidic device 110-a may include a genomic analysis configuration coupled with each respective multi-chamber reaction configuration 220 to further analyze the reaction products from each respective multi-chamber reaction configuration 220.

In some embodiments, each respective capture configuration 210 includes a capture chamber configured to capture a single cell from a limiting dilution. Each capture chamber may be configured to capture a single cell utilizing a stochastic capture process.

In some embodiments, each respective capture configuration 210 may include: a capture compartment; and/or a binding partner covering a discrete region of the capture compartment, where the discrete portion is sized so that only a single particle binds to the discrete region.

In some embodiments, each respective capture configuration 210 may include one or more capture supports. Each capture support may include a binding partner distributed over at least a portion of the capture support. The one or more capture supports may include one or more bead structures. Some embodiments may include a capture feature configured to capture the support.

In general, the different microfluidic devices described herein may fabricated utilizing a variety of fabrication methods using elastomeric materials, such as PDMS, and methods for design of the microfluidic devices and their components have been described in detail in the scientific and patent literature. See, e.g., Unger et al. (2000) Science 288:113-116; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Micro fluidic devices including three-dimensionally arrayed channel networks); U.S. Patent Application Publication Nos. 2004/0115838; 2005/0072946; 2005/0000900; 2002/0127736; 2002/0109114; 2004/0115838; 2003/0138829; 200210164816; 2002/0127736; and 2002/0109114; PCT Publication Nos. WO 2005/084191; WO 05/030822A2; and WO 01101025; Quake & Scherer, 2000, "From micro to nanofabrication with soft materials" Science 290: 1536-40; Unger et al., 2000, "Monolithic microfabricated valves and pumps by multilayer soft lithography" Science 288: 113-116; Thorsen et al., 2002, "Micro fluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23, Hong et. al, 2004, "A nanoliter-scale nucleic acid processor with parallel architecture" Nature Biotechnology 22:435-39, all incorporated by reference for all purposes.

Figure 3A:
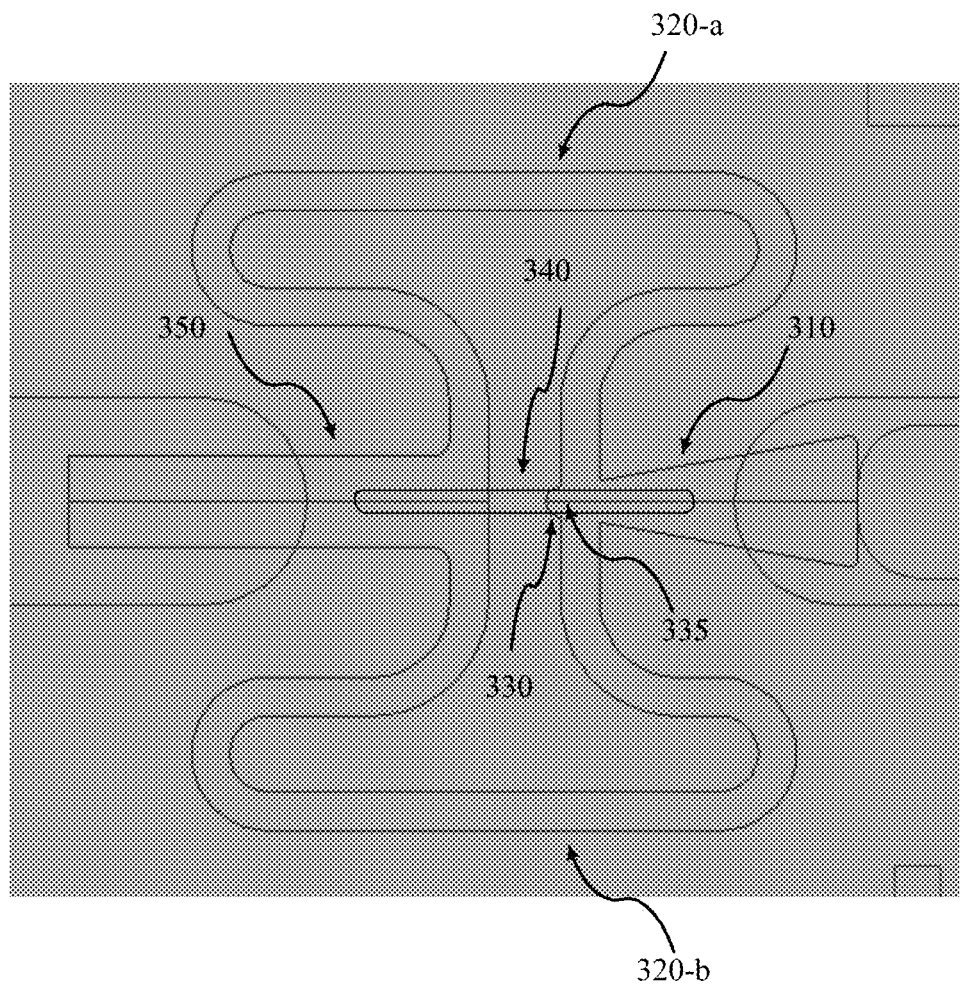
FIG. 3A shows a diagram of a capture configuration of a microfluidic device in accordance with various embodiments.

FIG. 3A shows an example of a capture configuration 210-a in accordance with various embodiments. Capture configuration 210-a may be an example of a capture configuration 210 in general and/or specific capture configurations 210-i, 210-j, 210-k, 210-l, 210-m, and/or 210-n of FIG. 2. Capture configuration 210-a may include different components or aspects. For example, capture configuration 210-a may include an input channel 310 and an output channel 350. Input channel 310 may be configured to focus a solution containing cells so that they may be centered and/or directed towards a capture site, such as capture nest 330. This may be referred to as a front-end focus. Some embodiments may include a back-end focus for the output channel 350. Capture configuration 210-a may include a capture site 335 and/or a capture nest 330. Capture nest 330 and/or capture site 335 may be configured such that a capture cell and/or particle may be protected from being dislodged by flow fluids, including other cells or particles, when captured at the capture nest 330 and/or capture site 335. Capture configuration 210-a may also be configured to create a stagnation point around capture site 335 to facilitate capturing individual cells. Capture configuration 210-a may include a drain 340. Drain 340 may be a small enough channel where cells do not pass through it, but large enough to allow liquid to flow through it. Drain 340 may be coupled to capture nest 330, input channel 310, and/or output channel 350 to facilitate capturing individual cells at capture nest 330. Some embodiments include multiple bypass channels, such as bypass channel 320-a and 320-b. Bypass channels 320 may allow solutions, which may include other cells, to flow to either side of capture nest 330 that is already occupied by a capture cell and/or particle and into at least one of the bypass channels 320, which may facilitate protecting the individual capture cell and/or particle from being dislodged from capture nest 330. Flow through bypass channels 320 may also facilitate an individual cell and/or particle from being captured at capture nest 330, rather than allowing for multiple cells from being captured at cell nest 330. Bypass channels 320 may be configured symmetrically in some embodiments. Bypass channels 320 may be configured into different arrangements including, but not limited to the "wing" shaped arrangement shown with bypass channels 320-a and 320-b.

Capture configuration 210-a may be utilized to capture an individual cell and/or particles. For example, cells may flow into capture configuration 210-*a* from right to left through input channel 310. Cells may get focused into the center of capture site 335. Some liquid may flow through drain 340 in the capture site 335, some flows around the sides into bypass channels 320-*a*/320-*b*. If a cell enters the capture nest 330 and/or drain 340, it may get caught and fill the drain channel, stopping only the flow through the drain channel. Remaining cell and/or particle solution may bypass the blocked capture site 335 through bypass channels 320-*a*/320-*b* and enter the next capture configuration 210 downstream.

Figure 3B:
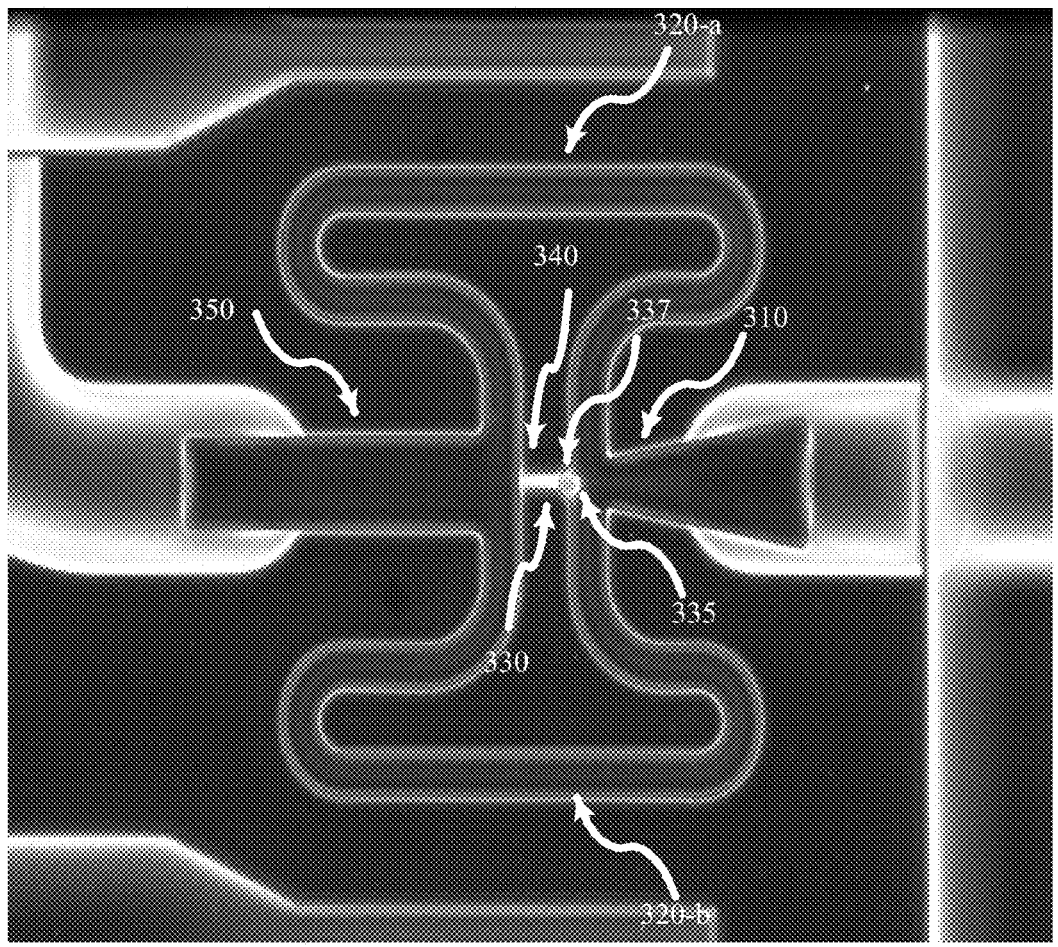
FIG. 3B shows a micrograph of a capture configuration of a microfluidic device in accordance with various embodiments.
Figure 3C:
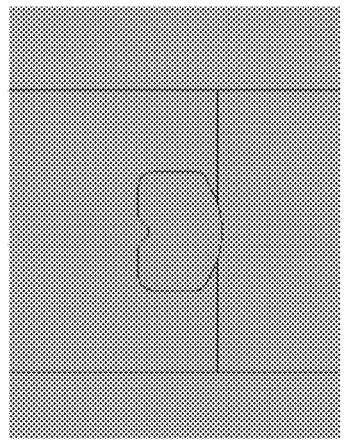
FIGS. 3C-3K show different capture configurations of a microfluidic device in accordance with various embodiments.
Figure 3D:
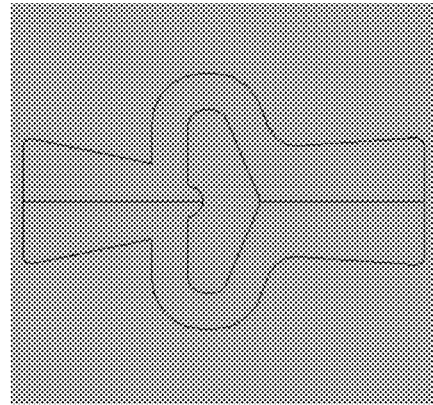
Figure 3E:
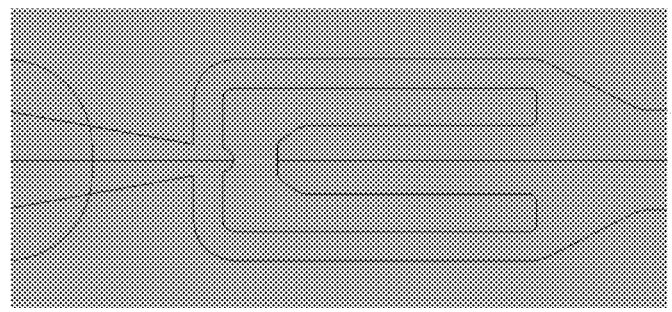
Figure 3F:
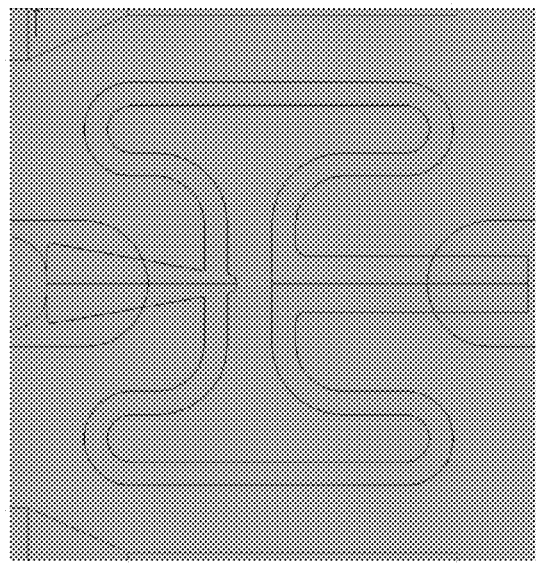
Figure 3G:
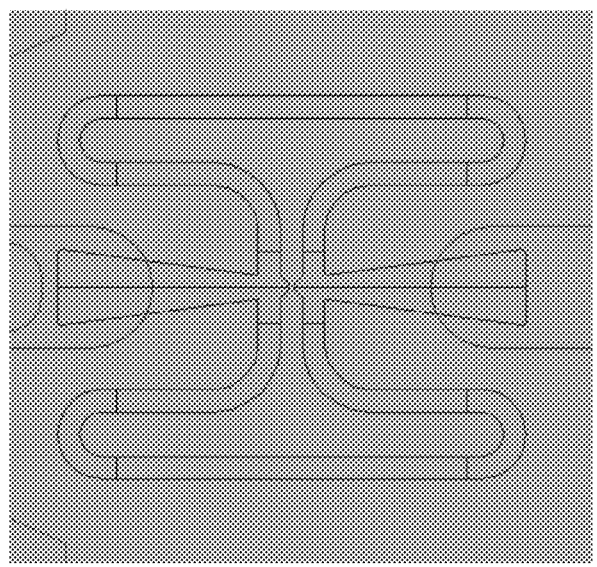
Figure 3H:
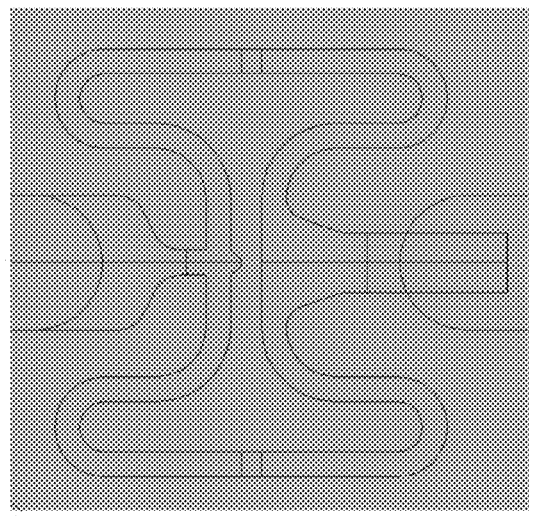
Figure 3I:
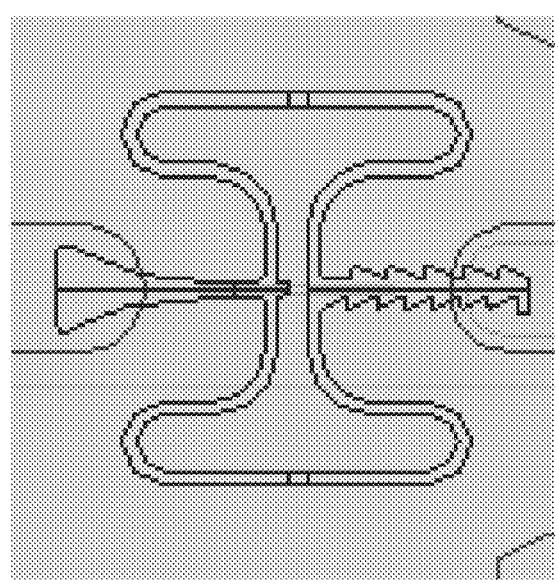
Figure 3J:
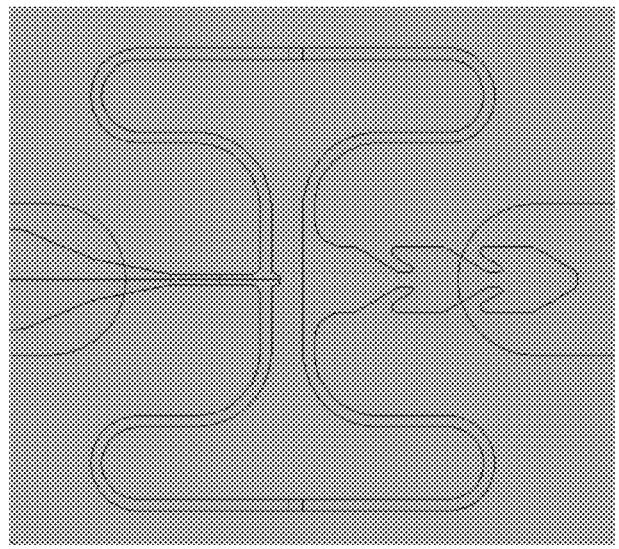
Figure 3K:
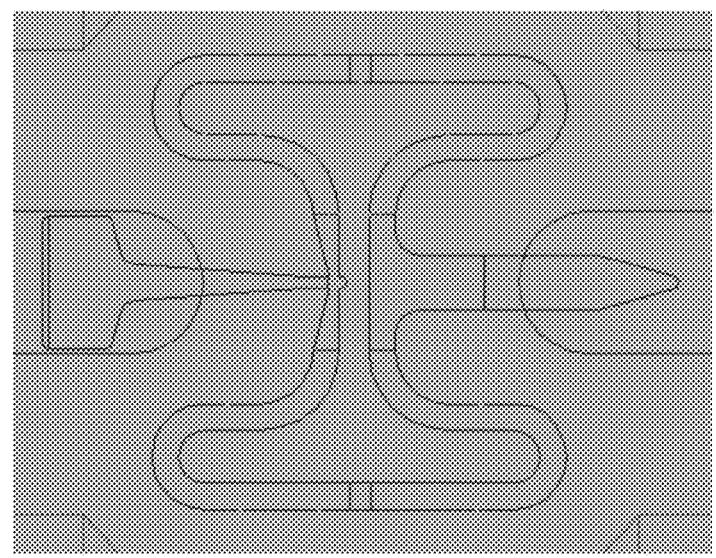

FIG. 3B shows a micrograph 210-*b* of a capture configuration, such as capture configuration 210-*a* of FIG. 3A. Of particular note, a cell 337 is shown captured at capture site 335 and/or in capture nest 330.

FIGS. 3C-3K show different capture configurations 210-*k*-*c*, 210-*k*-*d*, 210-*k*-*e*, 210-*k*-*f*, 210-*k*-*g*, 210-*k*-*h*, 210-*k*-*i*, 210-*k*-*j*, and/or 210-*k*-*k* in accordance with various embodiments. These capture configurations 210-*k* may in general include a capture nest (or capture site), a drain, and/or one or more bypass channels.

Figure 4:
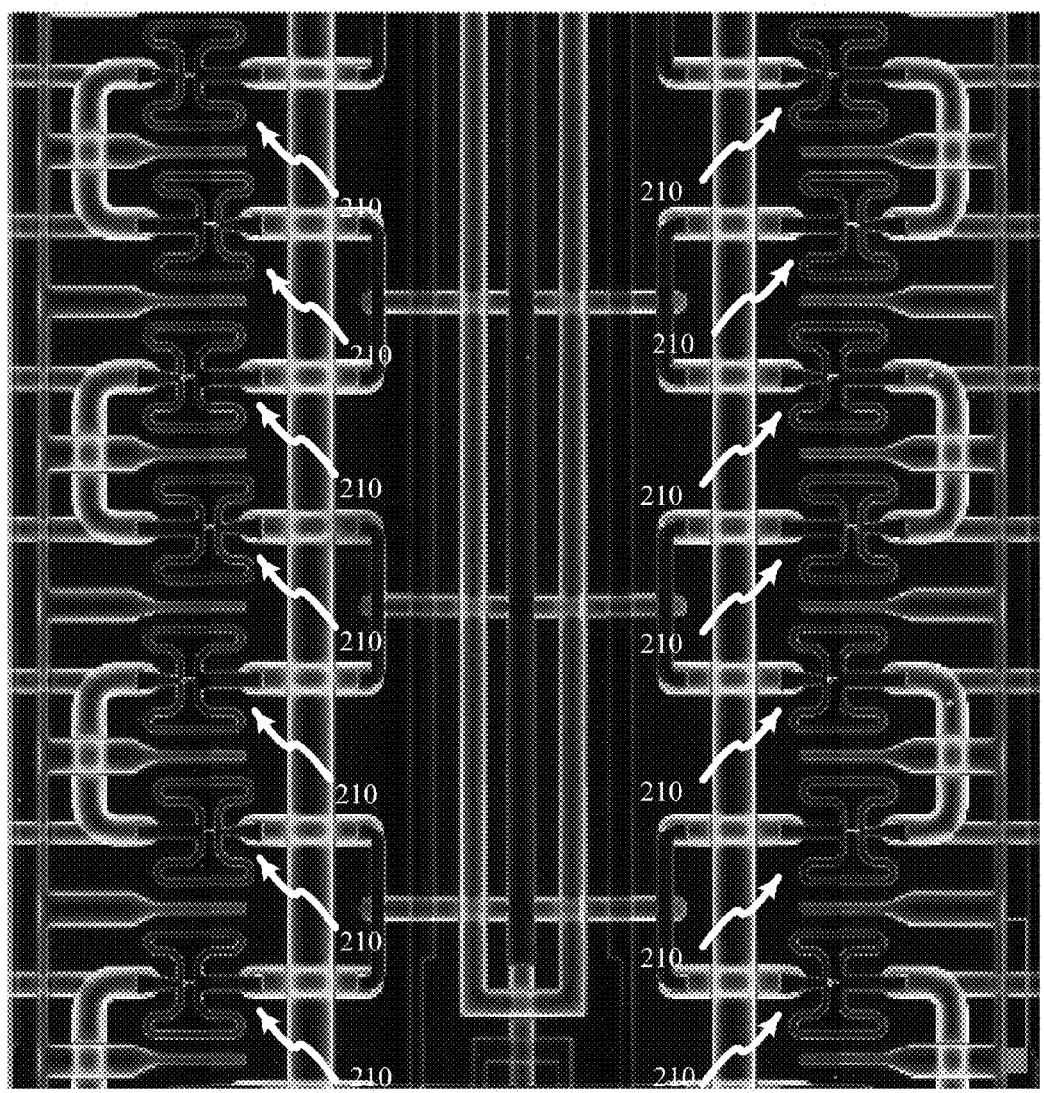
FIG. 4 shows a micrograph of multiple capture configurations coupled in a series of a microfluidic device in accordance with various embodiments.

FIG. 4 shows a micrograph of a system 400 of multiple capture configurations 210. Capture configurations 210 are shown coupled in series, or daisy chained, in accordance with various embodiments. System 400 may be an example of aspects of microfluidic device 110 of FIG. 1 and/or microfluidic device 110-*a* of FIG. 2.

Different considerations may be taken into account when designing capture configurations 210 as part of a microfluidic device 110. For example, cells in the center of the flow-stream may be captured most efficiently. This may influence the design of input channels, such as input channel 310 of FIG. 3A or FIG. 3B. Shorter drain channels, such as drain 340 of FIG. 3A or FIG. 3B, may capture more efficiently. In some cases, small cells may squeeze through the capture drain 340. In some embodiments, a narrower focus channel or input channel 310 may raise efficiency. Deep capture nests 330 may capture multiple cells, while cells caught in shallow capture nests 330 may dislodge easily. In some embodiments, efficiency may be achieved where diameter of stagnation point or capture site 335 may be approximate 1.5 times the diameter to individual cells to be captured. Flow ratio through the drain may be adjusted in some embodiments to facilitate capturing the individual cells.

Figure 5A:
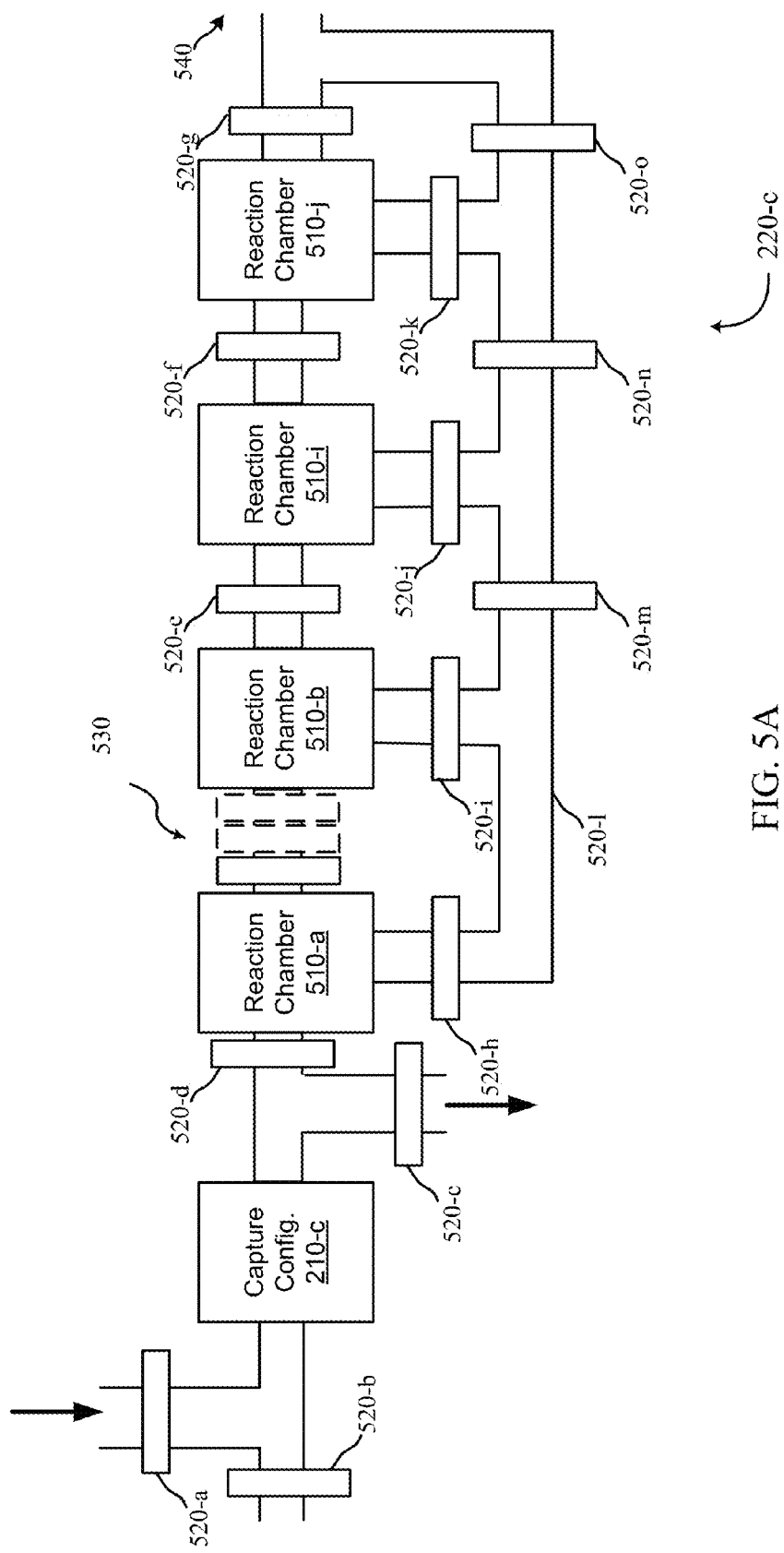
FIG. 5A shows a diagram of a multi-chamber reaction configuration of a microfluidic device in accordance with various embodiments.

FIG. 5A shows an example of a multi-chamber reaction configuration 220-*c* in accordance with various embodiments. Multi-chamber reaction configuration 220-*c* may be an example of a multi-chamber reaction configuration 220 of FIG. 2. FIG. 5A also shows a capture configuration 210-*c* that may be coupled with multi-chamber reaction configuration 220-*c*. Multi-chamber reaction configuration 220-*c* may include different components or aspects in accordance with various embodiments. Multi-chamber reaction configuration 220-*c* may be configured to perform different processes including, but not limited to, STA, RT-STA, mRNA-SEQ, preamplification, WMA, multimodal applications, protein applications, sample processor applications, WTA, WGA, real-time PCR preparation, CNV, and/or haplotyping. Multi-chamber reaction configuration 220-*c* may be configured to perform multiple reaction steps, which may include active mixing.

Multi-chamber reaction configuration 220-*c* may include numerous valves 520, which may be utilized to control the flow of solutions through multi-chamber reaction configuration 220-*c*. In some embodiments, a pump 530, such as a peristaltic pump, may be included in multi-chamber reaction configuration 220-*c* to facilitate transport of solutions through multi-chamber reaction configuration 220-*c*. Pump 530 may include multiple valves 520; in this example, pump 530 may include three valves. One or more pumps 530 may be located at different locations.

Multi-chamber reaction configuration 220-*c* may also include multiple reaction chambers 510. In some embodiments, capture configuration 210-*c* may be considered one of the reaction chambers 510. Merely by way of example, valves 520-*d*, 520-*e*, 520-*f*, and 520-*g* may be utilized to control the direct flow between reaction chambers 510-*a*, 510-*b*, 510-*i*, and 510-*j* respectively. Additional valves such as valves 520-*h*-520-*o*, in different combinations, may be utilized to mix and/or circulate solutions from one or more reaction chamber 510. Additional valves 520-*a* and/or 520-*b* may control flow between different capture configurations. Valve 520-*b* may be utilized to control flow of solutions such as reagents to capture configuration 210-*c*. Multi-chamber reaction configuration 220-*c* may be configured to mix and/or circulate solution during thermal cycling. Reaction products may be delivered 540 to export configuration (not shown) may be referred to as a harvest configuration, harvest well, and/or harvest inlet in some cases.

Figure 5B:
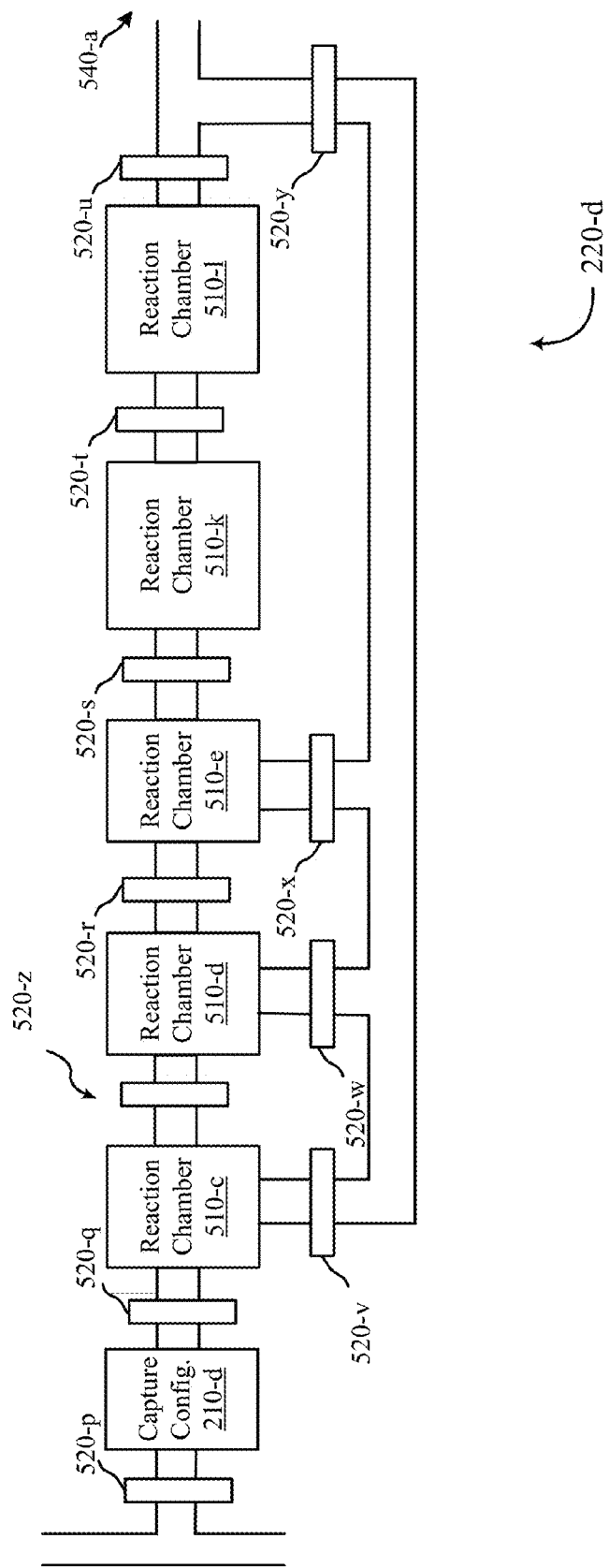
FIG. 5B shows a diagram of a multi-chamber reaction configuration of a microfluidic device in accordance with various embodiments.

FIG. 5B shows another example of a multi-chamber reaction configuration 220-*d* in accordance with various embodiments. Multi-chamber reaction configuration 220-*d* may be an example of a multi-chamber reaction configuration 220 of FIG. 2 and/or multi-chamber reaction configuration 220-*c* of FIG. 5A. FIG. 5B also shows a capture configuration 210-*d* that may be coupled with multi-chamber reaction configuration 220-*d*. Multi-chamber reaction configuration 220-*d* may include different components or aspects in accordance with various embodiments. Multi-chamber reaction configuration 220-*d* may be configured to perform different processes including, but not limited to, STA, RT-STA, mRNA-SEQ, preamplification, WMA, multimodal applications, protein applications, sample processor applications, WTA, WGA, real-time PCR preparation, CNV, and/or haplotyping. Multi-chamber reaction configuration 220-*d* may be configured to perform multiple reaction steps, which may include active mixing.

Multi-chamber reaction configuration 220-*d* may include numerous valves 520, which may be utilized to control the flow of solutions through multi-chamber reaction configuration 220-*d*. Some embodiments may include one or more pumps as part of multi-chamber reaction configuration 220-*d* to facilitate transport of solutions through multi-chamber reaction configuration 220-*d*. For example, valve 520-*z* may include multiple valves 520 to form a peristaltic pump. One or more pumps may be located at different locations.

Multi-chamber reaction configuration 220-*d* may also include multiple reaction chambers 510. In some embodiments, capture configuration 210-*d* may be considered one of the reaction chambers 510. Merely by way of example, valves 520-*p*, 520-*q*, 520-*z*, 520-*s*, 520-*t*, and/or 520-*u* may be utilized to control the direct flow between reaction chambers 510-*c*, 510-*d*, 510-*e*, 510-*k* and/or 510-*l* respective. Additional valves such as valves 520-*v*, 520-*w*, 520-*x*, and/or 520-*y*, in different combinations, may be utilized to mix and/or circulate solutions from one or more reaction chambers 510. Additional valves 520 may control flow between different capture configurations. Valve 520-*p* may be utilized to control flow of solutions such as reagents to capture configuration 210-*d*. Multi-chamber reaction configuration 220-*d* may be configured to mix and/or circulate solution during thermal cycling. Reaction products may be delivered 540 to export configuration (not shown) may be referred to as a harvest configuration, harvest well, and/or harvest inlet in some cases.

Furthermore, reaction chambers 510 and/or capture configuration 210-*d* include a variety of sizes or volumes. In one embodiment, capture configuration 210-*d* may be 4.5 nl, reaction chamber 510-*c* may be 9 nl, reaction chamber 510-*d* may be 9 nl, reaction chamber 510-*e* may be 9 nl, reaction chamber 510-*k* may be 135 nl, and/or reaction chamber 510-*l* may be 135 nl.

Figure 5C:
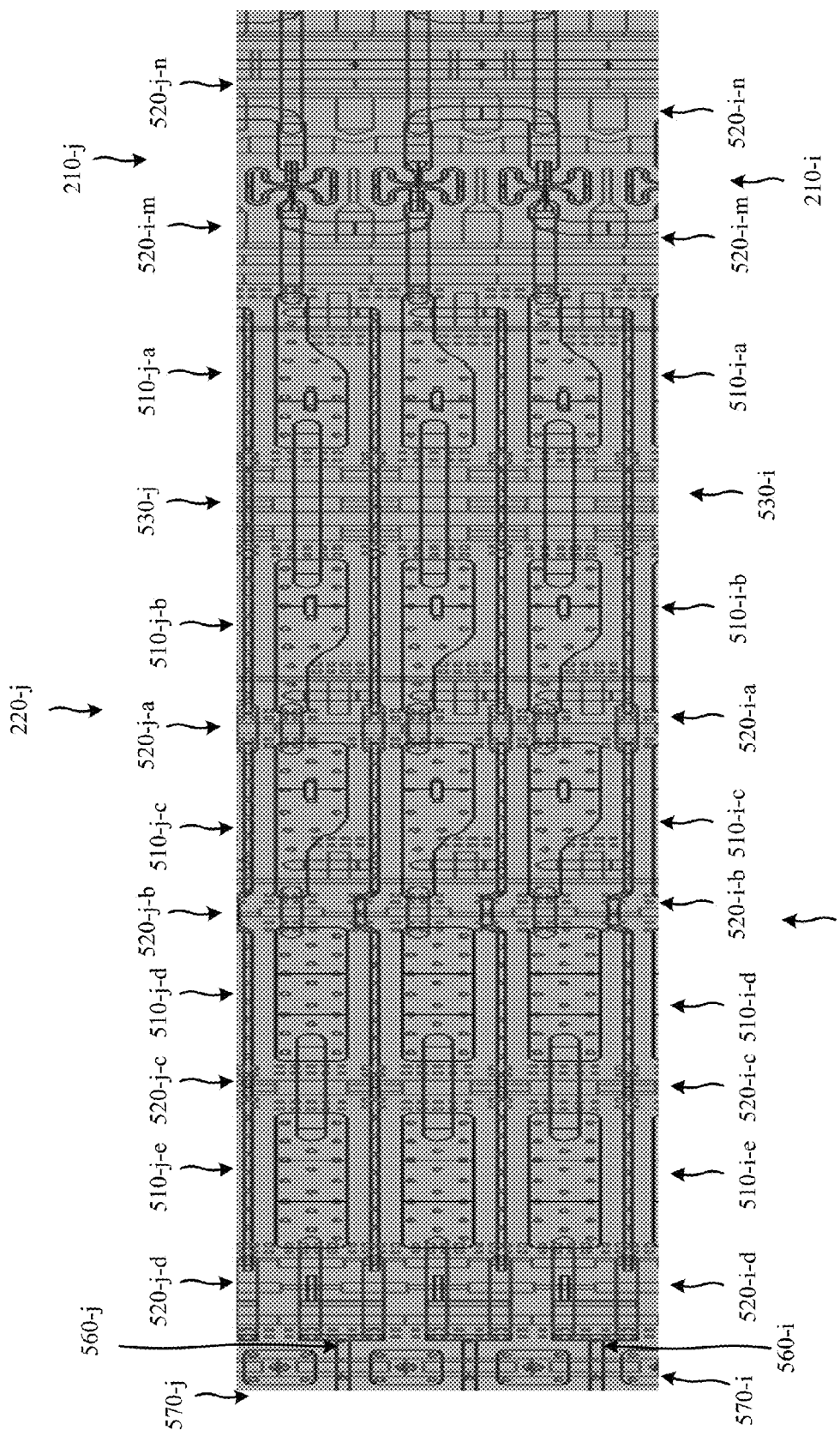
FIG. 5C shows a diagram of several multi-chamber reaction configurations of a microfluidic device in accordance with various embodiments.

FIG. 5C shows an example of a several multi-chamber reaction configurations 220-*i*, 220-*j* in accordance with various embodiments. Multi-chamber reaction configuration 220-*i*/220-*j* may be examples of a multi-chamber reaction configuration 220 of FIG. 2. FIG. 5C also shows capture configuration 210-*i*/210-*j* that may be coupled with multi-chamber reaction configuration 220-*i*/220-*j*. Multi-chamber reaction configuration 220-*i*/220-*j* may include different components or aspects in accordance with various embodiments. Multi-chamber reaction configuration 220-*i*/220-*j* may be configured to perform different processes including, but not limited to, STA, RT-STA, mRNA-SEQ, preamplification, WMA, multimodal applications, protein applications, sample processor applications, WTA, WGA, real-time PCR preparation, CNV, and/or haplotyping. Multi-chamber reaction configuration 220-*c* may be configured to perform multiple reaction steps, which may include active mixing.

Multi-chamber reaction configuration 220-*i*/220-*j* may include numerous valves 520-*i*/520-*j*, which may be utilized to control the flow of solutions through multi-chamber reaction configuration 220-*i*/220-*j*. In some embodiments, a pump 530-*i*/530-*j*, such as a peristaltic pump, may be included in multi-chamber reaction configuration 220-*i*/220-*j* to facilitate transport of solutions through multi-chamber reaction configuration 220-*i*/220-*j*. Pump 530-*i*/530-*j* may include multiple valves; in this example, pump 530-*i*/530-*j* may include three valves. One or more pumps 530-*i*/530-*j* may be located at different locations.

Multi-chamber reaction configuration 220-*i*/220-*j* may also include multiple reaction chambers 510-*i*-*a*, 510-*i*-*b*, 510-*i*-*c*, 510-*i*-*d*, 510-*i*-*e*, 510-*j*-*a*, 510-*j*-*b*, 510-*j*-*c*, 510-*j*-*d*, 510-*j*-*e*. In some embodiments, capture configuration 210-*i*/210-*j* may be considered one of the reaction chambers 510-*i*/510-*j*. Merely by way of example, valves 520-*i*-*a*, 520-*i*-*b*, 520-*i*-*c*, and 520-*i*-*d* may be utilized to control the direct flow between reaction chambers 510-*i*-*a*, 510-*i*-*b*, 510-*i*-*c*, and 510-*i*-*d* respectively. Similarly, valves 520-*j*-*a*, 520-*j*-*b*, 520-*j*-*c*, and 520-*j*-*d* may be utilized to control the direct flow between reaction chambers 510-*j*-*a*, 510-*j*-*b*, 510-*j*-*c*, and 510-*j*-*d* respectively. Additional valves such as valves 520-*i*/520-*j* in different combinations, may be utilized to mix and/or circulate solutions from one or more reaction chamber 510-*i*/510-*j*. Additional valves 520-*i*-*m* and/or 520-*j*-*m* may control flow between different capture configurations. Valve 520-*i*-*n*/520-*j*-*n* may be utilized to control flow of solutions such as reagents to capture configuration 210-*i*/210-*j*. Multi-chamber reaction configuration 220-*i*/220-*j* may be configured to mix and/or circulate solution during thermal cycling. Reaction products may be delivered export channels 560-*i*/560-*j* may be referred to as a harvest configuration, harvest well, and/or harvest inlet in some cases. Some embodiments may include hydration chambers 570-*i*/570-*j*.

Some embodiments utilize a single-cell capture technique utilizing limiting dilution to capture cells in separate reaction volumes. In this type of capture, there may be no use of any capture feature, such as binding affinity or a mechanical feature(s), e.g., in a microfluidic device, that preferentially retains only a single cell at a capture site. For example, limiting dilution can be carried out by preparing a series of dilutions of a cells suspension, and distributing aliquots from each dilution into separate reaction volumes. The number of cells in each reaction volume is determined, and the dilution that produces the highest fraction of reaction volumes having only a single cell is then selected and used to capture cells for the parameter measurements described herein.

In some embodiments, the methods entail the use of an capture technique to increase the expected fraction of separate reaction volumes having only one cells above that achieved using a method such as limiting dilution (i.e., above about 33 percent). In variations of these embodiments, capturing is optimized such that the expected fraction of separate reaction volumes with only one cell each is at least about 35 percent, at least about 40 percent, at least about 45 percent, at least about 50 percent, at least 15 about 55 percent, at least about 60 percent, at least about 65 percent, at least about 70 percent, at least about 75 percent, at least about 80 percent, at least about 85 percent, at least about 90 percent, or at least about 95 percent of the total number of separate reaction volumes. In specific embodiments, the expected fraction of separate reaction volumes with only one cell each falls within a range bounded by any two percentages listed above. The expected fraction of separate reaction volume with only one cell each can be determined by empirical or statistical means, depending on the particular capture technique (e.g., limiting dilution produces reaction volumes having only one cell in a manner consistent with the Poisson distribution). Some embodiments take some measure to increase the expected fraction of separate reaction volumes with only one cell above about 33 percent. In particular embodiments, optimized single-cell capture can be achieved, for example, using a size-based mechanism that excludes retention of more than one cell at in each reaction volume (capture site).

Figure 6:
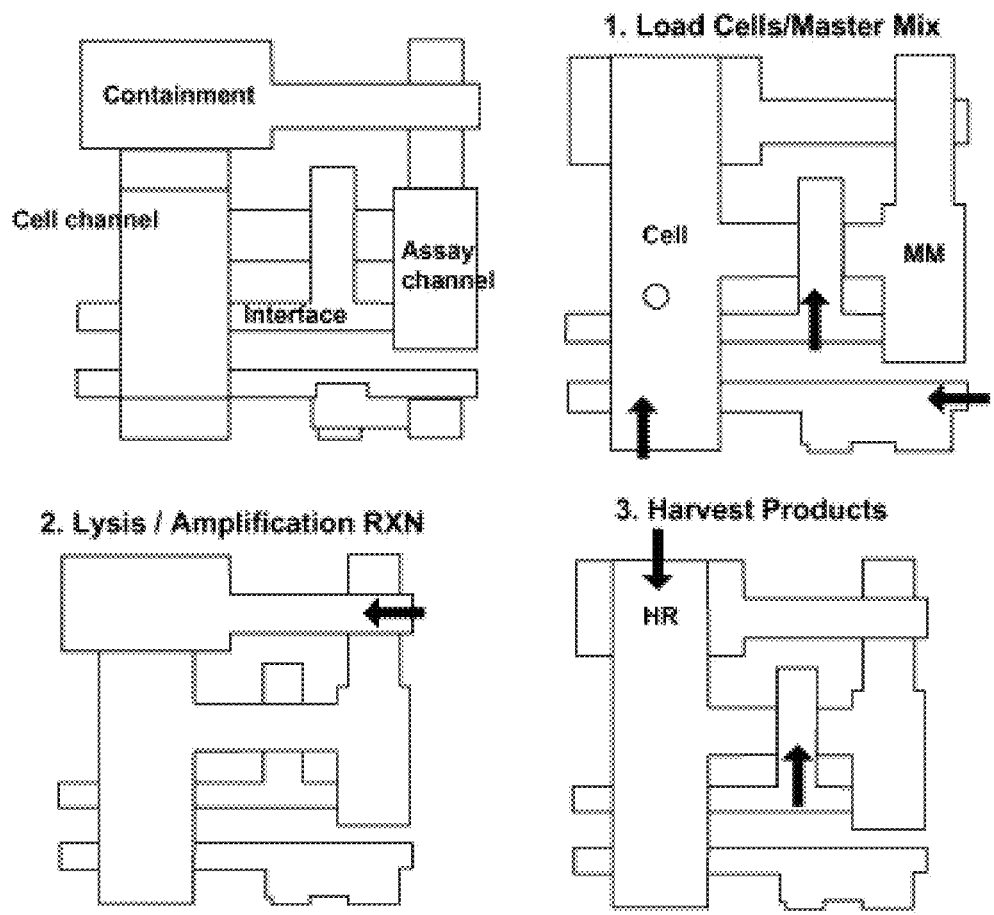
FIG. 6 shows a schematic diagram of the unit cell architecture for a microfluidic device adapted for cell handling based on limiting dilution and/or stochastic capture in accordance with various embodiments.

FIG. 6 shows a schematic diagram of the unit cell architecture for a microfluidic device adapted for cell handling based on limiting dilution and/or stochastic capture, showing on-chip processes. For single-cell analysis, microfluidic devices can be designed to facilitate loading and capture of the particular particles to be analyzed. FIG. 6 shows a unit cell or capture architecture for an illustrative microfluidic device for analyzing cells, such as mammalian cells. Each unit cell may have a "cell channel" (i.e., sample compartment) and an "assay channel" (i.e., assay compartment). The cell channel may be rounded for loading cells, with dimensions on the order of tens microns in diameter to a hundred of several hundred microns in length. Diameters can be about 15 µm, about 20 µm, about 25 µm, about 30 µm, about 35 µm, about 40 µm, or about 45 µm or more, or can fall within a range having any of these values as endpoints, depending on the size of the cells being analyzed. Lengths can be about 60 µm, about 90 µm, about 120 µm, about 150 µm, about 170 µm, about 200 µm, about 230 µm, about 260 µm, about 290 µm or more, or can fall within a range having any of these values as endpoints, depending on the size of the cells being analyzed. In an illustrative microfluidic device, a unit cell for loading cells, such as mammalian cells can be about 30 µm×170 µm. Such a device can be equipped to provide, or to facilitate providing, heat to cell channels after loading to lyse the cells. As shown in FIG. 6, the device can include assay channels separate from cell channels for conducting reactions such as nucleic acid amplification. 170 μm×170 μm containment valves can be used to close cell channels.

Figure 7:
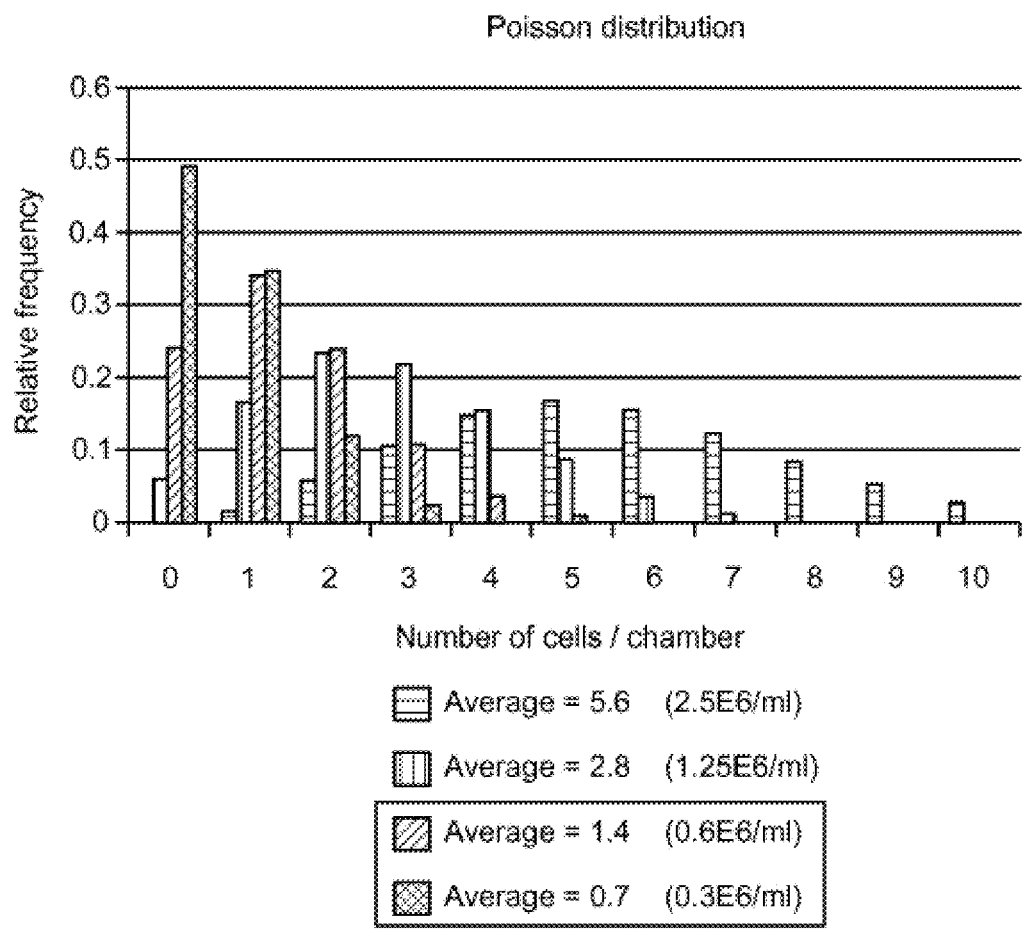
FIG. 7 shows the use of limiting dilution of a cell suspension to obtain a single cell per separate reaction volume in accordance with various embodiments.
Figure 8A:
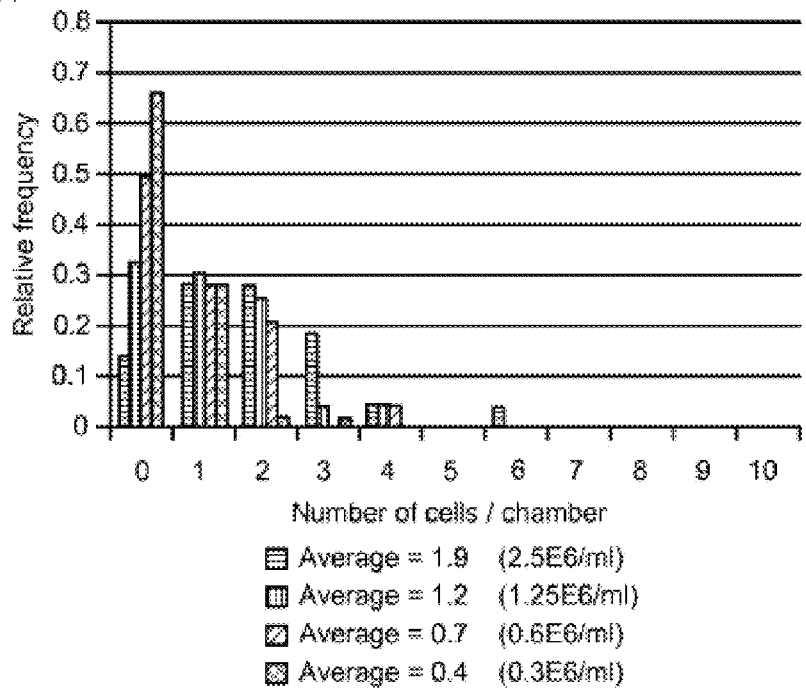
FIG. 8A and FIG. 8B show the results of cell counting in a chip using brightfield to image, as compared to the theoretical distribution in accordance with various embodiments.
Figure 8B:
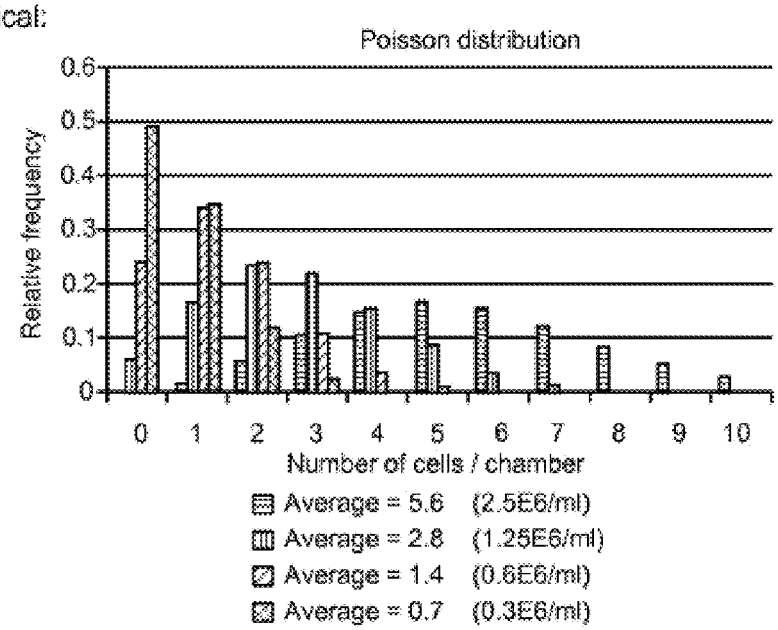
Figure 9:
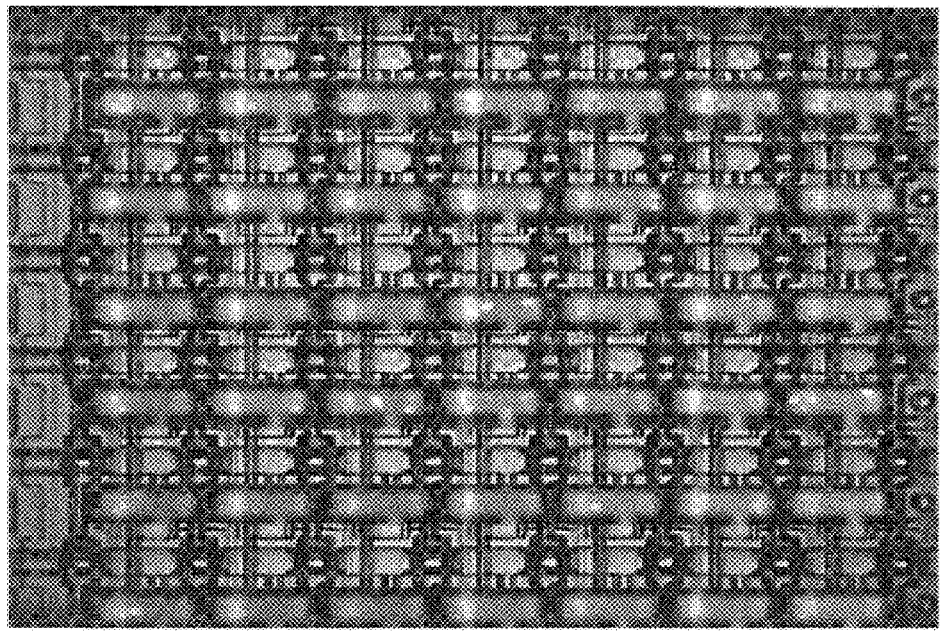
FIG. 9 shows a fluorescent cell "ghost" images permit detection of more cells than pre-PCR brightfield imaging in accordance with various embodiments.
Figure 10:
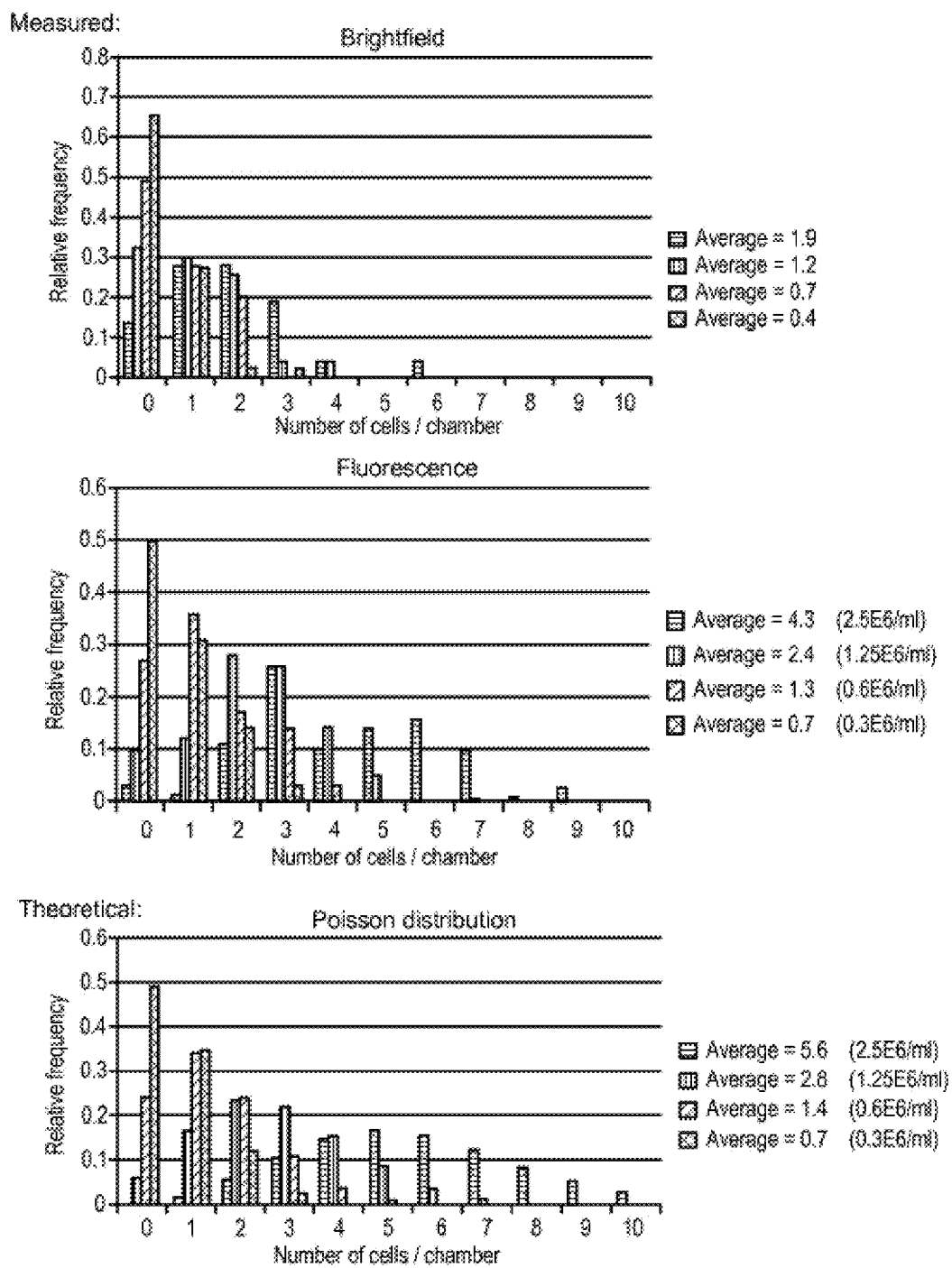
FIG. 10 shows brightfield, fluorescences, and Poisson distributions in accordance with various embodiments.

FIG. 7 shows the use of limiting dilution of a cell suspension to obtain a single cell per separate reaction volume ("chamber" of a microfluidic device or "chip"). The theoretical distribution (Poisson distribution) for various cell densities is shown. FIG. 8A and FIG. 8B show the results of cell counting in a chip using brightfield (FIG. 8A) to image, as compared to the theoretical distribution (FIG. 8B). Cell density in the chip, based on brightfield imaging, is close to, but lower than, the Poisson distribution, with this tendency exacerbated at higher cell densities. FIG. 9 shows a fluorescent cell "ghost" images permit detection of more cells than pre-PCR brightfield imaging, so that the cell density more closely approximates the Poisson distribution shown in FIG. 10.

In certain embodiments, mechanical capture is used alone or in combination with one or more other capture features to preferentially capture a single cell in each separate reaction volume (i.e., each capture site within a microfluidic device). For example, each capture site can include one or more physical barrier(s) sized to contain only one cell. The shape of the physical barrier can be designed to enhance the retention of the cell. For example, the physical barrier(s) can be sized and configured to form a concave surface suitable for retaining just one cell. In such embodiments, the physical barrier(s) can be designed so as to permit the flow of fluid through the capture site, when it is not occupied by a cell, and/or the capture site may include a drain feature that facilitates this flow. In particular embodiments, a micro fluidic device contains a plurality of suitably sized/configured physical barriers, whereby a plurality of individual cells is retained within the device, one cell being retained by each physical barrier. In illustrative embodiments, the physical barriers can be located within separate compartments within a micro fluidic device, one region per compartment. The compartments can be arranged to form an array.

In certain embodiments, affinity-based capture is used alone or in combination with one or more other capture features, e.g., mechanical capture, to capture a single cell in each separate reaction volume (i.e., each capture site within a micro fluidic device). For example, a discrete region of a microfluidic device surface that contains a binding partner for a cell component may be sized so that only one cell can bind to the region, with the binding of subsequent cells blocked by steric hindrance. In particular embodiments, a micro fluidic device contains a plurality of suitably sized regions, whereby a plurality of individual cells, one at each region, is retained within the device. In illustrative embodiments, these regions can be located within separate compartments within a micro fluidic device, one region per compartment. The compartments can be arranged to form an array.

Figure 14A:
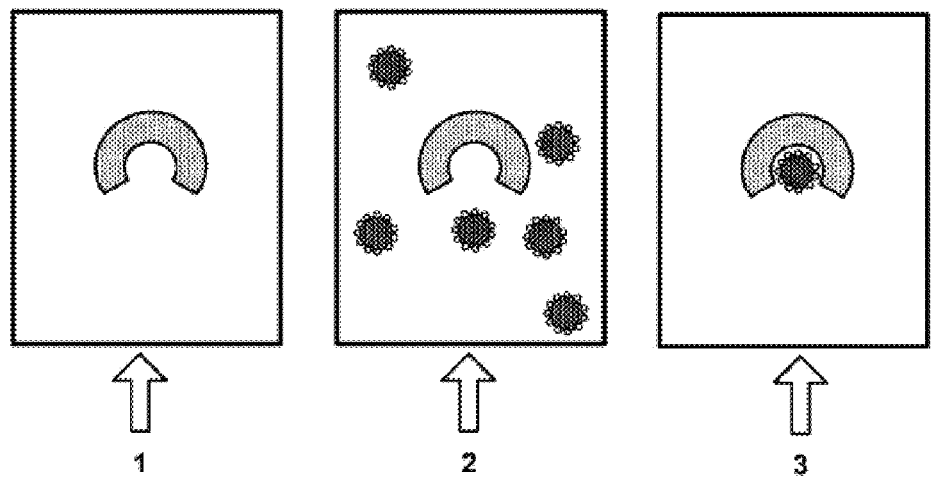
FIG. 14A and FIG. 14B illustrate a strategy for using capture features to catch single, affinity-reagent-coated beads, which then may display the affinity reagent (e.g., antibody) so as to capture single cells in accordance with various embodiments.
Figure 14B:
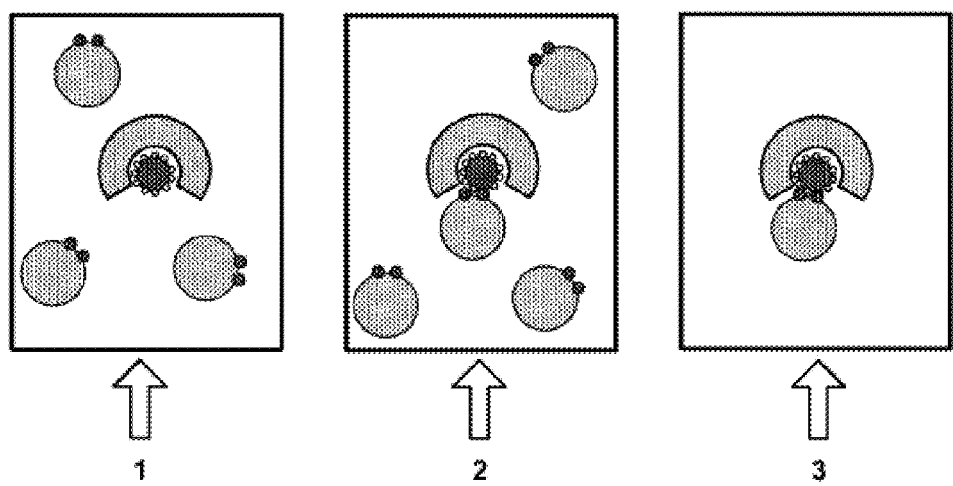

One approach to affinity-based, optimized single-cell capture is based on capturing a support including a binding partner that binds the cell to be assayed. In illustrative embodiments, the support can be a bead that has the binding partner distributed over its surface as shown in FIG. 14A, for example. The bead can be captured by mechanical capture using a cup-shaped capture feature to produce a single immobilized support (e.g., bead) at each capture site. In addition to immobilizing the support, the capture feature can, in certain embodiments, reduce the surface area of the support (e.g., bead) that displays the binding partner. This surface can be sufficiently reduced that only one cell can bind to the area of the immobilized support (e.g., bead) that displays the binding partner. To facilitate cell-support binding, in some embodiments, the area of the immobilized support that displays the binding partners faces the flow path of the cells. In specific, illustrative embodiments, a flow channel of a microfluidic device contains a series of capture features. A suspension of beads bearing binding partners (e.g., cell-specific antibodies) is inputted into the channel to produce a series of immobilized beads at the capture sites. The channel is then washed to remove any free (i.e., non-immobilized) beads as shown in FIG. 14A. A cell suspension may then be input into the channel. An individual cell can bind to the portion of each bead that displays binding partners. Each bound cell may prevent any other cells from binding to the bead through steric occlusion. Washing of the channel may remove unbound cells as shown in FIG. 14B. Valves in between the capture sites can then be closed to create separate reaction volumes, each containing one capture site with one bound cell. One or more focusing features can be employed to direct bead, as well as, cell flow toward each capture site. Alternatively or in addition, the capture features can each include a drain feature that permits the flow of fluid through the capture site when the capture feature is not occupied by a bead.

Figure 11A:
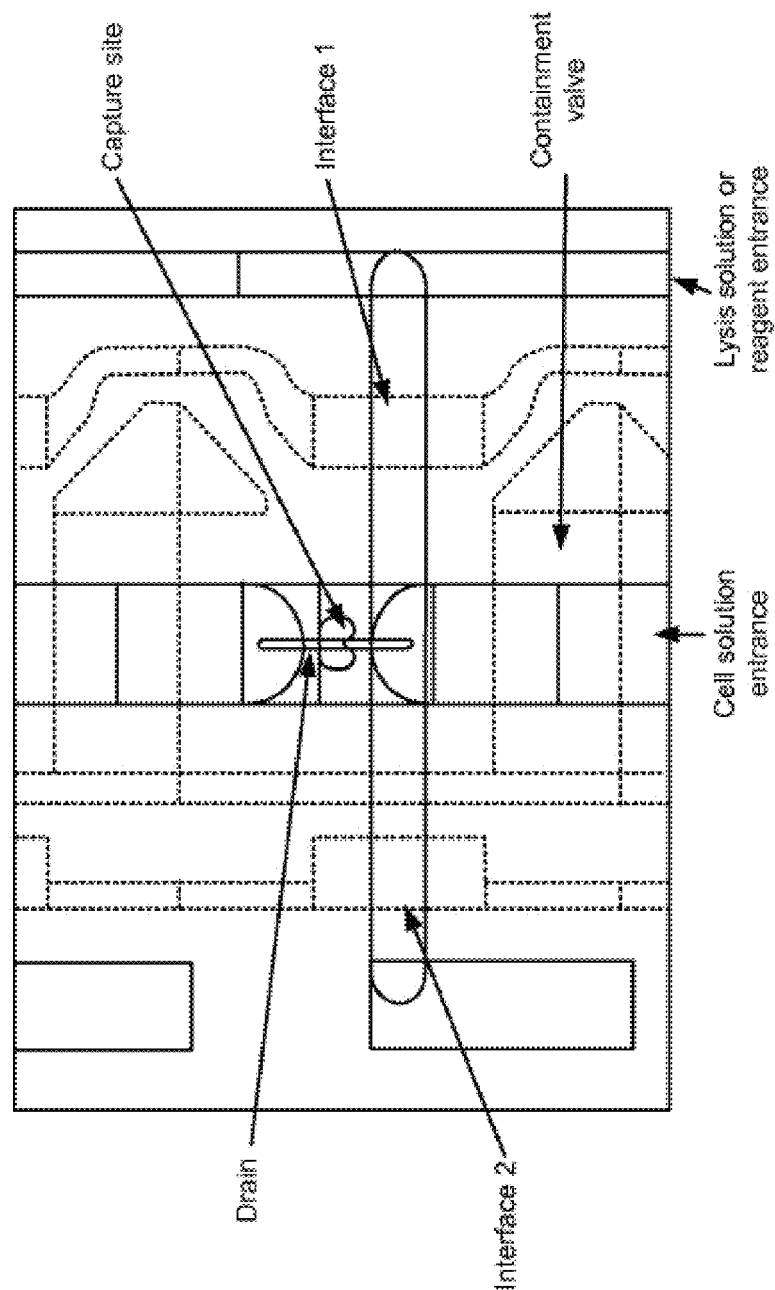
FIG. 11A and FIG. 11B illustrate examples single cell capture configurations sites with a capture feature and drain in accordance with various embodiments.
Figure 11B:
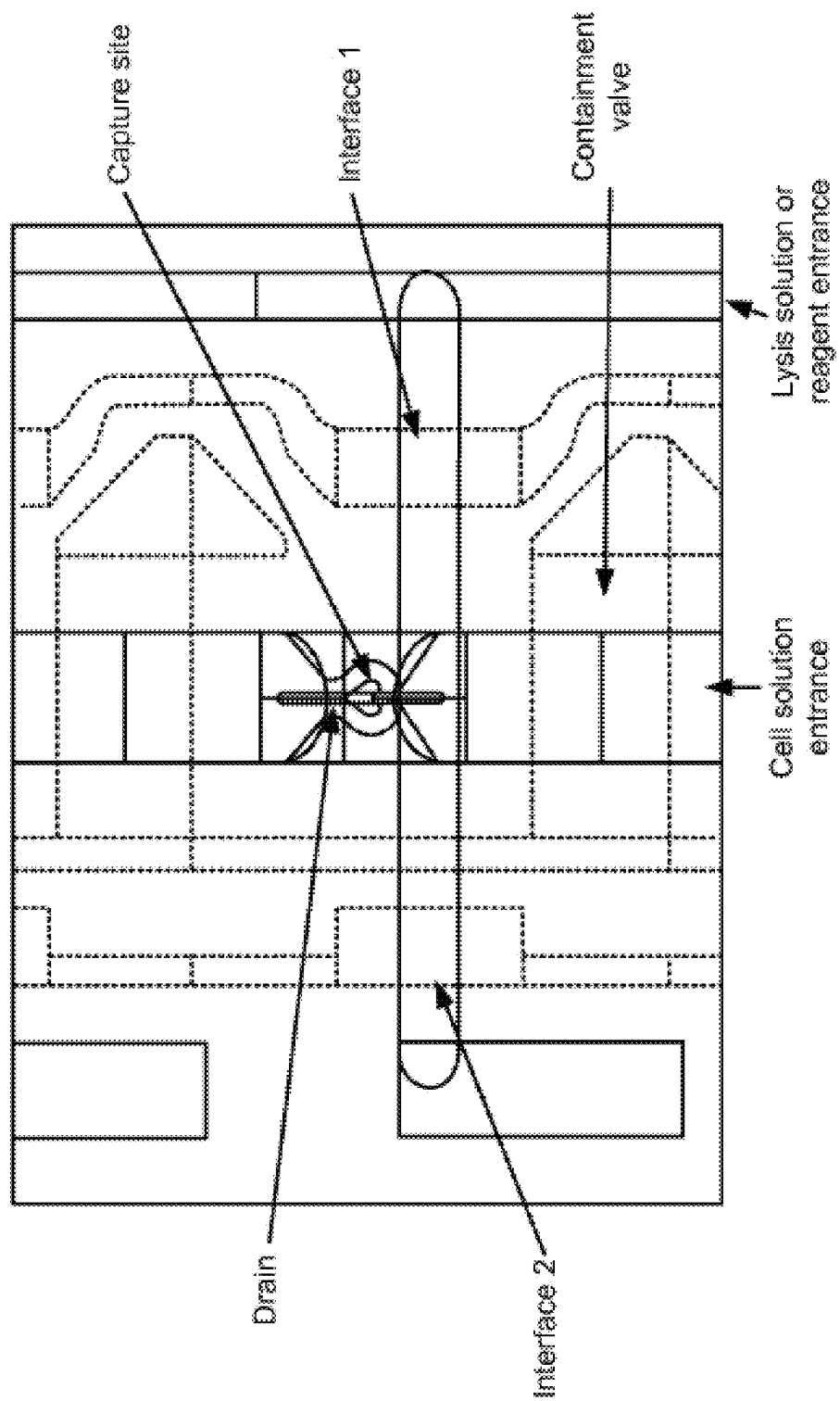
Figure 12:
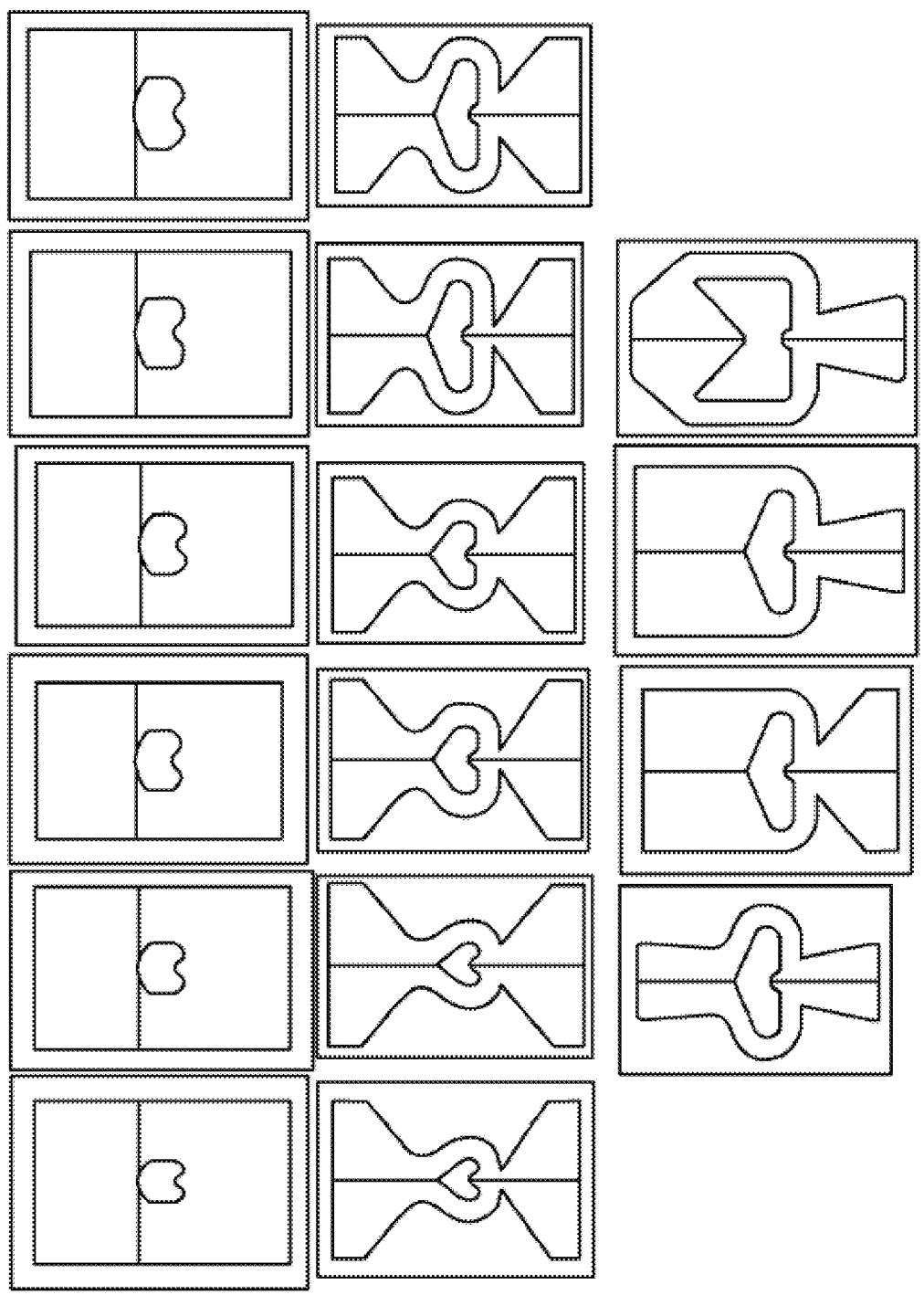
FIG. 12 shows different examples of single cell capture configurations in accordance with various embodiments.

Some embodiments discretely capturing single cells from suspension as they flow through a microfluidic device is to define a microfluidic geometry that guides flow of a suspension of cells (such as cells or beads) over a capture site in a manner that the capture site catches a single cell, efficiently captures single cell (e.g., the probability of the capture of a cell passing near a capture site is high), and/or guides the remaining suspension around the capture site. The geometries can be size-based, i.e., the capture site is just large enough to contain one cell (and no more), but still permit the flow of cell-free suspension through the site at reasonably low fluidic impedance, such that an empty capture site would guide the flow of cells toward it rather than around it. This may be accomplished by the use of a drain. Additional geometries can also focus the flow of cells in a manner that increases the likelihood of cells coming in close enough proximity to the capture site for high probability of successful capture. Variations on these geometries have focused on controlling the flow resistance of the fluidics surrounding the capture site and drain, including the drain itself, as well as varying the aperture of focusing geometry in attempts to position the flow of cells close to the capture site. FIG. 11A and FIG. 11B illustrate examples of single cell capture configurations with capture site with a capture feature and drain. FIG. 11A shows a site without baffles to focus flow, whereas FIG. 11B shows a site with baffles. Additional capture configurations with capture site designs are shown in FIG. 12.

Single-cell studies within micro fluidic architectures may involve the isolation of individual cells into individual reaction partitions (chambers, droplets, cells). Limiting dilution is one method for achieving this isolation. Cells may be loaded at concentrations of less than one cell per partition on average, and distribute into those partitions in a pattern described by Poisson statistics. Another approach is to rely on mechanical traps to capture cells. These traps are designed to capture cells of a given size range. This may result in a biased selection of cells from the population within that size.

For some applications, a capture method may use biological markers expressed on the surface of cells. Antibodies can be patterned in specific locations on a microfluidic device, although this approach may not be simple, depending on the structure of the microfluidic device. Some embodiments include method for capture of single cells based on the initial capture of a single, affinity-reagent-coated bead in a specific location in a microfluidic device. The surface area presented by this bead at the opening of a capture site may provide a defined surface of affinity reagent accessible for cell binding. The bead size and capture site can be chosen/designed such that once a single cell is bound to the bead, the rest of the accessible surface area of the bead is sterically blocked by the first-bound cell. Selection of an appropriate sized bead capture site also provides for capture of a broad range of cell sizes. As long as the cell is larger than the exposed capture area, and expresses the appropriate surface marker or binding partner for the affinity reagent, it should be possible to capture that cell.

Figure 13A:
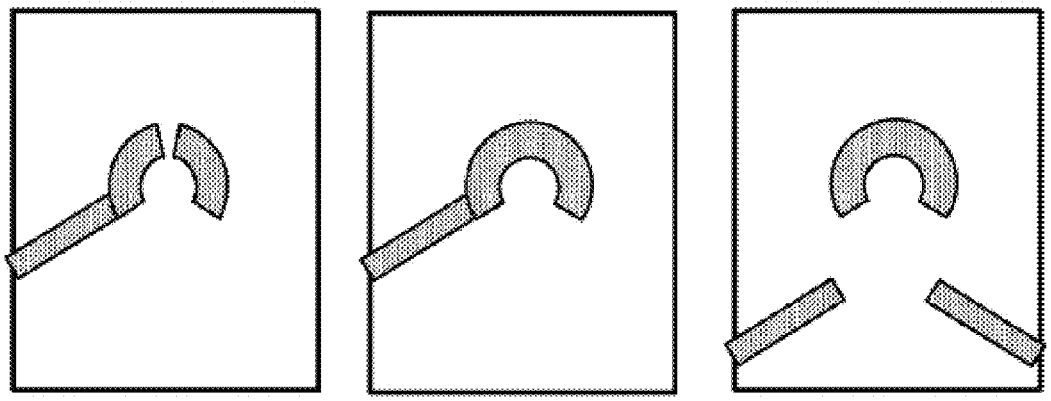
FIG. 13A provides illustrative capture feature different baffle combinations in accordance with various embodiments.
Figure 13B:
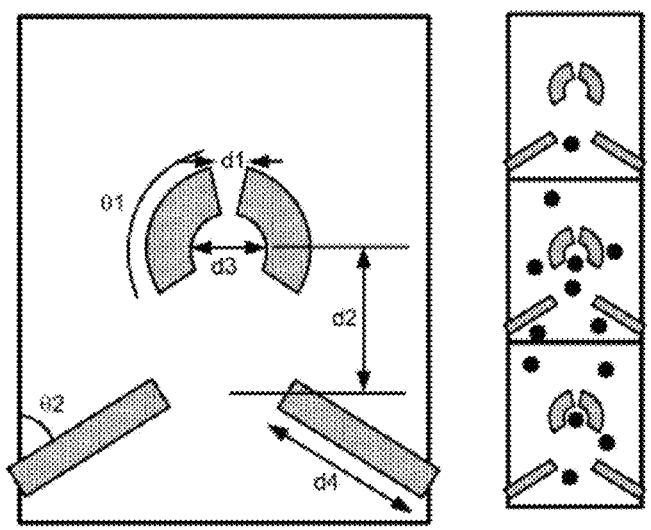
FIG. 13B and FIG. 13C illustrate the variables for, and performance of, different capture feature/baffle combinations in accordance with various embodiments.
Figure 13C:
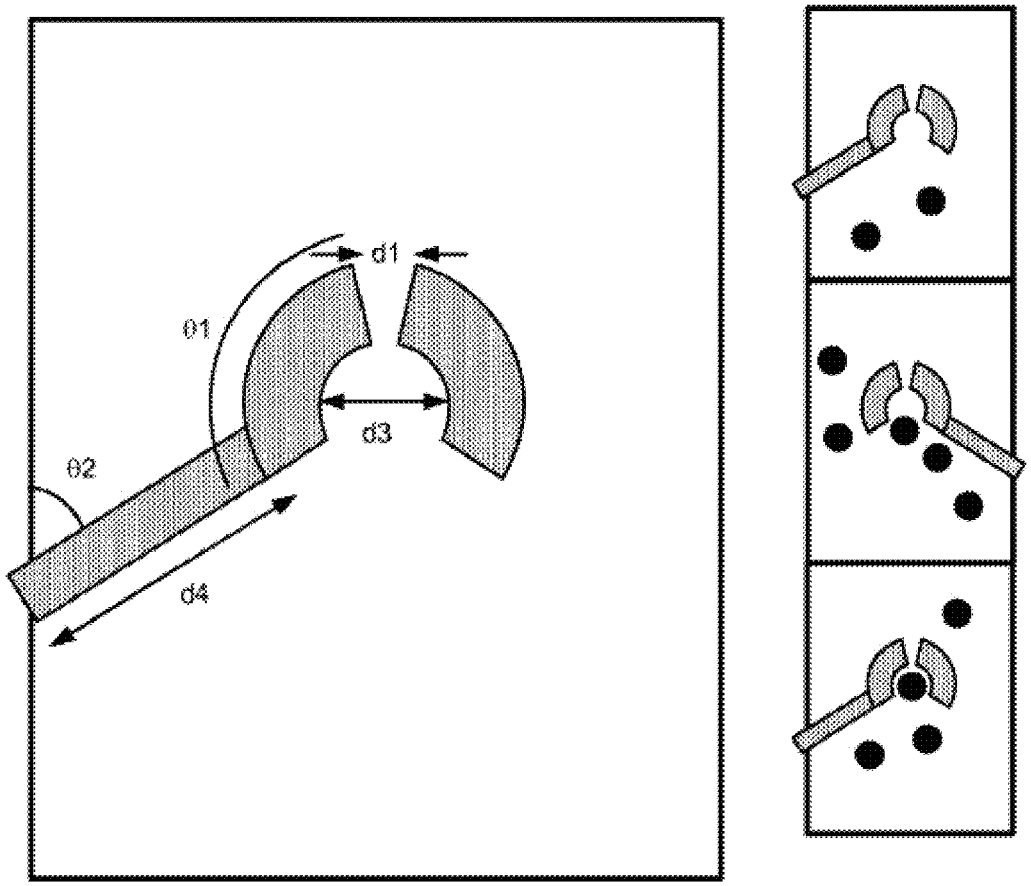

Capture architectures can be designed to maximize the probability that cells will come into contact with the surface markers. For example, baffles on one or more channel walls can be used to direct beads towards capture feature. FIG. 13A provides illustrative capture feature different baffle combinations. Performance of the capture feature can be adjusted by adjusting one or more variables, including angle of baffles, distance of baffles from capture site, length of baffles, size and shape of capture feature, size of drain in capture feature (if present). FIG. 13B and FIG. 13C illustrating the variables for, and performance of, capture feature/baffle combinations. In FIG. 13B, baffles on the channel wall may be used to direct beads towards a capture feature. In FIG. 13C, the capture feature may be coupled to a baffle on a channel wall; individual capture feature/baffle combinations can be located on alternate walls to focus flow towards the adjacent capture feature/baffle combination. These combinations can be located at sites that, in use, are separable (e.g., using valves) to form separate reaction chambers.

FIG. 14A and FIG. 14B illustrate (in simplified form, lacking baffles) a strategy for using capture features to catch single, affinity-reagent-coated beads, which then may display the affinity reagent (e.g., antibody) so as to capture single cells. In FIG. 14A-1, flow may be initiated in a channel containing capture features. In FIG. 14A-2, antibody-bound beads may flow toward the capture features until a bead lodges in the capture feature, as shown in FIG. 14A-3. The channel is then washed to remove non-captured beads. Subsequently, as shown in FIG. 14B-1 bearing a cell-surface marker to which the antibody binds may be flowed into the channel containing the captured beads. FIG. 14B-2 illustrates how cells bearing the marker may interact with and bind to antibodies displayed by the captured bead. The display area may be sized so that a bound cell will inhibit other cells from interacting with the captured bead through steric occlusion, such that only one cell binds to each captured bead. The channel may then be washed to remove non-bound cells, as shown in FIG. 14B-3, leaving one cell immobilized at each capture site.

Figure 15A:
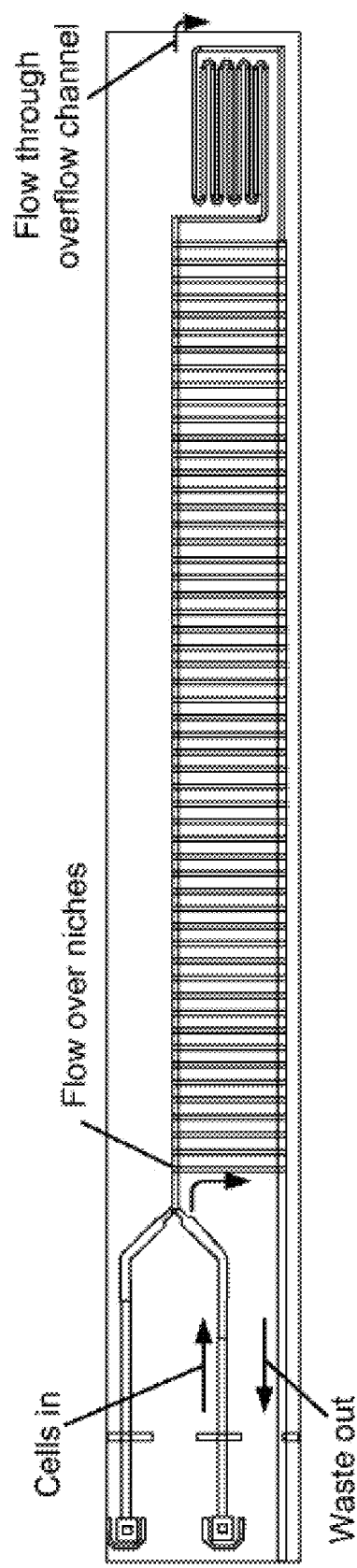
FIGS. 15A-15G shows additional capture configurations for single-cell capture in accordance with various embodiments.
Figure 15B:
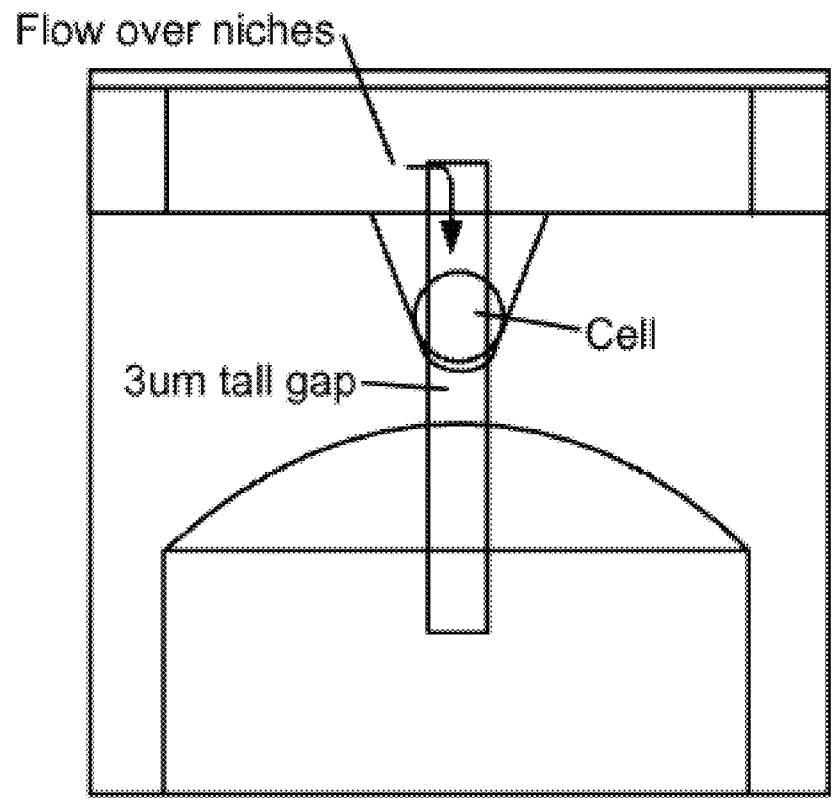
Figure 15C:
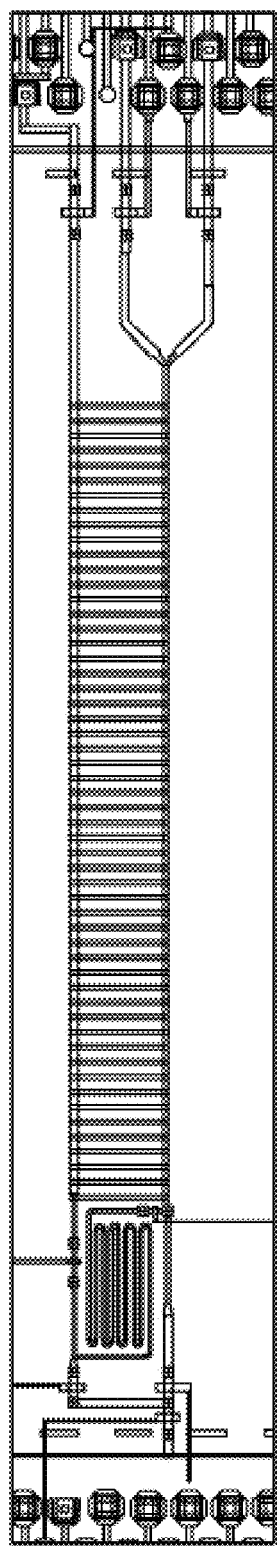
Figure 15D:
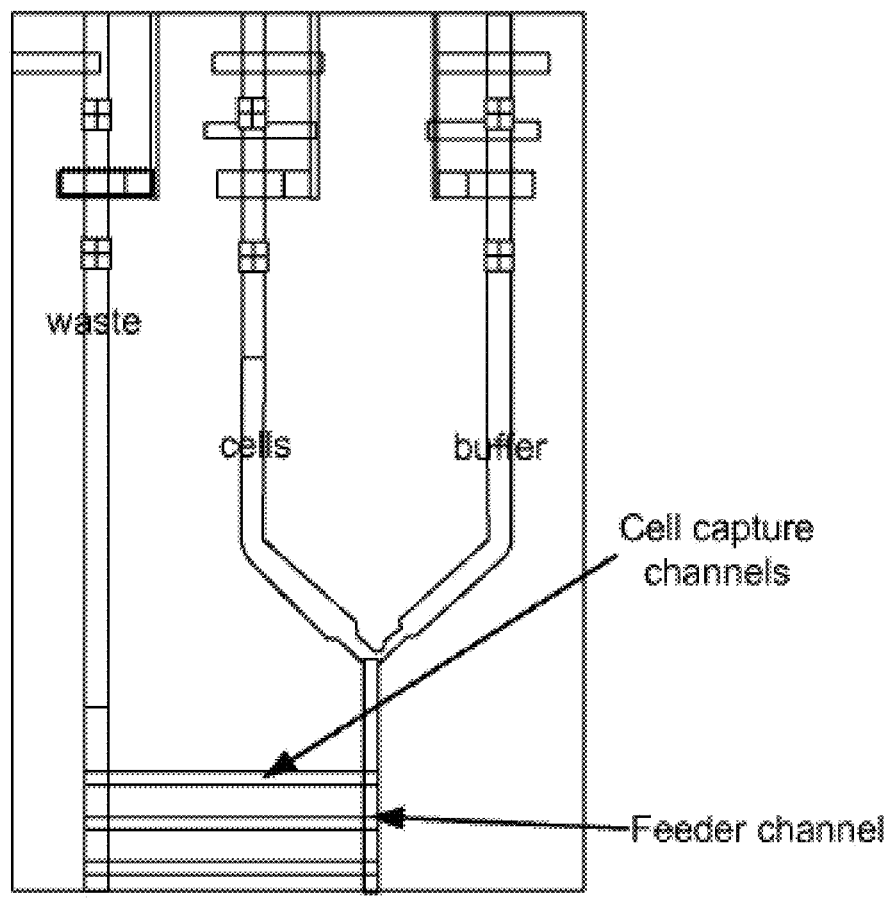
Figure 15E:
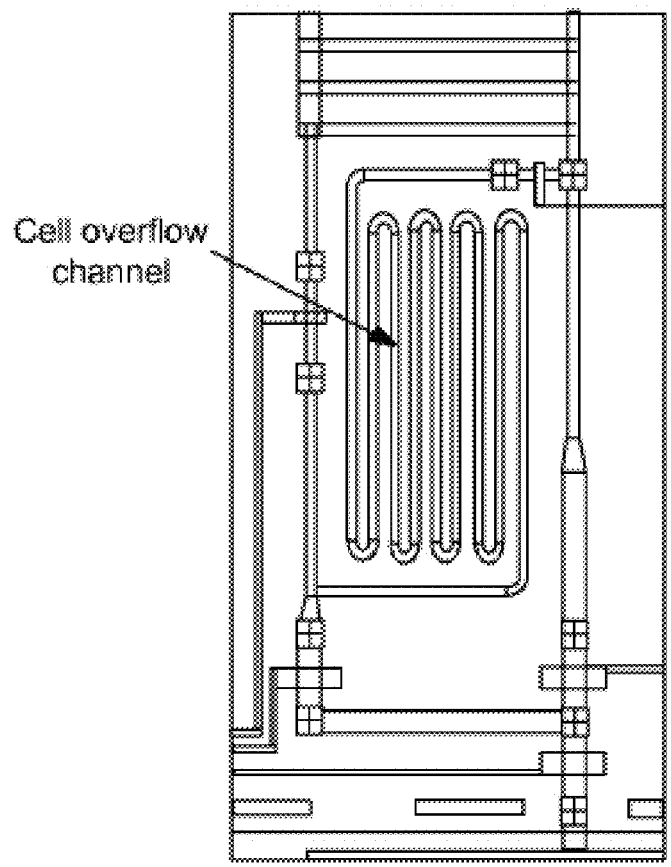
Figure 15F:
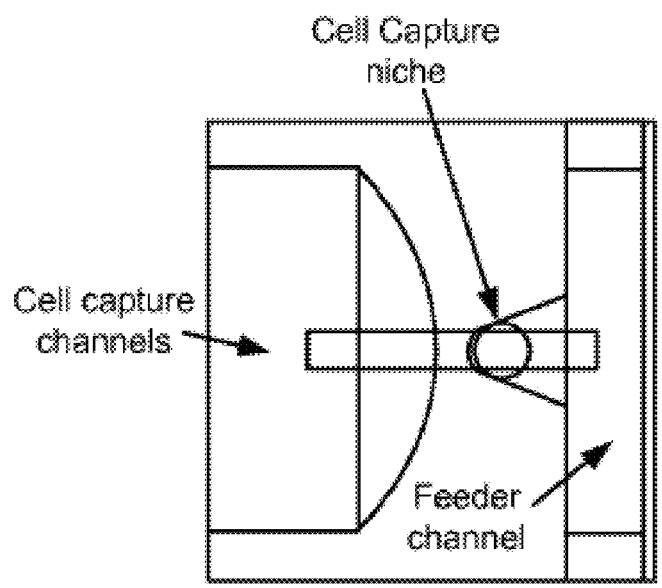
Figure 15G:
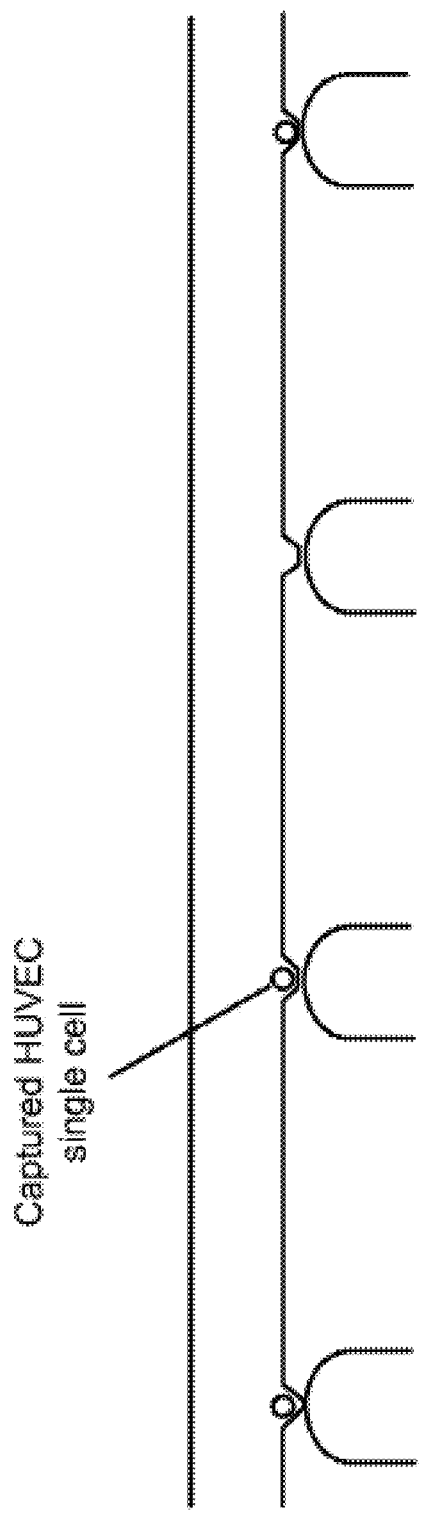

FIG. 15A shows a schematic of a microfluidic device designed to capture single cells at discrete locations (niches). Flow may be designed to be stronger over niches than through an overflow channel. Niches contain small gaps (~3 μm tall); see FIG. 15B, for example. When a cell enters niche, it may block the niche and prevents any more flow into the niche. Flow may pass through next unoccupied niche, until it too may be blocked by a cell. In theory, every niche may capture one cell before cells pass through the overflow channel and out to waste. Referring to FIG. 15C, FIG. 15D, FIG. 15E, FIG. 15F, and FIG. 15G for more detail, a buffer inlet may converge with a cell inlet so as to force cells to a side of a feeder channel that is closest to a series of transverse cell capture channels as shown in FIG. 15D, for example. The resistance of the transverse cell capture channels may be lower than that of a cell overflow channel to induce preferential flow of cells into niches versus into the cell overflow channel, as shown in FIG. 15E. As shown in FIG. 15F, each niche may be large enough to capture just one cell. The niche gape may be sufficiently small that cells may be captured at the operational pressure/flow levels. If the latter may be too high and/or the niche gaps may be too large, cells may deform and may be pushed through the niche gaps. The presence of a cell in a niche may raise the resistance of the particular circuit, and flow may therefore be directed to circuits without cells. FIG. 15G shows an individually captured human umbilical vein endothelial cell (HUVEC) in a niche.

Figure 16:
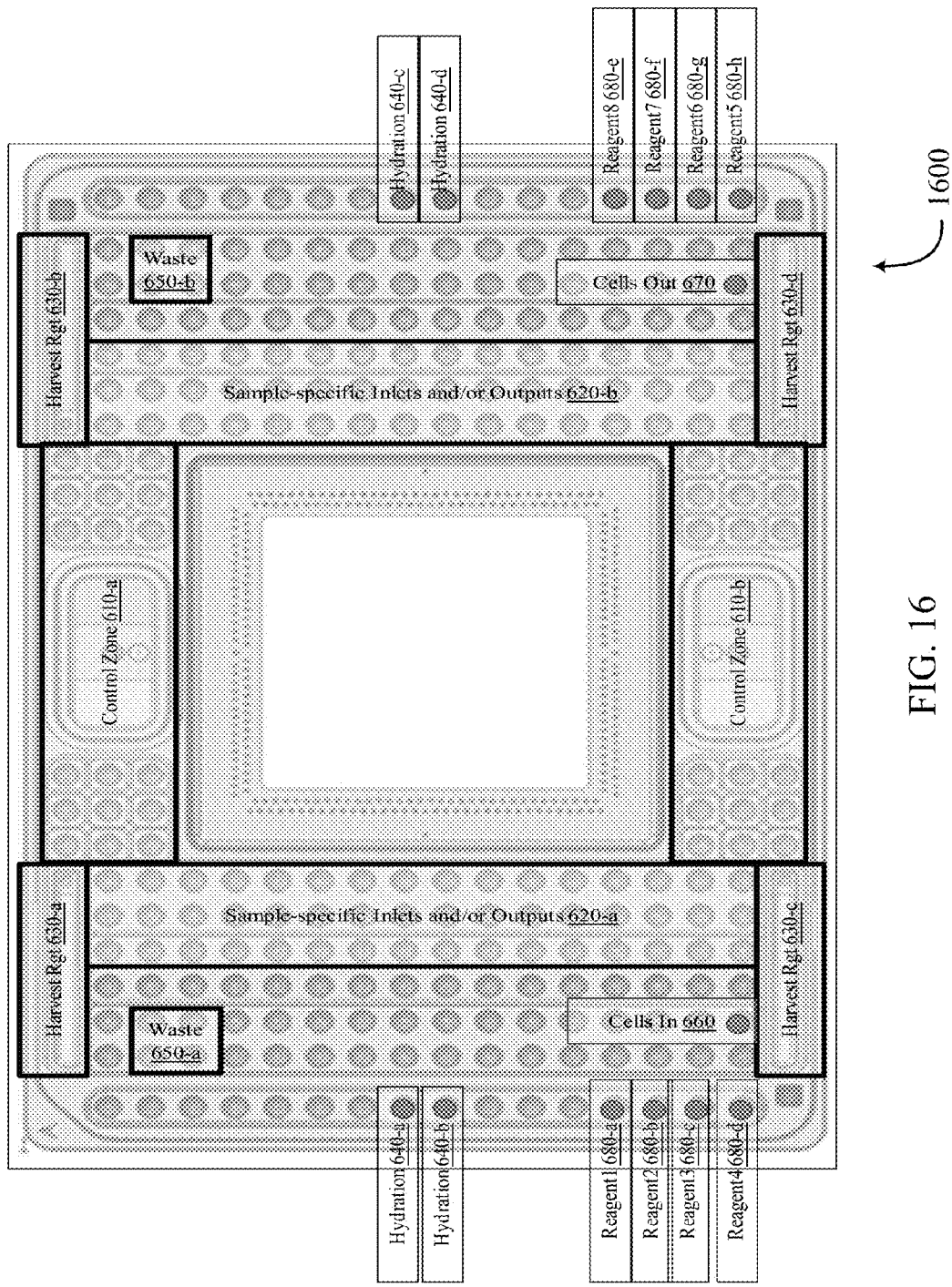
FIG. 16 shows a diagram of a microfluidic carrier in accordance with various embodiments.

FIG. 16 shows an example of a microfluidic device 1600 in accordance with various embodiments. Microfluidic device 1600 may be referred to as a microfluidic carrier and microfluidic chip combination. Microfluidic device 1600 includes numerous ports that may configured for loading and/or exporting products from microfluidic device 1600 and/or controlling the operation of one or more aspects of microfluidic device 1600. Other embodiments may include different configurations. Microfluidic device 1600 may include control zones 610-*a* and 610-*b*, which may be utilized to control pressure with microfluidic device 1600. Microfluidic device 1600 may include sample-specific inlet and/or outputs 620-*a* and/or 620-*b*. Some embodiments may include one or more harvest reagent ports such as 630-*a*, 630-*b*, 630-*c*, and/or 630-*d*. Some embodiments may include one or more hydration ports 640-*a*, 640-*b*, 640-*c*, and/or 640-*d*. Waste ports 650-*a* and/or 650-*b* may be provided. In addition, cell in ports 660 and/or cell out ports 670 may be provided. In addition, one or more reagent ports may be provided such as 680-*a*, 680-*b*, 680-*c*, 680-*d*, 680-*e*, 680-*f*, 680-*g*, and/or 680-*h*. Microfluidic device 1600 may also include a microfluidic chip or device 110-*b*, which may be an example of microfluidic device 110 of FIG. 1 and/or FIG. 2, for example.

Figure 16A:
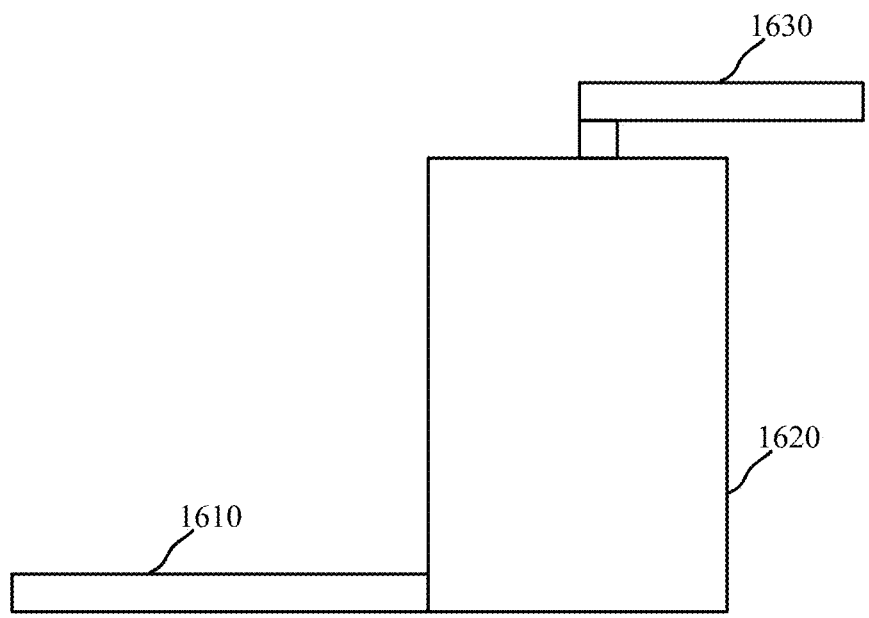
FIG. 16A shows aspects of a microfluidic device in accordance with various embodiments.

FIG. 16A shows an example of aspects of microfluidic device 1600, which may include carrier channels 1610, carrier vias 1620, and/or on-chip channel 1630. In some cases, cell density and/or media density may result in cells sinking. In order to avoid cells falling out of solution in carrier via 1620, some embodiments may utilize Percol. Some embodiments may utilize smaller carrier vias to avoid cells falling out of solution.

Figure 17:
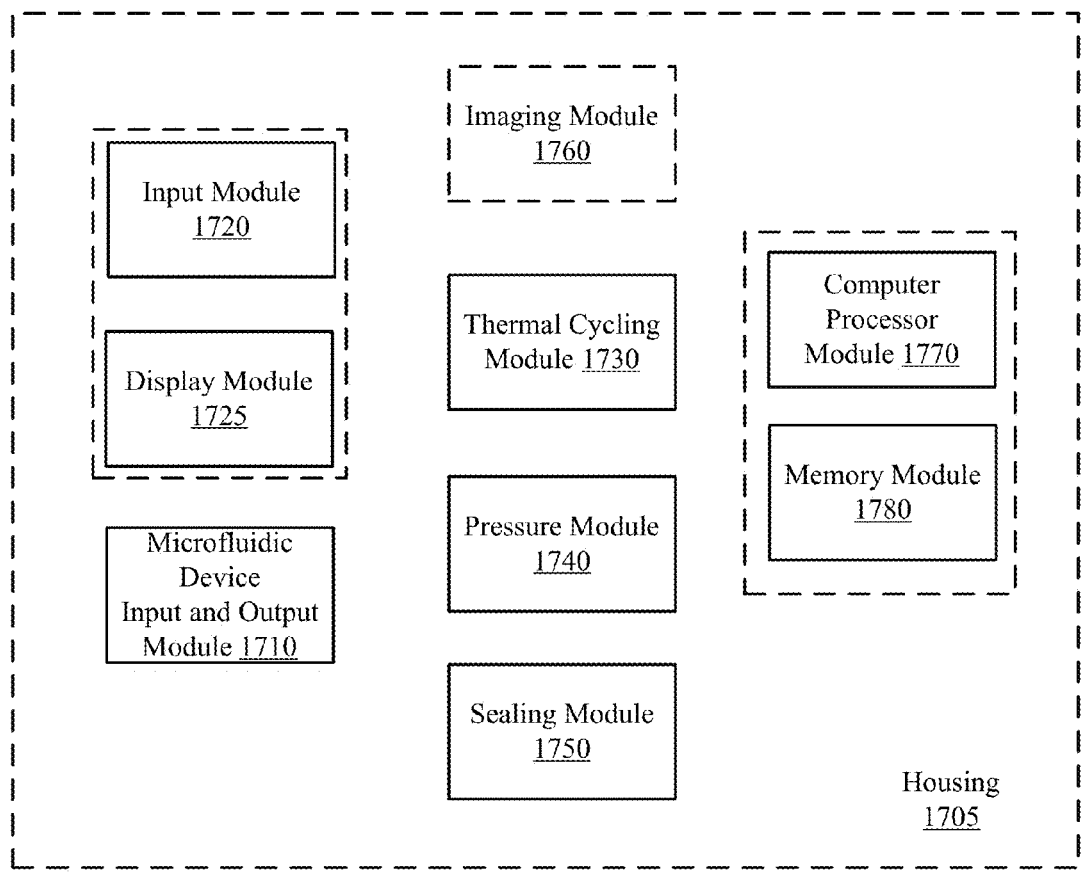
FIG. 17 shows a diagram of a microfluidic controller in accordance with various embodiments.

FIG. 17 shows a microfluidic controller 1700 in accordance with various embodiments. Microfluidic controller 1700 may be an example of microfluidic controller 120 of FIG. 1. Microfluidic controller 1700 may be configured to work with the numerous microfluidic devices disclosed in this application including microfluidic device 110 of FIG. 1 and/or FIG. 2, and/or microfluidic device 1600 of FIG. 16, for example.

Microfluidic controller 1700 may include a housing 1705 that may include a variety of components. For example, microfluidic controller 1700 may include a microfluidic device input and output module 1710. The input and output module 1710 may be configured to control transporting a microfluidic device into and out of the microfluidic controller 1700. Microfluidic controller 1700 may include an input module 1720 for receiving input from a user and/or a display module 1725 for displaying information to a user. The input module 1720 and the display module 1725 may be integrated with each other, such as through a touch-screen display. Microfluidic controller 1700 may include a thermal cycling module 1730 that may be utilized to thermal cycle a microfluidic device. Microfluidic controller 1700 may include a pressure module 1740 that may be utilized to provide pressured fluid, including air, to a microfluidic device to actuate valves or otherwise control operation of the microfluidic device. Pressure module 1740 and thermal cycling module 1730 may work together such that a microfluidic device may be operated, such as through a mixing procedure, while thermal cycling occurs. Microfluidic controller 1700 may include a sealing module 1750 to provide one or more pressure seals with respect to the microfluidic device. In some embodiments, sealing module 1750 may include an interface plate.

Microfluidic controller 1700 may include one or more computer processor modules 1770 and/or one or more memory modules 1780 that may be utilized to operate different aspects of microfluidic controller 1700.

In some embodiments, microfluidic controller 1700 may include an imaging module 1760 that may be utilized for imaging one or more aspects of a microfluidic device or materials within the microfluidic device. The imaging module 1760 may be configured to image one or more aspects of the microfluidic device. The imaging module 1760 may include at least a microscope or a camera configured to image one or more captured cells in the microfluidic device. The imaging module 1760 may include at least a microscope or a camera configured to image one or more reaction products in the microfluidic device In some embodiments, the thermal cycling module 1730 is configured to thermal cycle the microfluidic device while the pressure module 1740 activates one or more valves within the microfluidic device. In some embodiments, the pressure module 1740 configured to couple with the microfluidic device to provide controller pressure to the microfluidic device is configured to control pressure in the microfluidic device to flow multiple cells through the microfluidic device and to capture individual cells at individual capture configurations within the microfluidic device.

The pressure module 1740 configured to couple with the microfluidic device to provide controller pressure to the microfluidic device may be configured to control pressure in the microfluidic device to perform multistage processing of multiple single cells captured within the microfluidic device. The thermal cycling module 1730 configured to thermal cycle the microfluidic device may be configured to perform the multistage processing of multiple single cells captured within the microfluidic device.

In some cases, the multistage processing facilitated by the microfluidic controller 1700 may include preamplification processing. The multistage processing may include mRNA sequence process in some cases.

The pressure module 1740 configured to couple with the microfluidic device to provide controller pressure to the microfluidic device may be configured to control pressure in the microfluidic device to prime the microfluidic device. The pressure module 1740 configured to couple with the microfluidic device to provide controller pressure to the microfluidic device may be configured to control pressure in the microfluidic device to load a plurality of cells into the microfluidic device and to capture multiple individual cells from the plurality of cells in the microfluidic device. At least the pressure module 1740 or the thermal cycling module 1730 may be configured to facilitate to perform at least lysis, reverse transcription, PCR, or harvesting on the microfluidic device. In some embodiments, at least the pressure module 1740 or the thermal cycling module 1730 may be configured to facilitate to perform at least lysis, reverse transcription, preamplification, or harvesting on the microfluidic device.

Figure 18:
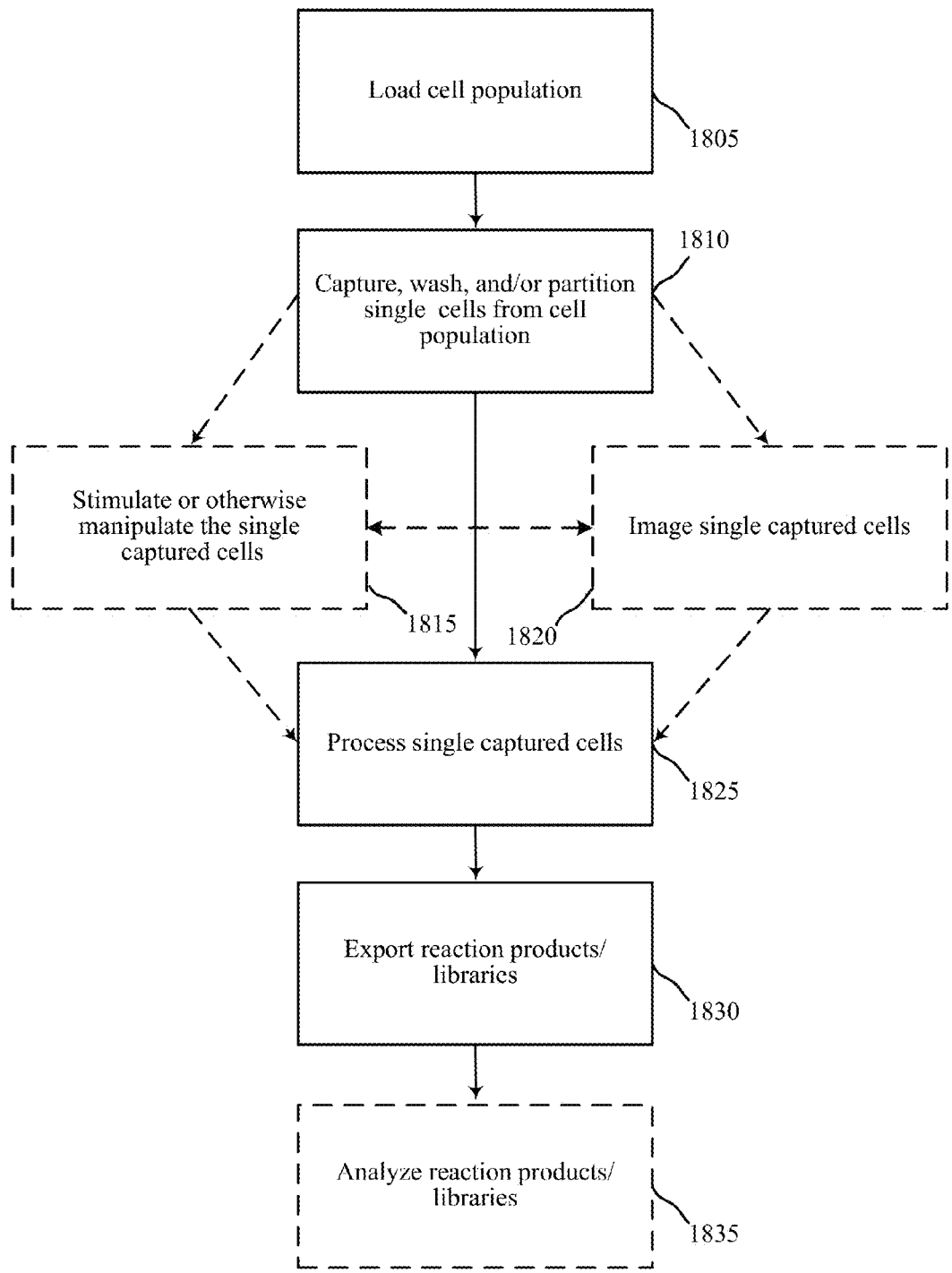
FIG. 18 shows a flow diagram of a method for processing multiple single cells using microfluidics in accordance with various embodiments.

Turning to FIG. 18, a method 1800 for multiple single-cell processing using microfluidics is shown in accordance with various embodiments. Method 1800 may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17.

At block 1805, a cell population may be loaded into a microfluidic device, which may include a microfluidic chip and carrier combination. In some embodiments, the cell population may include a cell population. At block 1810, single cells from the cell population may be captured, washed, and/or partitioned. In some embodiments, the single captured cells may be stimulated or otherwise manipulated such as seen in block 1815. In some embodiments, the single captured cells may be imaged as seen in block 1820.

At block 1825, the single captured cells may be processed. At block 1830, the reaction productions and/or libraries from the processed single captured cells may be exported. In some embodiments, the reaction products and/or libraries may be further analyzed.

Figure 19:
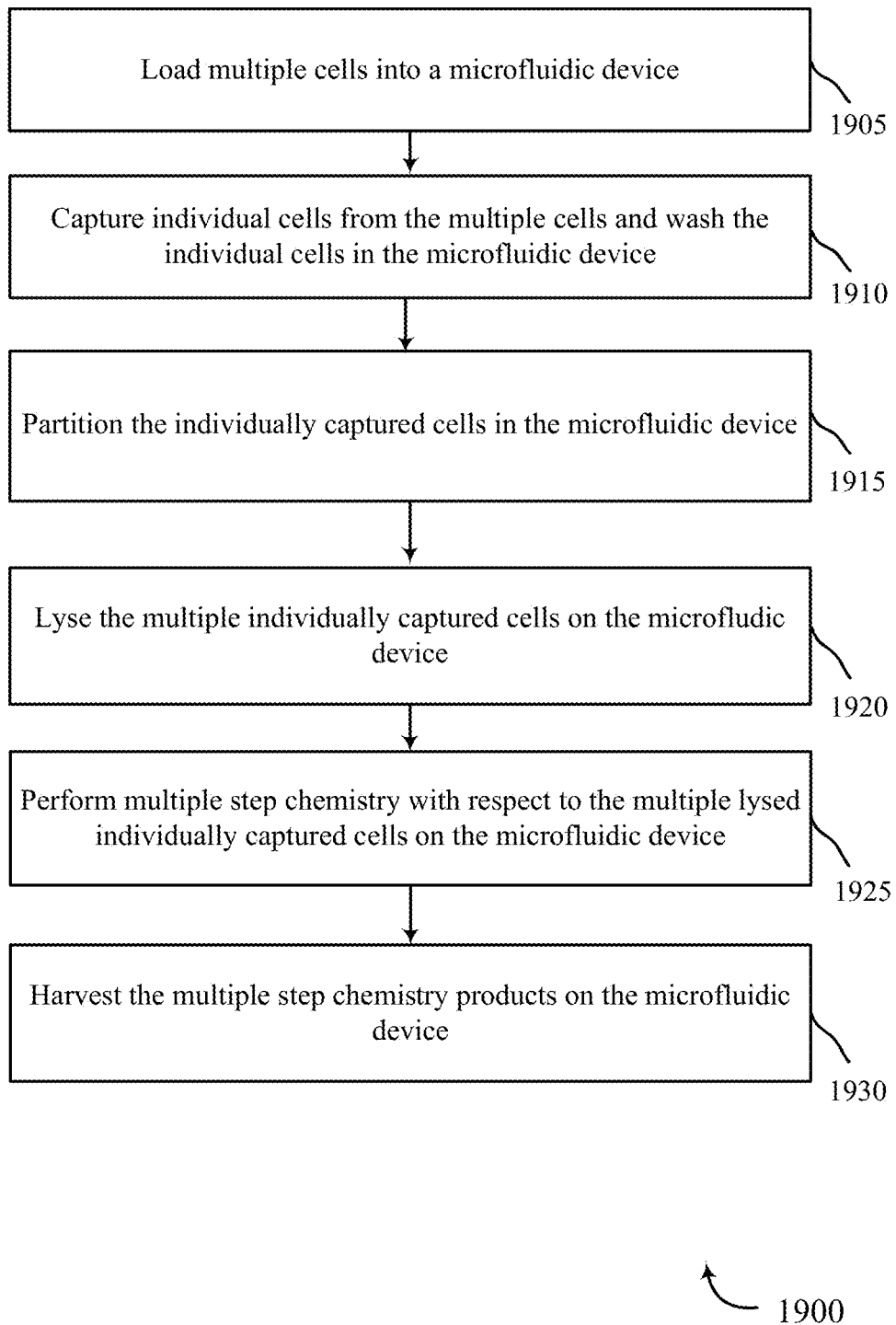
FIG. 19 shows a flow diagram of a method for processing multiple single cells using microfluidics in accordance with various embodiments.

Turning to FIG. 19, a method 1900 for multiple single-cell processing using microfluidics is shown in accordance with various embodiments. Method 1900 may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17.

At block 1905, multiple cells may be loaded into a microfluidic device. At block 1910, individual cells from the multiple cells may be capture and washed in the microfluidic device. At block 1915, the individually capture and wash cells may be partition in the microfluidic device. At block 1920, the multiple individually capture, washed, and partitioned cells may be lysed.

At block 1925, multistep chemistry may performed with respect to the multiple individually captured and lysed cells in the microfluidic device. For example, the multistep chemistry may include perform a first reaction (e.g., RT-PCT). In some embodiments, the multistep chemistry may include a second reaction (e.g., preamplification). At block 1930, the products from the multistep chemistry may be harvested on the microfluidic device.

In some cases, method 1900 may include a cell input and multiple different reagents that may be delivered into different reaction chambers serially.

Figure 20:
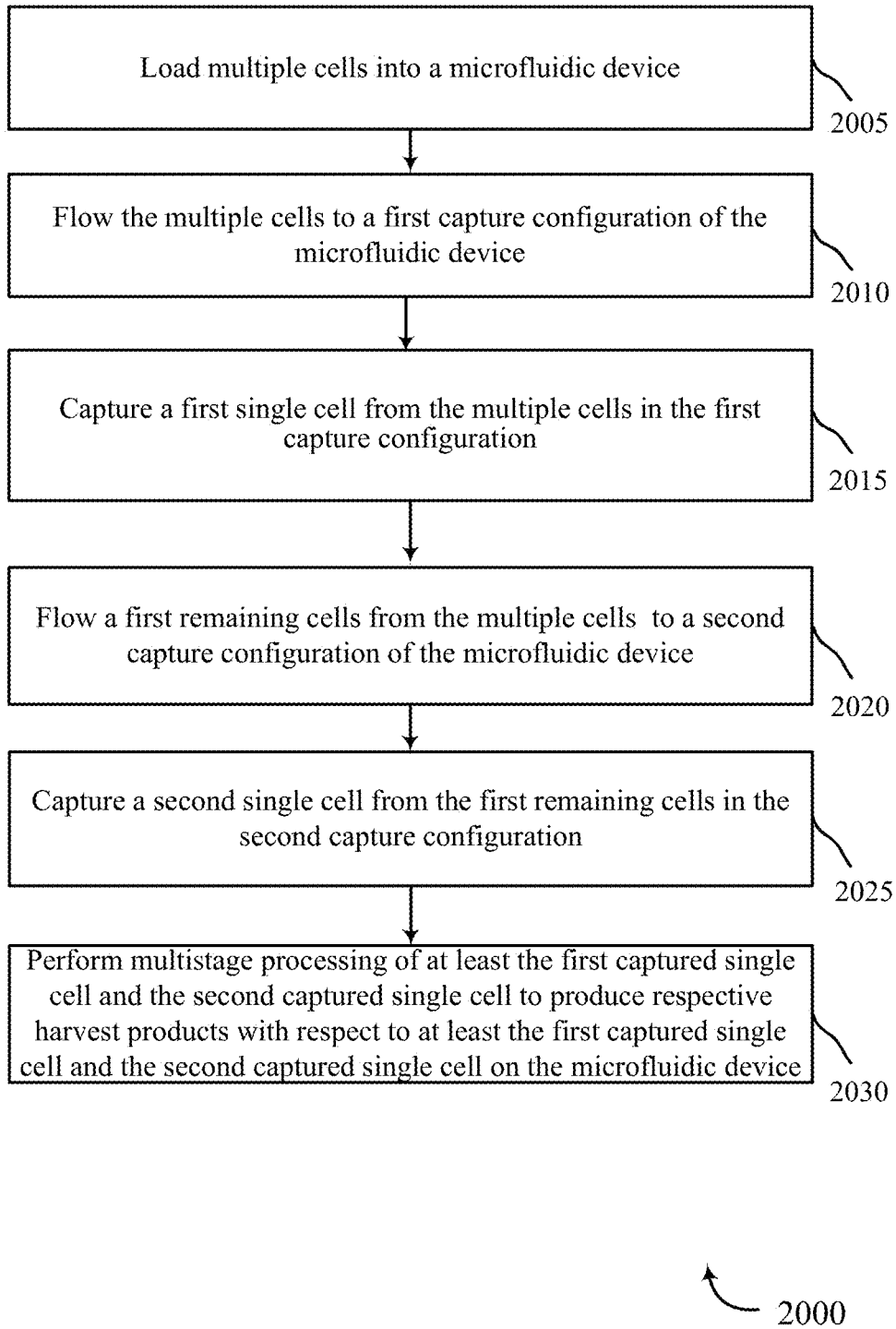
FIG. 20 shows a flow diagram of a method for capturing and processing multiple single cells using microfluidics in accordance with various embodiments.

Turning to FIG. 20, a method 2000 for multiple single-cell capturing and processing using microfluidics, is shown in accordance with various embodiments. Method 2000 may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17.

At block, 2005, multiple cells may be loaded into a microfluidic device. At block 2010, the multiple cells may be flowed to a first capture configuration of the microfluidic device. At block 2015, a first single cell from the multiple cells may be captured in the first capture configuration. At block 2020, a first remaining cells from the multiple cells may be flowed to a second capture configuration of the microfluidic device. At block 2025, a second single cell from the first remaining cells may be captured in the second capture configuration. At block 2030, multistage processing of at least the first captured single cell and the second captured single cell may be performed to produce respective harvest products with respect to at least the first captured single cell and the second captured single cell on the microfluidic device.

In some embodiments, capturing at least the first single cell or the second single cell at block 2015 may include capturing at least the first single cell or the second single cell utilizing one or more a physical barriers sized to hold only a single cell. Some embodiments include flowing the first remaining plurality of cells from the multiple cells through one or more bypass channels of the first capture configuration to a flow channel coupled with a second capture configuration coupled with the first output channel of the first capture configuration. Some embodiments include flowing a second remaining cells from the first remaining cells through one or more second bypass channels to an outlet of the second capture configuration to a third capture configuration through the second output channel.

In some embodiments, the first capture configuration includes: one or more bypass channels coupled with a first input channel and a first output channel; a first drain coupled with the first input channel and the first output channel; and/or a first capture nest coupled with the first drain and configured to capture an individual cell from the multiple cells. In some embodiments, the second capture configuration includes: multiple bypass channels coupled with a second input channel and a second output channel, wherein the second input channel is coupled with the first output channel of the first capture configuration; a second drain coupled with the second input channel and the second output channel; and/or a second capture nest coupled with a second drain configured to capture an individual cell from the first remaining cells.

In some embodiments, performing the multistage processing of at least the first captured single cell and the second captured single cell to produce respective harvest products with respect to at least the first captured single cell and the second captured single cell on the microfluidic device at block 2030 includes lysing, on the microfluidic device, each respective individually captured cell to release the one or more constituents of each respective cell. Performing the multistage processing of at least the first captured single cell and the second captured single cell to produce respective harvest products with respect to at least the first captured single cell and the second captured single cell on the microfluidic device at block 2030 may include flowing the one or more constituents of each respective captured cell into a respective multi-chamber reaction configuration of the microfluidic device for further processing. Performing the multistage processing of at least the first captured single cell and the second captured single cell to produce respective harvest products with respect to at least the first captured single cell and the second captured single cell on the microfluidic device at block 2030 may include performing a thermal cycling procedure while flowing the one or more constituents through one or more aspects of a respective multi-chamber reaction configuration of the microfluidic device.

In some embodiments, performing the multistage processing of at least the first captured single cell and the second captured single cell to produce respective harvest products with respect to at least the first captured single cell and the second captured single cell on the microfluidic device at block 2030 includes washing, in the microfluidic device, each respective captured cell with one or more reagents. In some embodiments, performing the multistage processing of at least the first captured single cell and the second captured single cell to produce respective harvest products with respect to at least the first captured single cell and the second captured single cell on the microfluidic device at block 2030 includes dosing, in the microfluidic device, each respective captured cell with one or more reagents.

Some embodiments of method 2000 include imaging the respective captured cells within the microfluidic device. Imaging may take place a different times with respect the captured cells.

In some embodiments, performing the multistage processing of at least the first captured single cell and the second captured single cell to produce respective harvest products with respect to at least the first captured single cell and the second captured single cell on the microfluidic device at block 2030 may include performing a preamplification process within the microfluidic device. Performing the multistage processing of at least the first captured single cell and the second captured single cell to produce respective harvest products with respect to at least the first captured single cell and the second captured single cell on the microfluidic device at block 2030 may include performing a mRNA sequence process within the microfluidic device.

In some embodiments, performing the multistage processing of at least the first captured single cell and the second captured single cell to produce respective harvest products with respect to at least the first captured single cell and the second captured single cell on the microfluidic device at block 2030 may include performing at least a specific target amplification, a whole genome amplification, a whole transcriptome amplification, a real-time PCR preparation, a copy number variation, or a haplotyping within the microfluidic device. Performing the multistage processing of at least the first captured single cell and the second captured single cell to produce respective harvest products with respect to at least the first captured single cell and the second captured single cell on the microfluidic device at block 2030 may include marking reaction products from the further processing associated with respective captured cells for identification purposes.

Some embodiments of method 2000 may include harvesting the harvest products from multiple harvest wells of the microfluidic device.

In some embodiments, capturing at least the first single cell or the second single cell may include capturing at least the first single cell or the second single cell utilizing a capture chamber configured to capture a single cell from a limiting dilution. In some embodiments, capturing at least the first single cell or the second single cell includes capturing at least the first single cell or the second single cell utilizing a stochastic capture process.

In some embodiments, capturing at least the first single cell or the second single cell includes: capturing at least the first single cell or the second single cell utilizing a capture compartment and/or a binding partner covering a discrete region of the capture compartment, where the discrete portion is sized so that only a single cell binds to the discrete region.

Capturing at least the first single cell or the second single cell may include capturing at least the first single cell or the second single cell utilizing one or more capture supports, wherein each capture support comprises a binding partner distributed over at least a portion of the capture support. The one or more capture supports may include one or more bead structures. Some embodiments include a capture feature configured to capture the capture support.

Figure 20A:
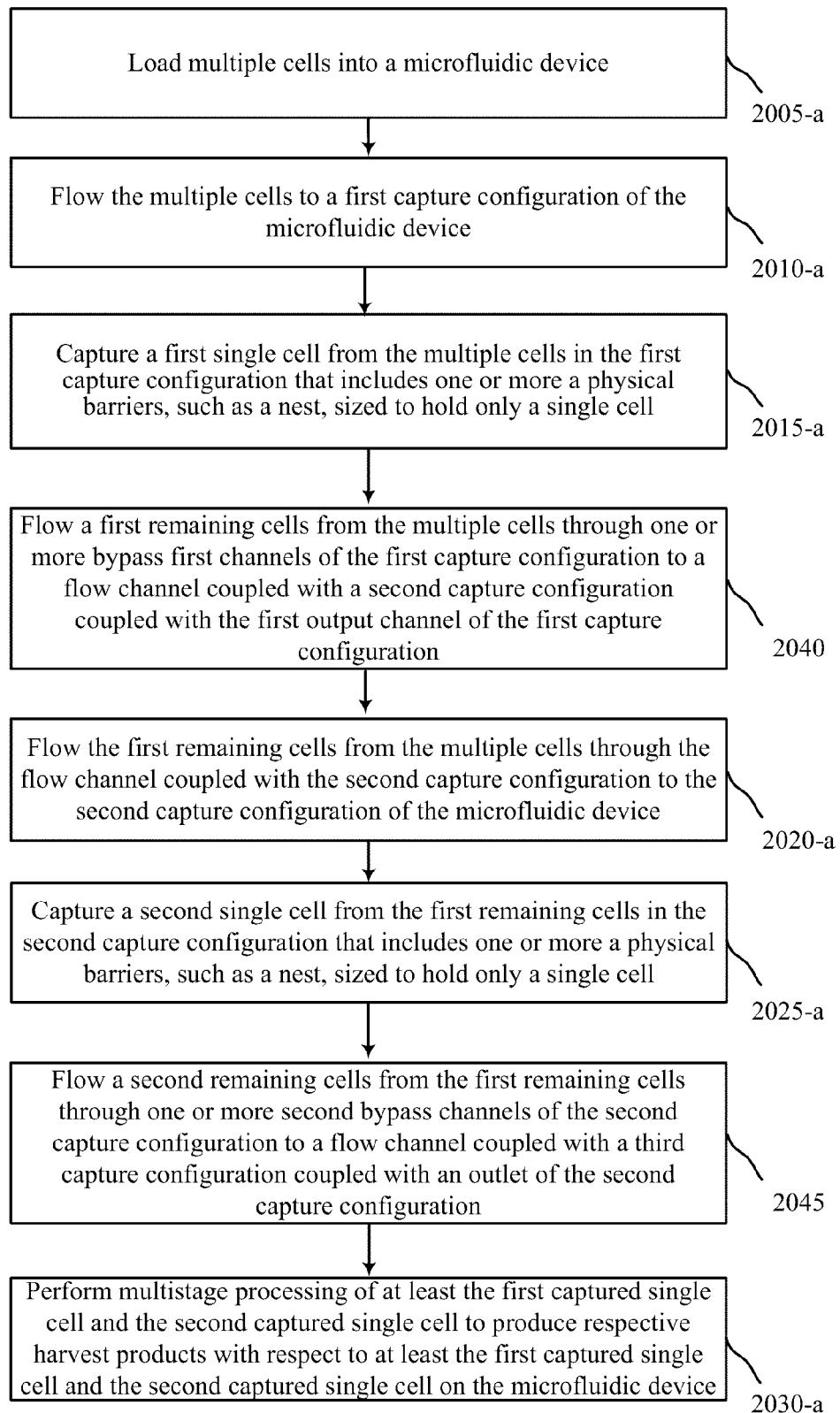
FIG. 20A shows a flow diagram of a method for capturing and processing multiple single cells using microfluidics in accordance with various embodiments.

Turning to FIG. 20A, a method 2000-a for multiple single-cell capturing and processing using microfluidics, is shown in accordance with various embodiments. Method 2000-a may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17. Method 2000-a may be an example of method 2000.

At block, 2005-a, multiple cells may be loaded into a microfluidic device. At block 2010-a, the multiple cells may be flowed to a first capture configuration of the microfluidic device. At block 2015-a, a first single cell from the multiple cells may be captured in the first capture configuration that includes one or more a physical barriers, such as a nest, sized to hold only a single cell. At block 2040, the first remaining plurality of cells from the multiple cells may be flowed through one or more first bypass channels of the first capture configuration to a flow channel coupled with a second capture configuration coupled with the first output channel of the first capture configuration. At block 2020-a, the first remaining cells from the multiple cells may be flowed through the flow channel coupled with the second capture configuration to the second capture configuration of the microfluidic device. At block 2025-a, a second single cell from the first remaining cells may be captured in the second capture configuration that includes one or more a physical barriers, such as a nest, sized to hold only a single cell. At block 2045, a second remaining cells from the first remaining cells may be flowed through one or more second bypass channels of the second capture configuration to a flow channel coupled with a third capture configuration coupled with an outlet of the second capture configuration. At block 2030-a, multistage processing of at least the first captured single cell and the second captured single cell may be performed to produce respective harvest products with respect to at least the first captured single cell and the second captured single cell on the microfluidic device.

Figure 20B:
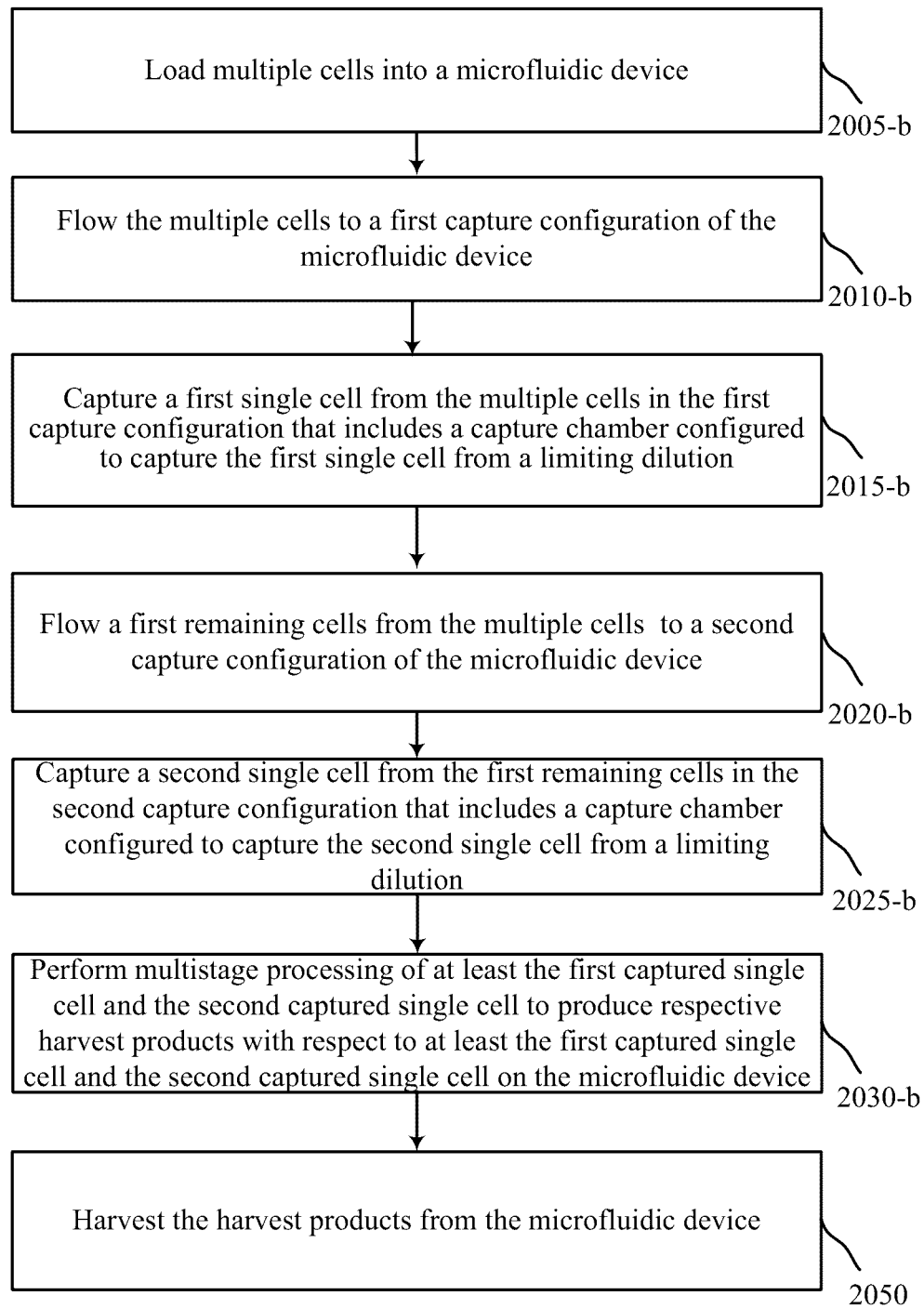
FIG. 20B shows a flow diagram of a method for capturing and processing multiple single cells using microfluidics in accordance with various embodiments.

Turning to FIG. 20B, a method 2000-b for multiple single-cell capturing and processing using microfluidics, is shown in accordance with various embodiments. Method 2000-b may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17. Method 2000-b may be an example of method 2000.

At block, 2005-b, multiple cells may be loaded into a microfluidic device. At block 2010-b, the multiple cells may be flowed to a first capture configuration of the microfluidic device. At block 2015-b, a first single cell from the multiple cells may be captured in the first capture configuration that includes a capture chamber configured to capture the first single cell from a limiting dilution. At block 2020-b, a first remaining cells from the multiple cells may be flowed to a second capture configuration of the microfluidic device. At block 2025-b, a second single cell from the first remaining cells may be captured in the second capture configuration that includes a capture chamber configured to capture the first single cell from a limiting dilution. At block 2030-b, multistage processing of at least the first captured single cell and the second captured single cell may be performed to produce respective harvest products with respect to at least the first captured single cell and the second captured single cell on the microfluidic device. At block 2050, the harvest products may be harvested from the microfluidic device.

Figure 21:
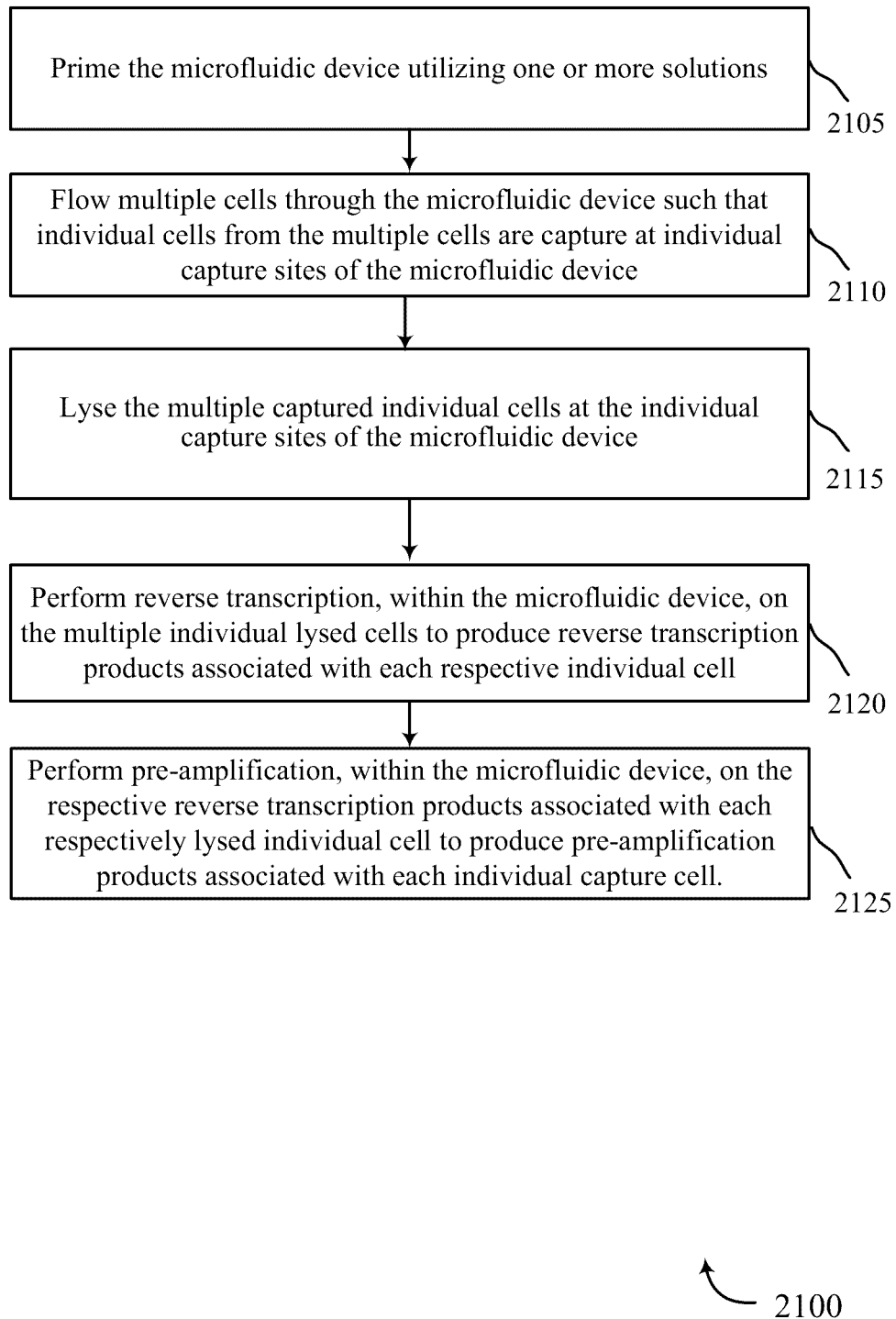
FIG. 21 shows a flow diagram of a method for capturing and preamplification processing multiple single cells using microfluidics in accordance with various embodiments.

Turning to FIG. 21, a method 2100 of preamplification utilizing a microfluidic device configured to capture and to process individual cells from multiple cells is shown in accordance with various embodiments. Method 2100 may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17.

Method 2100 may allow a user to capture cells and perform target preamplification using microfluidic device and/or controller as disclosed herein. Method 2100 may provide for capturing cells, staining for viability, imaging cells, lysing cells, performing reverse transcription and/or preamplification, and finally, harvesting the amplified products. Method 2100 may provide for evaluating the RNA content of cells and to harvest the products generated. Gene expression analysis of preamplified amplicons may then be performed with a genomic array.

Preamplification may enrich samples for loci of interest, maintain relative abundance between loci, and/or permits quantitative Cq information to be derived. Quantitative PCR may then be performed in the presence of a DNA binding dye (EvaGreen). Quantitative PCR is immediately followed by acquisition of a melting curve to allow assessment of reaction quality.

At block 2105, the microfluidic device may be primed utilizing one or more solutions. At block 2110, the multiple cells may be flowed through the microfluidic device such that individual cells from the multiple cells are capture at individual capture sites of the microfluidic device. At block 2115, the multiple captured individual cells may be lysed at the individual capture sites of the microfluidic device. At block 2120, reverse transcription may be performed, within the microfluidic device, on the multiple individually lysed cells to produce reverse transcription products associated with each respective individual cell. At block 2125, preamplification may be performed, within the microfluidic device, on the respective reverse transcription products associated with each respectively lysed individual cell to produce preamplification products associated with each individual capture cell.

Some embodiments of method 2100 include delivering the preamplification products associated with each individual capture cell to a respective harvest inlet from a plurality of harvest inlets of the microfluidic device.

Method 2100 may include preparing one or more solutions to load into the microfluidic device. Method 2100 may include loading the one or more solutions into the microfluidic device. The one or more solutions may include at least one or more reagents or one or more buffers. Method 2100 may include loading the multiple cells into the microfluidic device Some embodiments of method 2100 include imaging one or more of the captured individual cells on the microfluidic device.

Method 2100 may include loading at least one or more lysis reagents, one or more reverse transcription reagents, or one or more preamplification reagents into the microfluidic device. Method 2100 may include: removing one or more protective layers of one or more harvesting inlets; and/or harvesting the preamplification products from each respective harvest inlet from the plurality of harvest inlets of the microfluidic device.

Some embodiments include staining the one or more individual capture cells on the microfluidic device. Some embodiments include determining whether the one or more individual captured cells are alive or dead based on the staining. Method 2100 may include determining whether the one or more individual captured cells are alive or dead based on the imaging.

Figure 21A:
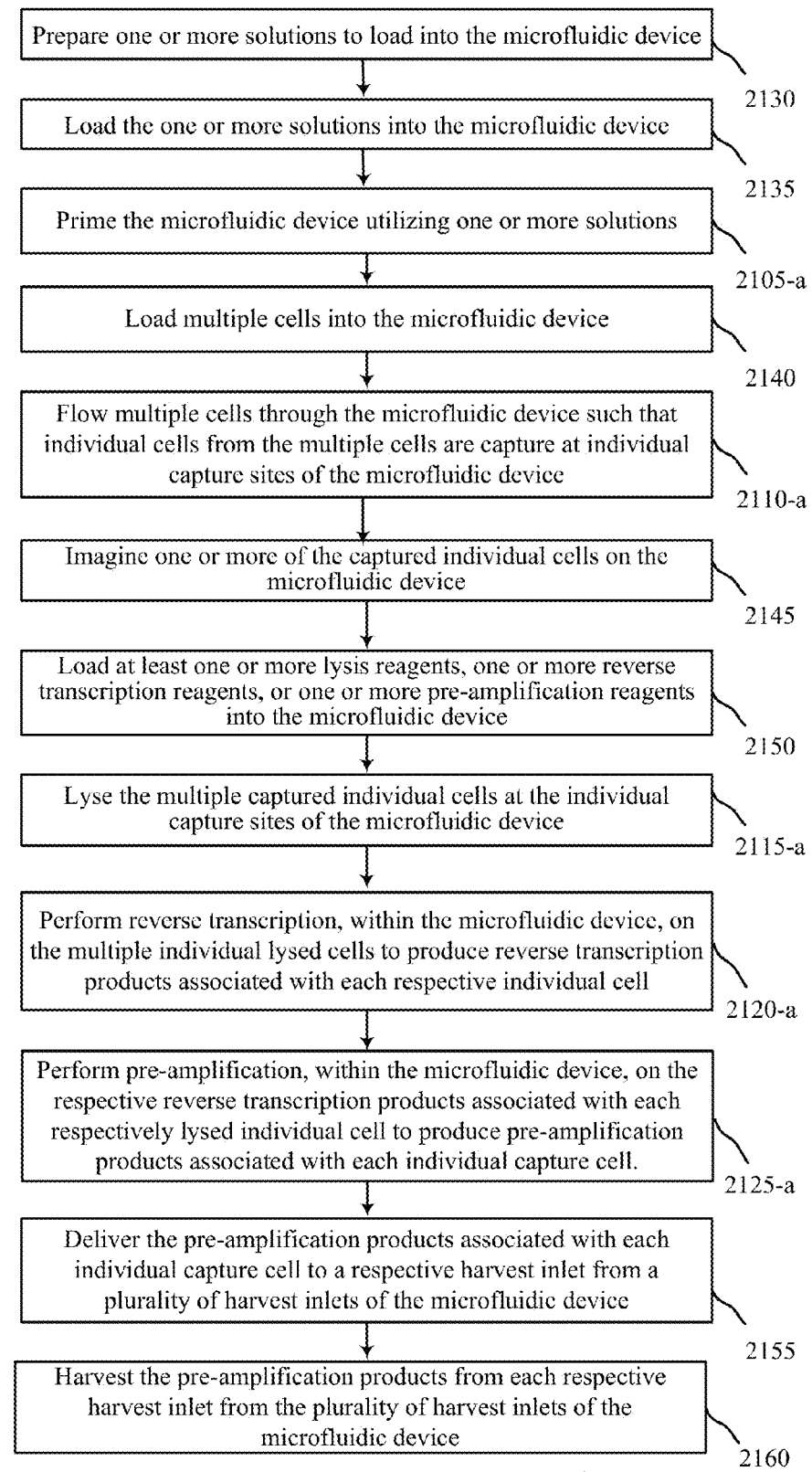
FIG. 21A shows a flow diagram of a method for capturing and preamplification processing multiple single cells using microfluidics in accordance with various embodiments.

Turning to FIG. 21A, a method 2100-a of preamplification utilizing a microfluidic device configured to capture and to process individual cells from multiple cells is shown in accordance with various embodiments. Method 2100-a may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17. Method 2100-a may be an example of method 2100.

At block 2130, one or more solutions may be prepared to load into the microfluidic device. The one or more solutions may include a variety of reagents and/or buffers including but not limited to: RAN spikes, pooled primers, lysis reagents, reverse transcription reagents, preamplification reagents, and/or cell staining solutions. RNA spikes may include, but is not limited to, ArrayControl RNA spikes and/or RNA storage solution. Pooled primers may include, but is not limited to, primer stocks and/or DNA dilution reagents. Lysis reagents may include, but is not limited to, single-cell lysis solution and/or lysis reagent. RT reagents may include, but is not limited to, stop solution, single cell VILO RT, single cell super script RT, and/or loading reagents. Preamplification reagents may include, but is not limited to, single cell preamplification reagents, preamplification dilatation reagents. Cell staining solutions may include, but is not limited to cell wash buffer, Ethidium homodimer-1 and/or Calcein AM. Some embodiments may also utilize priming agents such as blocking reagents and/or preloading reagents. Some embodiments may also utilize suspension reagent.

At block 2135, the one or more solutions may be loaded into the microfluidic device. The one or more solutions may include at least one or more reagents or one or more buffers. The solutions may be pipetted into the microfluidic device through different ports, such as those shown in FIG. 16. The solutions may include, but are not limited to, harvest reagents, preloading reagents, blocking reagents, and/or cell wash buffer. At block 2105-a, the microfluidic device may be primed utilizing one or more solutions.

At block 2140, multiple cells may be loaded into the microfluidic device. A cell suspension may be created that may include a native medium prior to mixing a suspension reagent and loading the microfluidic device. For example, the concentration may be 166-250 K/ml; other concentrations may be utilized. A cell mixture may be combined with a suspension reagent. For example, the reagent with cells may be at a ratio, such as 4:6. The cell mixture may be pipette into the different ports, such as those shown in FIG. 16, for example Staining solution and/or blocking reagent may also be loaded into the microfluidic device. At block 2110-a, the multiple cells may be flowed through the microfluidic device such that individual cells from the multiple cells are capture at individual capture sites of the microfluidic device. A controller such as the controller of FIG. 17, for example, may be utilized to flow the cells through the microfluidic device such that cells are captured at individual capture sites.

At block 2145, one or more of the captured individual cells may be imaged on the microfluidic device. For example, cells may be imaged using a microscope and/or camera that may be compatible with the microfluidic device. The capture cells may be imaged at different times, such as before or after being washed, or before or after being stained.

At block 2150, at least one or more lysis reagents, one or more reverse transcription reagents, or one or more preamplification reagents may be loaded into the microfluidic device. For example, harvest reagents, lysis reagents, RT reagents, and preamplification reagents may be loaded into the device. FIG. 16 may show an example of a carrier that includes ports where these different reagents may be loaded into the microfluidic device.

At block 2115-a, the multiple captured individual cells may be lysed at the individual capture sites of the microfluidic device. At block 2120-a, reverse transcription may be performed, within the microfluidic device, on the multiple individually lysed cells to produce reverse transcription products associated with each respective individual cell. At block 2125-a, preamplification may be performed, within the microfluidic device, on the respective reverse transcription products associated with each respectively lysed individual cell to produce preamplification products associated with each individual capture cell. At block 2155, the preamplification products associated with each individual capture cell may be delivered to a respective harvest inlet from a plurality of harvest inlets of the microfluidic device. In some cases, a controller, such as the controller of FIG. 17, may be utilized to facilitate performing these steps.

At block 2160, the preamplification products may be harvested from each respective harvest inlet from the plurality of harvest inlets of the microfluidic device. Some embodiments include removing one or more protective layers of one or more harvesting inlets. The protective layers may be utilized to avoid contamination. The harvest products, such may be referred to as harvest amplicons, may be analyzed in subsequent analysis, such as different genomic analyses utilize one or more genomic analysis arrays and/or controllers. In some cases, the genomic analysis array may be integrated with the microfluidic device.

Figure 22:
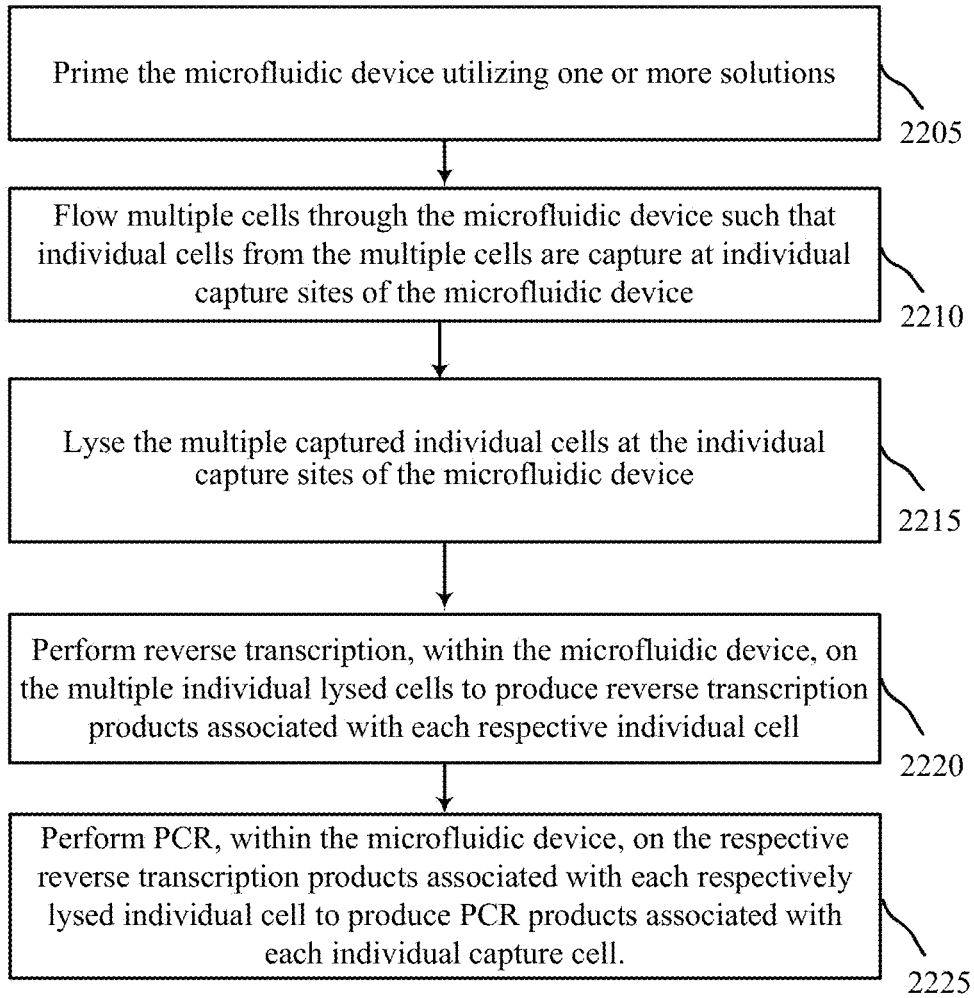
FIG. 22 shows a flow diagram of a method for capturing and mRNA sequencing multiple single cells using microfluidics in accordance with various embodiments.

Turning to FIG. 22, a method 2200 of mRNA sequencing utilizing a microfluidic device configured to capture and to process individual cells from multiple cells is shown in accordance with various embodiments. Method 2200 may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17.

Method 2200 may allow the user to capture cells, convert polyA+ RNA into full-length cDNA, and/or then perform universal amplification of the cDNA, for example. Some embodiment performed during cDNA synthesis, including: capturing cells, staining for viability, imaging cells, lysing cells, performing reverse transcription and long-distance PCR, and/or harvesting the amplified cDNA. To perform analysis by mRNA Seq, the full-length cDNA may first be converted to a sequencing library, and the final steps of library generation from cDNA are described in a mRNA Seq Library Preparation for Sequencing Protocol. If desired, direct gene expression analysis of full-length cDNA can also be performed through qPCR, for example.

Some embodiments may use a modified oligo (dT) primer to prime first strand synthesis, and thus may select for polyA+ RNA in a sample. When the reverse transcriptase (RT) reaches the 5' end of the mRNA, the enzyme's terminal transferase activity may add a few non-templated deoxycytidines to the 3' end of the cDNA. The template-switch primer may contain a few guanosines at its 3' end that base-pair with the non-templated deoxycytidines on the cDNA to create an extended template. The RT then may extend to the end of the template-switch primer, producing single-stranded cDNA that may contain a universal tag sequence, the 3' end of the mRNA, the full-length transcript up to the 5' end of the mRNA, and/or finally the reverse complement of a universal tag sequence. Prematurely terminated cDNAs, contaminating genomic DNA, or cDNA transcribed from RNA without polyA tail may not contain universal tag at both ends and will not be exponentially amplified during long-distance PCR. However, degraded RNAs present in low quality RNA that still have polyA tails may be amplified, yielding shorter cDNA fragments with incomplete coverage at the 5' end of the transcript. Full-length transcripts may be enriched during PCR since a universal tag, found at the 5' end of the cDNA, for example, can pair with its own reverse complement, found at the 3' end of short cDNAs, that may prevent amplification of short cDNAs.

At block 2205, the microfluidic device may be primed utilizing one or more solutions. At block 2210, the multiple cells may be flowed through the microfluidic device such that individual cells from the multiple cells are capture at individual capture sites of the microfluidic device. At block 2215, the multiple captured individual cells may be lysed at the individual capture sites of the microfluidic device. At block 2220, reverse transcription may be performed, within the microfluidic device, on the multiple individually lysed cells to produce reverse transcription products associated with each respective individual cell. At block 2225, PCR may be performed, within the microfluidic device, on the respective reverse transcription products associated with each respectively lysed individual cell to produce PCR products associated with each individual capture cell.

Some embodiments of method 2200 include delivering the PCR products associated with each individual capture cell to a respective harvest inlet from a plurality of harvest inlets of the microfluidic device. Method 2100 may include loading the one or more solutions into the microfluidic device. The one or more solutions may include at least one or more reagents or one or more buffers.

Method 2200 may include loading the multiple cells into the microfluidic device. Some embodiments include imaging one or more of the captured individual cells on the microfluidic device. Some embodiments of method 2200 include loading at least one or more lysis reagents, one or more reverse transcription reagents, or one or more PCR reagents into the microfluidic device.

Some embodiments of method 2200 include removing one or more protective layers of one or more harvesting inlets. The PCR products may be harvested from each respective harvest inlet from the plurality of harvest inlets of the microfluidic device.

Method 2200 may include staining the one or more individual capture cells on the microfluidic device. Method 2200 may include determining whether the one or more individual captured cells are alive or dead based on the staining. Method 2200 may include determining whether the one or more individual captured cells are alive or dead based on the imaging.

In some cases, the PCR products include amplified cDNA. Some embodiments include preparing one or more libraries utilizing the PCR products associated with each individual captured cell. Preparing the one or more libraries may include determining a cDNA concentration from each respective harvest products associated with each individual cell and/or diluting each respective cDNA concentration to within a pre-determined concentration range. Some embodiments include preparing the dilated cDNA concentration for tagmentation to produce tagmentation products. Some embodiments include performing PCR amplification on the tagmentation products to produce PCR products. Method 2200 may include generating one or more library pools from the PCR products.

Figure 22A:
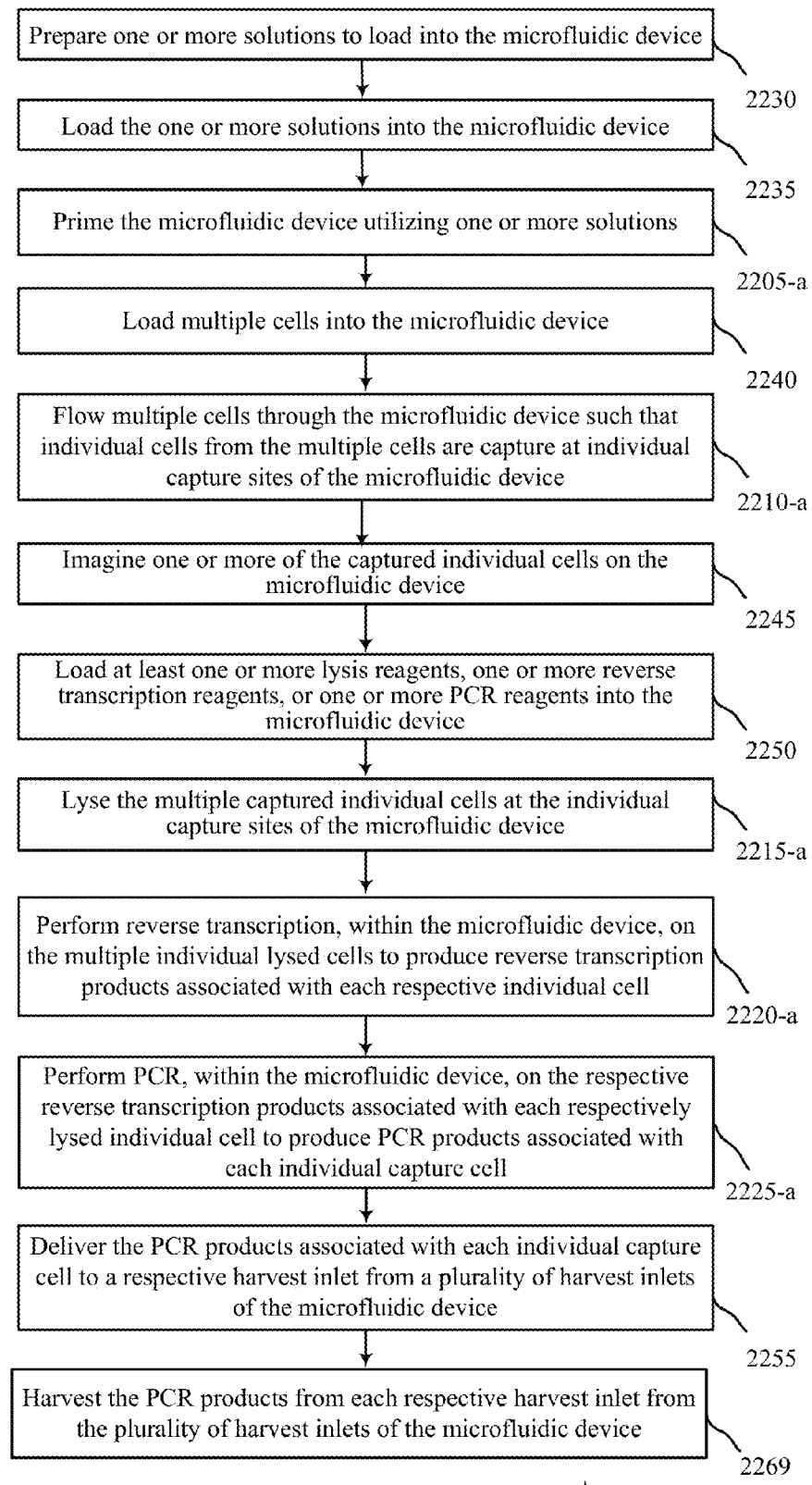
FIG. 22A shows a flow diagram of a method for capturing and mRNA sequencing multiple single cells using microfluidics in accordance with various embodiments.

Turning to FIG. 22A, a method 2200-a of mRNA sequencing utilizing a microfluidic device configured to capture and to process individual cells from multiple cells is shown in accordance with various embodiments. Method 2200-a may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17. Method 2200-a may be an example of method 2200.

At block 2230, one or more solutions may be prepared to load into the microfluidic device. The one or more solutions may include at least one or more reagents or one or more buffers. For example, the solutions may include, but are not limited to: RNA spikes, lysis reagents, reverse transcription reagents, PCR reagents, cell staining solutions, and/or cell mix reagents. In some embodiments, the RNA spikes may include RNA storage solution and/or Array Control RNA spikes. RNA spikes may serve as a positive control for thermal cycling. The lysis reagents may include, but are not limited to, loading reagents, RNAs inhibitor, 3' CDS primer, and/or dilatation buffer. In some embodiments, the RT reagents may include 5× first-strand buffer, dithiothreitol, dNTP reagents, and/or reverse transcriptase regents. The PCR reagents may include, but are not limited to, PCR water, 10× advantage 2 PCR buffer, 50× dNTP reagents, IS PCR primer, and/or 50× advantage 2 polymerase reagents. Cell reagents may include, but are not limited to, cells and/or suspension reagents. Cell staining solutions may include cell wash buffer, Ethidium homodimer-1, and/or Calcein AM, for example.

At block 2235, the one or more solutions may be loaded into the microfluidic device. Merely by way of example, the solutions may be loaded into the microfluidic chip through ports in a microfluidic carrier, such as that shown in FIG. 16. At block 2205-a, the microfluidic device may be primed utilizing one or more solutions. Priming agents may include, but are not limited to, preloading reagents, harvest reagents, and/or block reagents.

At block 2240, multiple cells may be loaded into the microfluidic device. In some cases, the cells may be prepared in a suspension that may include a suspension reagent. In some embodiments, the concentration may be between 166-250 K/ml in native medium prior to mixing with the suspension reagent. The cells may be loaded into the microfluidic device through ports in a microfluidic carrier, such as that shown in FIG. 16, for example.

At block 2210-a, the multiple cells may be flowed through the microfluidic device such that individual cells from the multiple cells are capture at individual capture sites of the microfluidic device. This may utilize a controller, such as the controller of FIG. 17, for example.

At block 2245, one or more of the captured individual cells may be imaged on the microfluidic device. The cells may be imaged with a microscope and/or camera that may be compatible with the microfluidic device.

At block 2250, at least one or more lysis reagents, one or more reverse transcription reagents, or one or more PCR reagents may be loaded into the microfluidic device. This may include, for example, loading harvest reagent, lysis reagents, RT reagents, and/or PCR reagents into different ports of a carrier, such as that shown in FIG. 16, for example.

At block 2215-*a*, the multiple captured individual cells may be lysed at the individual capture sites of the microfluidic device. At block 2220-*a*, reverse transcription may be performed, within the microfluidic device, on the multiple individually lysed cells to produce reverse transcription products associated with each respective individual cell. At block 2225-*a*, PCR may be performed, within the microfluidic device, on the respective reverse transcription products associated with each respectively lysed individual cell to produce PCR products associated with each individual capture cell. A controller, such as the controller of FIG. 17, may be utilized to control the performance of each of these blocks.

At block 2255, the PCR products associated with each individual capture cell may be delivered to a respective harvest inlet from a plurality of harvest inlets of the microfluidic device. At block 2260, the PCR products may be harvested from each respective harvest inlet from the multiple harvest inlets of the microfluidic device. Some embodiments include removing one or more protective layers of one or more harvesting inlets to facilitate harvesting the PCR products.

Figure 22B:
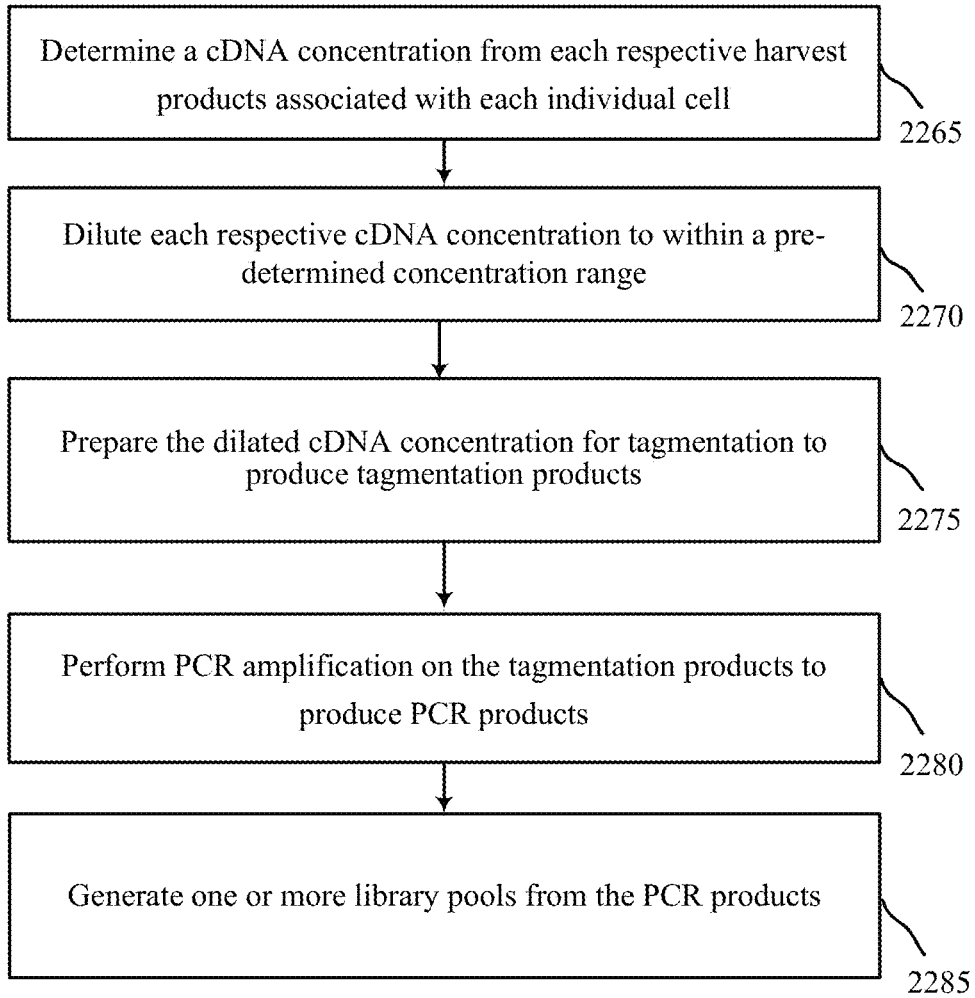
FIG. 22B shows a flow diagram of a method for capturing and mRNA sequencing multiple single cells using microfluidics in accordance with various embodiments.

Turning to FIG. 22B, a method 2200-*b* of mRNA sequencing utilizing a microfluidic device configured to capture and to process individual cells from multiple cells is shown in accordance with various embodiments. Method 2200-*b* may be implemented utilizing a variety of different systems and/or devices including, but not limited to, microfluidic device 110 of FIG. 1 and/or FIG. 2, and/or microfluidic device 1600 of FIG. 16, for example, and/or microfluidic controller 120 of system 100 of FIG. 1 and/or FIG. 17. Method 2200-*b* may be combined with method 2200 and/or method 2200-*a* in some cases.

Method 2200-*b* may include preparing one or more libraries utilizing the PCR products associated with each individual captured cell. For example, at block 2265, a cDNA concentration may be determined from each respective harvest products associated with each individual cell.

At block 2270, each respective cDNA concentration may be diluted to within a pre-determined concentration range. At block 2275, the dilated cDNA concentration may be prepared for tagmentation to produce tagmentation products. At block 2280, PCR amplification may be performed on the tagmentation products to produce PCR products. At block 2285, one or more library pools may be generated from the PCR products.

The detailed description set forth above in connection with the appended drawings describes exemplary embodiments and does not represent the only embodiments that may be implemented or that are within the scope of the claims. The term "exemplary" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Some of the various illustrative blocks and modules described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

Some of the functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C).

Computer-readable media includes both computer storage media and communication media including any medium that facilitates transfer of a computer program from one place to another. A storage medium may be any available medium that can be accessed by a general-purpose or special-purpose computer. By way of example, and not limitation, computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

What is claimed is:

1. A method of amplifying mRNA sequences from individual eukaryotic cells using a microfluidic device configured to capture and to process individual cells from a plurality of cells, the method comprising:
   a) priming the microfluidic device by flowing one or more solutions through a plurality of capture configurations of the device;
   b) flowing a cell suspension comprising the plurality of cells in solution through channels of the microfluidic device such that individual cells from the plurality of cells are captured at individual capture sites of the plurality of capture configurations, wherein each capture configuration comprises
      a capture site comprising one or more physical barriers configured to capture a single cell, an input channel through which cells can flow towards the capture site, an output channel through which cells can flow away from the capture site, a drain channel, and one or more bypass channels, and the physical barriers, drain channel, and bypass channel(s) are configured so that when capture site is unoccupied by a cell solution flows past the one or more physical barriers into the drain channel, and from the drain channel into the output channel, and when the capture site is occupied by a captured cell, flow through the drain channel is blocked by the captured cell and cells that are not captured are diverted into a bypass channel;
   c) lysing the plurality of captured individual cells at the individual capture sites of the microfluidic device thereby releasing RNA from the individual captured cells at the individual capture sites;
   d) performing separate individual reverse transcription reactions, within the microfluidic device, on the RNA released from the individual lysed cells to produce reverse transcription products associated with each respective individual captured cell; and
   e) performing PCR, within the microfluidic device, on the respective reverse transcription products associated with each respectively lysed individual cell to produce PCR products associated with each individual capture cell.

2. The method of claim 1, further comprising:
   delivering the PCR products associated with each individual captured cell to a respective harvest inlet from a plurality of harvest inlets of the microfluidic device.

3. The method of claim 1, further comprising:
   loading the one or more solutions into the microfluidic device.

4. The method of claim 1, wherein the one or more solutions includes at least one or more reagents or one or more buffers.

5. The method of claim 1, further comprising:
   loading the plurality of cells into the microfluidic device.

6. The method of claim 1, further comprising:
   imaging one or more of the captured individual cells on the microfluidic device.

7. The method of claim 1, further comprising:
   loading at least one or more lysis reagents, one or more reverse transcription reagents, or one or more PCR reagents into the microfluidic device.

8. The method of claim 1, further comprising:
   removing one or more protective layers of one or more harvesting inlets; and harvesting the PCR products from each respective harvest inlet from the plurality of harvest inlets of the microfluidic device.

9. The method of claim 1, further comprising:
   staining the one or more individual capture cells on the microfluidic device.

10. The method of claim 9, further comprising:
    determining whether the one or more individual captured cells are alive or dead based on the staining.

11. The method of claim 6, further comprising:
    determining whether the one or more individual captured cells are alive or dead based on the imaging.

12. The method of claim 1, further comprising:
    preparing one or more libraries utilizing the PCR products associated with each individual captured cell.

13. The method of claim 12, wherein preparing the one or more libraries comprises:
    determining a cDNA concentration from each respective harvest products associated with each individual cell; and
    diluting each respective cDNA concentration to within a pre-determined concentration range.

14. The method of claim 13, further comprising:
    preparing the diluted cDNA concentration for tagmentation to produce tagmentation products.

15. The method of claim 14, further comprising:
    performing PCR amplification on the tagmentation products to produce PCR products.

16. The method of claim 1, wherein the microfluidic device comprises a plurality of capture configurations coupled in series, each respective capture configuration comprising:
    a plurality of bypass channels
    a capture nest comprising a concave surface formed by said one or more physical barriers, situated proximal to a junction of the input channel and the plurality of bypass channels and coupled with the drain channel, wherein the capture nest is configured to capture an individual cell from the plurality of cells such that a remaining plurality of cells is diverted into at least one of the plurality of bypass channels when the individual cell is captured in the capture nest; and
    a plurality of multi-chamber reaction configurations, wherein each respective multi-chamber reaction configuration is coupled with a respective capture configuration from the plurality of capture configurations and configured for single-cell processing.

17. A method of mRNA processing utilizing a microfluidic device configured to capture and to process individual cells from a plurality of cells, the method comprising:
    loading one or more solutions into the microfluidic device;
    priming the microfluidic device utilizing the one or more solutions;
    loading at least one or more lysis reagents or one or more reverse transcription reagents, into the microfluidic device;
    loading the plurality of cells into the microfluidic device;

flowing the plurality of cells through the microfluidic device such that individual cells from the plurality of cells are captured at individual capture sites of the microfluidic device;

imaging one or more of the captured individual cells on the microfluidic device;

lysing the plurality of captured individual cells at the individual capture sites of the microfluidic device;

performing reverse transcription, within the microfluidic device, on the plurality of individual lysed cells to produce reverse transcription products associated with each respective individual cell;

performing polymerase-mediated amplification within the microfluidic device, on the respective reverse transcription products associated with each respectively lysed individual cell to produce PCR products associated with each individual capture cell;

delivering the amplification products associated with each individual capture cell to a respective harvest inlet from a plurality of harvest inlets of the microfluidic device;

removing one or more protective layers of one or more harvesting inlets; and harvesting the amplification products from each respective harvest inlet from the plurality of harvest inlets of the microfluidic device.

18. The method of claim 16 wherein performing PCR comprises active mixing between multiple chambers of the multi-chamber reaction configuration.

19. The method of claim 1 wherein the microfluidic device comprises a plurality of multi-chamber reaction configurations for performing PCR, wherein each respective multi-chamber reaction configuration is coupled with a respective capture configuration from the plurality of capture configurations.

20. The method of claim 19 wherein performing PCR comprises active mixing between multiple chambers of the multi-chamber configuration.

21. The method of claim 17 wherein the polymerase-mediated amplification is PCR.

22. The method of claim 17 wherein active mixing between multiple chambers of the multi-chamber reaction configuration occurs during the reverse transcription and/or polymerase-mediated amplification steps.

23. The method of claim 1 comprising exposing captured individual cells to one or more biological or chemical modulator(s) before lysis.

24. The method of claim 1 comprising the step of confirming the presence of a single captured cell by distinguishing the presence of a single cell from absence of a cell or the presence of two cells.

25. The method of claim 1, wherein the one or more bypass channels comprise a first bypass channel and a second bypass channel.

26. The method of claim 25, wherein the first bypass channel and the second bypass channel are symmetrically configured.

27. The method of claim 26, wherein the symmetrically configured first bypass channel and second bypass channel comprise a first wing configuration and a second wing configuration.

* * * * *